US006638739B2

(12) United States Patent
Classen

(10) Patent No.: US 6,638,739 B2
(45) Date of Patent: *Oct. 28, 2003

(54) METHOD AND COMPOSITION FOR AN EARLY VACCINE TO PROTECT AGAINST BOTH COMMON INFECTIOUS DISEASES AND CHRONIC IMMUNE MEDIATED DISORDERS OR THEIR SEQUELAE

(75) Inventor: John Barthelow Classen, Baltimore, MD (US)

(73) Assignee: Classen Immunotherapies, Inc., Baltimore, MD (US)

(*) Notice: Subject to any disclaimer, the term of this patent is extended or adjusted under 35 U.S.C. 154(b) by 6 days.

This patent is subject to a terminal disclaimer.

(21) Appl. No.: 10/124,363

(22) Filed: Apr. 18, 2002

(65) Prior Publication Data

US 2002/0155436 A1 Oct. 24, 2002

Related U.S. Application Data

(63) Continuation of application No. 09/611,415, filed on Jul. 6, 2000, now Pat. No. 6,420,139, which is a continuation of application No. 08/591,651, filed as application No. PCT/US94/08825 on Aug. 4, 1994, which is a continuation of application No. 08/104,529, filed on Aug. 12, 1993, now Pat. No. 5,728,385.

(51) Int. Cl.[7] ................. C12N 15/09; C12N 5/00; G01N 33/53

(52) U.S. Cl. .............. 435/69.3; 435/7.1; 435/325

(58) Field of Search .................. 435/69.3, 7.1, 435/325

(56) References Cited

U.S. PATENT DOCUMENTS 4,152,415 A * 5/1979 Harries ...................... 424/16
4,625,015 A * 11/1986 Green ........................ 530/324
4,695,459 A   9/1987 Steinman .................... 424/95
4,710,380 A   12/1987 Gottlieb ..................... 424/101
4,857,318 A * 8/1989 Lee et al. .................... 424/92
4,894,532 A * 1/1990 Schallen et al. ........... 435/69.3
5,139,776 A * 8/1992 Chazano et al. ............. 424/92
5,151,023 A * 9/1992 Kuzuhara .................... 424/89
5,254,340 A * 10/1993 Van Leengoed ............. 424/92
5,723,283 A * 3/1998 Classen ......................... 435/4
5,728,385 A * 3/1998 Classen .................... 424/201.1
6,420,139 B1 * 7/2002 Classen .................... 435/69.3

FOREIGN PATENT DOCUMENTS

EP    0094575    11/1983
EP    0343480    5/1989
WO    8912455    12/1989
WO    9010449    9/1990
WO    9200755    1/1992
WO    9203733    3/1992

OTHER PUBLICATIONS

Webster's II New Riverside Dictionary, Houghton Mifflin Company, Boston, p. 1116, 1994.*

(List continued on next page.)

Primary Examiner—Hankyel T. Park
(74) Attorney, Agent, or Firm—Iver P. Cooper

(57) ABSTRACT

A method of immunization, and compositions therefor, are provided for substantially preventing or reducing the symptoms of at least one infectious disease and at least one chronic immune mediated disorder. An immunogenic challenge which supplements the normal childhood immunization schedule can help ensure the proper maturation of the immune system and prevent the development of chronic immune mediated disorders, such as immune-mediated diabetes or SLE.

113 Claims, 3 Drawing Sheets

OTHER PUBLICATIONS

Pediatric Infectious Diseases Journal, 18(3):217–22, 1999.*
Boumpas et al., Annals of Internal Medicine, 123(1):42–53, Jul. 1995.*
Benveniste, pp. 346–364, and Lagrange et al., pp. 465–502, in Immunology, Bach et al., ed., John Wiley & Sons, New York, 1982.*
Adorini et al. Trends in Immunology 18(5): 209–211, 1997.*
Miller et al. The Biological and Clinical Basis of Infectious Diseases, Chapter 3, pp. 15–28, 1997.*
John Brit. Med. Journal. 289:881–882, 1984.*
Halsey et al. Bulletin of the World Health Organization 63(6): 1151–1169, 1985.*
Dengrove et al. Pediatric Research 20(8): 725–739, 1986.*
Madore et al. Pediatrics 85(3): 331–337, 1990.*
Hayes, Science 260: 1279–1286, 1993.*
Zuckerman et al. J. Hepatol. 22(Suppl. 1): 97–100, 1995.*
Spigland et al. Pediatrics , 812–821, 1960.*
Vautier, et al., Acute Sero–Positive Rheumatoid Arthritis Occurring after Hepatitis Vaccination, British Journal of Rheumatology, vol. 33, p. 991, 1994.
Kelton, et al., Vaccination–Associated Relapse of Immune Thrombocytopenia, JAMA, vol. 245, No. 4, pp. 369–371, Jan. 23–30, 1981.
Fletcher, et al., Rare Disease, Clinical Epidemiology– the essentials, chapter 10, pp. 168–173, 1982.
Aho, et al., Transient Appearance of the Rheumatoid Factor in Connection with Prophylactic Vaccinations, ACTA Pathol. Microbial Scan., vol. 46, p. 478–479, 1962.
Schattner, et al., Poliovaccines and the Course of Systemic Lupus Erythematosus– a Retrospective Study of 73 Patients, Vaccine, vol. 10, Issue 2, pp. 98–100, 1992.
Britton, et al., Possible Interactions Between Rabies Vaccination and a Progressive Degenerative CNS Disease, Arch Neurol., vol. 35, p. 693, Oct. 1978.
Toro, et al., Neuroparalytic Accidents of Antirabies Vaccination with Suckling Mouse Brain Vaccine, Arch Neurol., vol. 34, pp. 700, Nov. 1977.
Louie, et al., Clinical and Antibody Responses After Influenza Immunization in Systemic Lupus Erythematosus, Annals of Internal Medicine, vol. 88, No. 6, pp. 790–792, Jun. 1978.
Ristow, et al., Influenza Vaccination of Patients with Systemic Lupus Erythematosus, Annals of Internal Medicine, vol. 88, pp. 786–789, 1978.
Williams, et al., Infleunze Immunization in Systemic Lupus Erythematosus, Annals of Internal Medicine, vol. 88, No. 6, pp. 729–734, Jun. 1978.
Peeler, et al., Intensive Immunization of Man, Annals of Internal Medicine, vol. 63, No. 1, pp. 44–57, Jul. 1965.
White, et al., Repeated Immunization: Possible Adverse Effects, Annals of Internal Medicine, vol. 81, pp. 594–600, 1974.
Sinaniotis, et al., Diabetes Mellitus After Mumps Vaccination, Archives of Diseases of Childhood, vol. 50(9), p. 749, 1975.
Sultz, et al., Is Mumps Virus an Etiologic Factor in Juvenile Diabetes Mellitus?, The Journal of Pediatrics, vol. 86 No. 4, pp. 654–656, Apr. 1975.
Champsaur, et al., Virologic, Immunologic, and Genetic Factors in Insulin–Dependent Diabetes Mellitus, The Journal of Pediatrics, vol. 100, No. 1, pp. 15–20, Jan. 1982.

Fescharek, et al., Measles–Mumps Vaccination in the FRG: an Empirical Analysis After 14 Years of Use. II. Tolerability and Analysis of Spontaneously Reported Side Effects, Vaccine, vol. 8, pp. 446–456, Oct. 1990.
Helmke, et al., Islet Cell Antibodies and the Development of Diabetes Mellitus in Relation to Mumps Infection and Mumps Vaccination, Diabetologia, vol. 29, pp. 30–33, 1986.
Vaandrager, et al., Islet Cell Antibodies, Mumps Infection and Mumps Vaccination, Diabetologia, vol. 29, p. 406, 1986.
Bodansky, et al., Does Exposure to Rubella Virus Generate Endocrine Autoimmunity?, Diabetic Medicine, vol. 7, pp. 611–614, 1990.
Blom, et al., The Swedish Childhood Diabetes Study, Diabetologia, vol. 34, pp. 176–181, 1991.
Dahlquist, et al., The Swedish Childhood Diabetes Study—a Multivariate Analysis of Risk Determinants for Diabetes in Different Age Groups, Diabetologia, vol. 34, pp. 757–762, 1991.
Hoover, Robert No., Bacillus Calmette–Guerin Vaccination and Cancer Prevention: A Critical Review of the Human Experience, Cancer Research, vol. 36, pp. 652–654, Feb. 1976.
Clemens, et al., BCG Prophylaxis Against Cancer: Methodological Evaluation of a Continuing Controversy, J. Chron. Dis., vol. 37, No. 1, pp. 45–54, 1984.
Grange, et al., BCG Vaccination and Cancer, Tubercle, vol. 71, pp. 61–64, 1990.
Engleman, et al., Treatment of NZB/NZW $F_1$ Hybrid Mice with Mycobacterium Bovis Strain BCG or Type II Interferon Preparations Accelerates Autoimmune Disease, Arthritis and Rheumatism, vol. 24, No. 11, Nov. 1981.
Klemparskaya, N., Autohaemolysin–Producing Cells in Mice Injected with Bacterial Vaccines, Immunology, vol. 25, pp. 11–15, 1973.
Onica, et al., Autoantibodies Detected in Rabbits Hyperimmunized with Group A, C, and G Streptococcal Vaccines, Infection and Immunity, vol. 18, pp. 624–628, 1977.
Colling, et al., Association of Bacterial Carbohydrate–Specific Cold Agglutinin Antibody Production with Immunization by Group C, Group B Type III, and Streptococcus pneumoniae Type XIV Streptococcal Vaccines, Infection and Immunity, vol. 41, No. 1, pp. 205–213, Jul. 1983.
Levine, et al., Exacerbation and Transformation of Allergic Encephalomyelitis by Pertussis Vaccine, PSEBM, vol. 112, pp. 115–118, 1966.
Caspary, E.A., Effect of Live Attenuated Vaccines of the Course of Experimental Allergic Encephalomyelitis, Eur. Neurol., vol. 16, pp. 176–180, 1977.
Ronneberger, et al., Allergic Encephalomyelitis in Rats— Toxicity Assay for Pertussis Vaccines, Arch. Toxicol., Suppl. 4, pp. 179–183, 1980.
Kallen, et al., Effect of Bordetella Pertussis Vaccine on Experimental Autoimmune Encephalomyelitis in Rats, Int. Archs Allergy Appl. Immun., vol. 80, pp. 95–99, 1986.
Twarog, et al., The Adjuvant Effect of Pertussis Vaccine in Experimental Thyroiditis of the Rat, P.S.E.B.M., vol. 130, pp. 434–439, 1968.
Rudofsky, U.H., Studies on the Pathogenesis of Experimental Autoimmune Renal Tubulointerstitial Disease in Guinea–Pigs, Clin. J. Immunol., vol. 25, pp. 455–461, 1976.
Helmke, et al., Response from the Authors, Diabetologia, vol. 29, p. 407, 1986.

Rosenthal, et al., *Cancer Precursors and their Control by Stimulation of the Immune System*, Biomedicine & Pharmacotherapy, vol. 38, pp. 429–433, 1984.

Rosenthal, et al., *Cancer Precursors and their Control by BCG*, Develop. Biol. Standard, vol. 58, pp. 401–416, 1986.

Hyoty, et al., *Decline of Mumps Antibodies in Type 1 (insulin–dependent) Diabetic Children and a Plateau in the Rising Incidence of Type 1 Diabetes After Introduction of the Mumps–Measles–Rubella Vaccine in Finland*, Diabetologia, vol. 36, pp. 1303–1308, 1993.

Ferreri et al , Curr. Ther. Res. 52(3) 1992 (Abstract) pp. 493–497.*

Ferreri et al. G. Mal. Infett, Parass. H 113(2) (1990) 150–151 (Abstract).*

Baraff et al, "Immunologic Response to Early and Routine DTP Immunization in Infants", *Pediatrics*, 73:37–42 (Jan. 1984).

Barrett et al, "Multiple Antigen for Immunization Against Poliomyelitis, Diphtheria, Pertussis, and Tetanus" *Jama*, 167:1103–1107 (Jun. 28, 1958).

Barrett et al, "Multiple Antigen Immunization of Infants Against Poliomyelitis, Diphtheria, Pertussis, and Tetanus", *Pediatrics*, pp. 720–736 (Nov. 1962).

Blom, et al., "The Swedish childhood diabetes study: Vaccinations and Infections as risk determinants for diabetes in childhood", *Diabetologia*, 34:176–181 (1991).

Classen, et al., Evidence That Cyclosporine Treatment During Pregnancy Predisposes offspring to Develop Autoantibodies, Transplantation, vol. 51, No. 5, pp. 1052–1057, May 1991.

Dengrove et al, IgG and IgG Subclass Specific Antibody Responses to Diphtheria and Tetanus Toxoids in Newborns and Infants Given DTP Immunization, Pediatric Research, vol. 20, No. 8, pp. 735–739, 1986.

Elias et al, Vaccination against autoimmune mouse diabetes with a T–cell epitope of the human 65–kDa heat shock protein, Natl. Acad. Sci. USA, vol. 88, pp. 3088–3091, Apr. 1991.

Elias et al, Inductin and therapy of autoimmune diabetes in the non–obese diabetic (NOD/Lt) mouse by a 65–kDa heat shock protein, Proc. Natl. Acad. Sci. USA, vol. 87, pp. 1576–1580, Feb. 1990.

Fagan McInerney, et al., Prevention of Insulitis and Diabetes Onset by Treatment With Complete Freund's Adjuvant in NOD Mice, Diabetes, vol. 40, pp. 715–725, Jun. 1991.

General Recommendations on Immunization, JAMA, vol. 262 No. 1, pp. 22–26, Jul. 7, 1989 (from the CDC).

General Recommendations on Immunization, JAMA, vol. 262, No. 3, pp. 339–340, Jul. 21, 1989 (from the CDC).

Grange et al, BCG vaccination and cancer, Tubercle, vol. 71, pp. 61–64.

Green et al, Incidence of childhood–onset insulin dependent diabetes mellitus: the Eurodiab Ace study, The Lancet, vol. 339, pp. 905–909, Apr. 11, 1992.

Halsey et al, The efficacy of DPT and oral poliomyelitis immunization schedules initiated from birth to 12 weeks of age, Bulletin of the World Health Organization, vol. 63 (6), pp. 1151–1169, 1985.

Harada, et al., Prevention of overt diabetes and insulitis in NOD mice by a single BCG vaccination, Diabetes Research and Clinical Practice, vol. 8, pp. 85–89, 1990.

Huang et al, Pertussigen Treatment Retards, But Fails To Prevent, The Development of Type I, Insulin–Dependent Diabetes Mellitus (IDDM) In NOD Mice, Autoimmunity, vol. 9, pp. 311–317, 1991.

Huang et al, The Effect of Pertussis Vaccine on the Insulin–Dependent Diabetes Induced by Streptozocin in Mice, Pediatric Research, vol. 18, No. 2, pp. 221–226, 1984.

Imamura et al, Intrapericardial OK–432 Instillation for the Management of Malignant Pericardial Effusion, Cancer, vol. 68 No. 3, pp. 259–263, Jul. 15, 1991.

John, T. Jacob, Immune response of neonates to oral poliomyelitis vaccine, British Medical Journal, vol. 289, pp. 881, Oct. 6, 1984.

Kolb et al, Analysis of 22 Immunomodulatory Substances for Efficacy in Low–Dose Streptozotocino–Induced Diabetes, Diabetes Research, vol. 6, pp. 21–27, 1987.

Krowlewski et al, Epidimiologic Approach to The Etiology of Type I Diabetes Mellitus and its Complications, The New England Journal of Medicine, vol. 317 No. 22, pp. 1390–1398, Nov. 26, 1987.

Madore et al, Safety and Immunologic Response to Haemophilus Influenzae Type b Oligosaccharide–CRM Conjugate Vaccine in 1– to 6–Month–Old Infants, Pediatrics, vol. 85 No. 3, pp. 331–337, Mar. 1990.

Mukai et al, Combination Therapy of Local Administration of OK–432 and Radiation for Esophageal Cancer, Int. J. Radiation Oncology Biol. Phys., vol. 22 No. 5, pp. 1047–1050, 1992.

Ogita et al, OK–432 Therapy for Unresectable Lymphangiomas in Children, Journal of Pediatric Surgery, vol. 26 No. 3, pp. 263–270, Mar. 1991.

Oldstone, et al., Viruses as Therapeutic Agents, J. Exp. Med., vol. 171, pp. 2091–2100, Jun. 1990.

Oldstone, Michael B.A., Prevention of Type I Diabetes in Nonobase Diabetic Mice by Virus Infection, Science, vol. 239, pp. 500–502, Jan. 29, 1988.

Pabst et al, Effect of breast–feeding on antibody response to conjugate vaccine, The Lancet, vol. 336, pp. 269–270, Aug. 4, 1990.

Pearce et al, Studies of Concanavalin A in Nonobese Diabetic Mice. I. Prevention of Insulin–Dependent Diabetes, The Journal of Pharmacology Experiment Therapeutics, vol. 258 No. 2, pp. 710–715, 1991.

Perkins et al, Serological Response of Infants To Poliomyelitis Vaccine, British Medical Journal, pp. 68–71, Jul. 12, 1958.

Provenzano et al, Immunization and Antibody Response in the Newborn Infant, The New England Journal of Medicine, vol. 273, No. 18, pp. 959–965, Oct. 28, 1965.

Sadelain, et al., Prevention of Type I Diabetes in NOD Mice by Adjuvant Immunotherapy, Diabetes, vol. 39, pp. 583–589, May 1990.

Satoh et al, Treatment With Streptococcal Preparation (OK–432) Suppresses Anti–Inlet Autoimmunity and Prevents Diabetes in BB Rats, Diabetes, vol. 37, pp. 1188–1194, Sep. 1988.

Satoh et al, Recombinant Human Tumor Necrosis Factor $\alpha$ Suppresses Autoimmune Diabetes in Nonobese Diabetic Mice, Rapid Publication, vol. 84, pp. 1345–1348, Oct. 1989.

Schwimmbeck, et al., Abrogation of Diabetes in BB Rats by Acute Virus Infection, Association of Viral–Lymphocyte Interactions, The Journal of Immunology, vol. 140, No. 10, pp. 3394–3400, May 15, 1988.

Seino et al, Inhibition of autoimmune diabetes in NOD mice with serum form streptococcal preparation (OK–432)–injected mice, Clin. exp. Immunol., vol. 86, pp. 413–418, 1991.

Shintani, et al., Mechanism of Action of A Streptococcal Preparation (OK–432) in Prevention of Autoimmune Diabetes in NOD Mice, The Journal of Immunology, vol. 144, No. 1, pp. 136–141, Jan. 1, 1990.

Simultaneous Administration of Multiple Vaccines, Active Immunization, pp. 16–19.

Spigland et al, Immunization of Infants With Formalinized Poliomyelitis Vaccine (Salk Type), Pediatrics, vol. 25, pp. 812–821, May 1960.

Toyota et al, Islet Activating Protein (IAP) Derived from the Culture Supernatant Fluid of Bordetella Pertussis: Effect on Spontaneous Diabetic Rats, Diabetologia, vol. 14, pp. 319–323.

Toyota et al, Streptococcal Preparation (OK–432) Inhibits Development of Type I Diabetes in NOD Mice, Diabetes, vol. 35, pp. 496–499, Apr. 1986.

Vagede et al., Vaccine Technology, vol. 23, pp. 628–643.

Wheeley et al, Hepatitis B Vaccine in the Prevention of Perinatally Transmitted Hepatitis B Virus Infection: Final Report on a West Midland Pilot Study, Journal of Medical Virology, vol. 30, pp. 113–116, 1990.

Herold, Kevan C et al, Prevention of Autoimm. Diab. 2/ Nonactivity Anti–CD3 Monoclonal Antibody , Diabetes, vol. 41, pp. 385–391 Infectious Disease Ch. 3 Prevention of Infection pp. 21–24 Immunization Procedures for Adults, Mar. 1992.

Mihara, Masahiko et al, Autoimmune Kidney Disease in MRL/1Pr Mice Inhibited by OK–132; II. Effect of Indomethacin, *J. Pharmacobio–Dyn.*, 15: 255–259, 1992.

Mihara, M. et al., Autoimmune Kidney Disease in MRL/ Mp–Ipr mice inhibited by Ok–432, a streptococcal preparation, *Clin. exp. Immunol.* 78:102–107, 1989.

Guberski, D.L. et al., Induction of Type I Diabetes by Kilham's Rat Virus in Diabetes–Resistant BB/Wor Rats, *Science*, 25:1010–1013, Nov. 15, 1991.

Luh, Kwen–Tay, et al., Comparison of OK–432 and Mitomycin C Pleurodesis for Malignant Pleural Effusion Caused by Lung Cancer, *Cancer*, 69:674–679, Feb. 1, 1992.

Hems, Gordon et al., B.C.G. and Leukemia, *The Lancet*, p. 183, Jan. 23, 1971.

Salonen, Tuula et al., Risk Indicators in Childhood Malignancies, *Int. J. Cancer*, 15:941–946, 1975.

Infectious Disease, Chapter 3, Prevention of Infection, Immunization Procedures for Adults, pp. 21–24.

Shinoda, M. et al., Treatment of advanced renal cell carcinoma with interferon alpha and OK–432 (streptococcal preparation), *Acta Urologica Japonica*, 38:1299–304, Nov. 1992.

Aharon–Maor, et al., *The Good, the Bad and the Ugly of Vaccination*, IMAJ, vol. 2, pp. 225–227, Mar. 2000.

Aho, et al., *Rheumatoid Factor and Immuno–Conglutinin Responses Following Various Vaccination*, P.S.E.B.M., vol. 124, pp. 229–233, 1967.

ALM, et al., *Early BCG vaccination and development of atopy*, The Lancet, vol. 350, pp. 400–403, Aug. 9, 1997.

Arnqvist, et al., *Difficulties in Classifying Diabetes at Presentation in the Young Adult*, Diabetic Medicine, vol. 10, pp. 606–613, Jan. 1993.

Ayvazian, et al., *Disseminated Lupus Erythematosus Occuring Among Student Nurses*, The New England Journal of Medicine, vol. 239, No. 16, pp. 565–570, Oct. 14, 1948.

Bamford, et al., *Swine Influenza Vaccination in Patients with Multiple Sclerosis*, Arch. Neurol., vol. 35, pp. 242–243, Apr. 1978.

Bijkerk, H., *Mass Vaccination in the Netherlands*, International Symposium on Vaccination Against Communicable Diseases, Monaco, vol. 22, pp. 271–276, 1973.

Booy, et al., *Efficacy of Haemophilus Influenzae Type b conjugate vaccine PRP–T*, Lancet, vol. 344, Abstract, Aug. 6, 1994.

Brewster, D., *The epidemiology of Haemophilus influenzae invasive disease in Scotland prior to immunisation*, Health Bull (EDINB), vol. 51(6), Abstract, Nov. 1993.

Brodman, et al., *Influenzal Vaccine Response in Systemic Lupus Erythematosus*, Annals of Internal Medicine, vol. 88, pp. 735–740, 1978.

Bruno, et al., *Comparison of Incidence of Insulin–dependent Diabetes Mellitus in Children and Young Adults in the Province of Turin, Italy, 1984–91*, Diabetic Medicine, vol. 14, pp. 964–969, 1997.

Caspary, et al., *Antibody studies in multiple sclerosis and experimental 'allergic' encephalomyelitis*, J. Neurol. Neurosurg. Psychiat., vol. 27, pp. 25–28, 1964.

Chaleomchan, et al., *Anticardiolipin antibodies in patients with rabies vaccination induced neurological complications and other neurological diseases*, Journal of the Neurological Sciences, vol. 96, pp. 143–151, 1990.

Chen, et al., *Vaccine Safety*, Lancet, vol. 352, Abstract, 1998.

Chen, et al., *Vaccine Safety Datalink Project: A New Tool for Improving Vaccine Safety Monitoring in the United States*, Pediatrics, vol. 99, No. 6, pp. 765–773, Jun. 6, 1997.

Classen, John Barthelow, *Data links vaccines to risk of Insulin Dependent Diabetes (IDDM)*, Drug Safety, vol. 21, Abstract, 1999.

Classen, John Barthelow, *Diabetes Epidemic Follow Hepatitis B Immunization Program*, New Zealand Medical Journal, vol. 190, Abstract, May 24, 1996.

Croke, et al., *Occurrence of Severe Destructive Lyme Arthritis in Hamsters Vaccinated with Outer Surface Protein A and Challenged with Borrelia burgdorferi*, Infection and Immunity, vol. 68, No. 2, pp. 658–663, Feb. 2000.

D'Amelio, et al., *Comparative Analysis of Immunological Responses to Oral (Ty21a) and Parenteral (TAB) Typhoid Vaccines*, Infection and Immunity, vol. 56, No. 10, pp. 2731–2735, Oct. 1988.

Del Giudice, et al., *Priming to Heat Shock Proteins in Infants Vaccinated against Pertussis*, The Journal of Immunology, vol .150, No. 5, pp. 2025–2032, Mar. 1, 1993.

DeStefano, et al., *Timing of Hepatitis B Vaccination and Risk of Insulin–Dependent Diabetes Mellitus*, Pharmacoepidemiology and Drug Safety, vol. 6, suppl. 2, Abstract, 1997.

Hibbs, et al, *Internet Web Page Perceptions of Vaccine Pharmacoepidemiology Research: An Analysis of Vaccine Safety Concerns*, Pharmacoepidemiology and Drug Safety, vol. 6, suppl. 2, Abstract, 1997.

Dokheel, Tomadher M., *An Epidemic of Childhood Diabetes in the United States?*, Diabetes Care, vol. 16, No. 12, pp. 1606–1611, Dec. 1993.

Drykoningen, et al., *The incidence of male childhood Type 1 (insulin–dependent) diabetes mellitus is rising rapidly in The Netherlands*, Diabetologia, vol. 35, pp. 139–142, 1992.

Eskola, et al., *A Randomized, Prospective Field Trial of a Conjugate Vaccine in the Protection of Infants and Young Children Against Invasive Haemophilus Influenzae Type b Disease*, The New England Journal of Medicine, vol. 323, No. 20, pp. 1381–1387, Nov. 15, 1990.

Espmark, et al., *Smallpox Vaccination Before the Age of Three Months: Evaluation of Safety*, International Symposium on Smallpox Vaccine, Bilthoven, vol. 19, pp. 243–247, 1972.

Eurodiab Ace Study Group, *Variation and trends in Incidence of childhood diabetes in Europe*, The Lancet, vol. 355, pp. 873–876, Mar. 11, 2000.

Eurodiab Substudy 2 Study Group, *Infections and vaccination as risk factors for childhood Type 1 (insulin–dependent) diabetes mellitus: a multicentre case–control investigation*, Diabetologia, vol. 43, pp. 47–53, 2000.

Gardner, et al., *Rising incidence of insulin dependent diabetes in children aged under 5 years in Oxford region: time trend analysis*, BMJ, vol. 315, pp. 713–717, Sep. 1997.

Goday, et al., *Incidence of Type 1 (insulin–dependent) diabetes mellitus in Catalonia, Spain*, Diabetologia, vol. 35, pp. 267–271, 1992.

Gorham, et al., *Incidence of Insulin–dependent Diabetes Mellitus in Young Adults: Experience of 1,587,630 US Navy Enlisted Personnel*, American Journal of Epidemiology, vol. 138, No. 11, pp. 984–987, 1993.

Graves, et al., *Lack of Association Between Early Childhood Immunizations and β–Cell Autoimmunity*, Diabetes Care, vol. 22, No. 10, pp. 1694–1697, Oct. 1999.

Griffith, A.H., *Achievements in Europe*, International Symposium on Vaccination Against Communicable Diseases, Monaco, vol. 22, pp. 13–24, 1973.

Hackett, et al., *Transient Appearance of "Autoimmune" Antibodies During Prophylactic Immunization*, J. Immunology, vol. 85, pp. 533–538, 1960.

Heijbel, et al., *Cumulative Incidence of Childhood–Onset IDDM is Unaffected by Pertussis Immunization*, Diabetes Care, vol. 20, No. 2, pp. 173–175, Feb. 1997.

Hemachudha, et al., *Myelin Basic Protein as an Encephalitogen in Encephalomyelitis and Polyneuritis Following Rabies Vaccination*, The New England Journal of Medicine, vol. 316, No. 7, pp. 369–374, Feb. 12, 1987.

Herron, et al., *Influenza Vaccination in Patients with Rheumatic Diseases*, JAMA, vol. 242, No. 1, pp. 53–56, Jul. 6, 1979.

Hiltunen, et al., *Immunisation and Type 1 Diabetes Mellitus*, Drug Safety, vol. 20, No. 3, pp. 207–212, 1999.

Huang, et al., *Pertussis vaccine inhibits immune insulitis induced with streptozotocin*, Clin. Exp. Immunol., vol. 48, pp. 375–380, 1982.

Huang, et al., *The Relationship Between Influenza Vaccine–Induced Specific Antibody Responses and Vaccine–Induced Nonspecific Autoantibody Responses in Healthy Older Women*, Journal of Gerontology: Medical Sciences, vol. 47, No. 2, pp. M50–M55, 1992.

Huovila, Riitta, *Adverse Reactions in Children Vaccinated with DPT and Pertussis Vaccine*, Acta Paediatr Scand, vol. 298, Suppl. 26–29, pp. 26–29, 1982.

Huovila, R., *Agglutinins in Children Vaccinated with the DPT Vaccines used in Finland, Serotypes of Bordetella Pertussis Strains Isolated During Whooping Cough Epidemics in 1976–1977 and Whooping Cough Attack Rate in Children in the Epidemic Areas*, Acta Paediatr Scand, vol. 298, pp. 21–25, 1982.

Jefferson, et al., *No evidence that vaccines cause insulin dependent diabetes mellitus*, Journal of Epidemiology & Community Health, vol. 52, No. 10, pp. 674–675, Oct. 1998.

Jefferson, Tom, *Vaccination and its adverse effects: real or perceived*, BMJ, vol. 317, pp. 159–160, Jul. 18, 1998.

Joner, et al., *Increasing incidence of diabetes mellitus in Norwegian children 0–14 years of age 1973–1982*, Diabetologia, vol. 32, pp. 79–83, 1989.

Joner, et al., *The incidence of Type 1 (insulin–dependent) diabetes mellitus 15–29 years in Norway 1978–1982*, Diabetologia, vol. 34, pp. 271–274, 1991.

Karsh, et al., *Immunization of Patients with Sjögren's Syndrome with Pneumococcal Polysaccharide Vaccine*, Arthritis and Rheumatism, vol. 23, No. 11, pp. 1294–1298, Nov. 1980.

Karvonen, et al., *Association between type 1 diabetes and Haemophilus influenzae type b vaccination: birth cohort study*, BMJ, vol. 318, pp. 1169–1172, May 1, 1999.

Katada, et al., *Spontaneous Recovery from Streptozotocin–Induced Diabetes in Rats Pretreated with Pertussis Vaccine of Hydrocortisone*, Diabetologia, vol. 13, pp. 521–525, 1977.

Keuter, E.J.W., *Significance of Constitution, Especially the Status Dysraphicus in the Genesis of Postvaccinal encephalitis*, Predisposition To Postvaccinial Encephalitis, Chapter 1, pp. 1–9, 1960.

Kline, et al., *Optic Neuritis and Myelitis Following Rubella Vaccination*, Arch Neurol., vol. 39, pp. 443–444, Jul. 1982.

Klippel, et al., *A Controlled Study of Pneumococcal Polysaccharide Vaccine in Systemic Lupus Erythematosus*, Arthritis and Rheumatism, vol. 22, No. 12, pp. 1321–1325, Dec. 1979.

Kurland, et al., *Lack of Association of Swine Flu Vaccine and Rheumatoid Arthritis*, Mayo Clin Proc., vol. 59, pp. 816–821, 1984.

Kurland, et al., *Swine Flu Vaccine and Multiple Sclerosis*, JAMA, vol. 251, No. 20, pp. 2672–2675, May 25, 1984.

Libman, et al., *Was There an Epidemic of Diabetes in Nonwhite Adolescents in Allegheny County, Pennsylvania?*, Diabetes Care, vol. 21, No. 8, pp. 1278–1281, Aug. 1998.

Lindberg, et al., *Previous Exposure to Measles, Mumps, and Rubella—but Not Vaccination During Adolescence—Correlates to the Prevalence of Pancreatic and Thyroid Autoantibodies*, Pediatrics, vol. 104, No. 1, pp. 1–5, Jul. 1999.

Lipnick, et al., *Pneumococcal Immunization in Patients with Systemic Lupus Erythematosus Treated with Immunosuppressives*, The Journal of Rheumatology, vol. 12, pp. 1118–1121, 1985.

Lundbeck, H., *Vaccination Programmes in Sweden*, International Symposium on Vaccination Against Communicable Diseases, Monaco, vol. 22, pp. 279–286, 1973.

Moodie, et al., *Concurrent BCG and Smallpox Vaccination in Newborn Babies*, Tubercle, Lond., vol. 43, pp. 155–160, 1962.

Muntoni, et al., *High Incidence Rate of IDDM in Sardinia*, Diabetes Care, vol. 15, No. 10, pp. 1317–1322, Oct. 1992.

Myers, et al., *Swince Influenza Virus Vaccination in Patients with Multiple Sclerosis*, The Journal of Infectious Disease, vol. 136, supplement, pp. S546–S562, Dec. 1977.

Nyström, et al., *Risk of Developing Insulin–Dependent Diabetes Mellitus (IDDM) before 35 Years of Age: Indications of Climatological Determinants for Age at Onset*, International Journal of Epidemiology, vol. 21, No. 2, pp. 352–358, 1992.

Onkamo, et al., *Worldwide increase in incidence of Type 1 diabetes—the analysis of the data on published incidence trends*, Diabetologia, vol. 42, pp. 1395–1403, 1999.

Parent, et al., *Bacille Calmette–Guérin Vaccination and Incidence of IDDM in Montreal, Canada*, Diabetes Cares, vol. 20, No. 5, pp. 767–772, May 1997.

Peltola, et al., *Rapid disappearance of Haemophilus influenzae type b meningitis after routine childhool immunisation with conjugate vaccines*, vol. 340, pp. 592–594, 1992.

Pettersson, Tor, *Immunization and Arthritis*, Scand J. Rheumatology, vol. 1, pp. 61–64, 1972.

Polak, M.F., *Complications of Smallpox Vaccination in the Netherlands, 1959–1970*, International Symposium on Smallpox Vaccine, Bilthoven, vol. 19, pp. 235–242, 1972.

Poser, et al., *Late Onset of Guillain—Barré Syndrome*, Journal of Neuroimmunology, vol. 3, pp. 27–41, 1982.

Rami, et al., *Risk factors for type 1 diabetes mellitus in children in Austria*, Eur. J. Pediatr., vol. 158, pp. 362–366, 1999.

Ramiya, et al., *Immunization Therapies in the Prevention of Diabetes*, Journal of Autoimmunity, vol. 10, pp. 287–292, 1997.

Ramiya, et al., *Antigen Based Therapies to Prevent Diabetes in NOD Mice*, Journal of Autoimmunity, vol. 9, pp. 349–356, 1996.

Romanus, et al., *Pertussis in Sweden after the cessation of general immunization in 1979*, The Pediatr. Infect Dis. J., vol. 6, pp. 364–371, 1987.

Rose, Noel R. ,*Immunologic Hazards Associated with Vaccination of Humans*, Journal of Autoimmunity, vol. 14, pp. 11–13, 2000.

Scott, et al., *Temporal Variation in Incidence of IDDM in Canterbury, New Zealand*, Diabetes Care, vol. 15, No. 7, pp. 895–899, Jul. 1992.

Shapiro, et al., *The Protective Efficacy of Haemophilus by Polysaccharide Vaccine*, JAMA, vol. 260, No. 10, pp. 1419–1422, Sep. 9, 1998.

Shirakawa, et al., *The Inverse Association Between Tuberculin Responses and Atopic Disorder*, Science, vol. 275, pp. 77–79, Jan. 3, 1997.

Shoenfeld, et al., *Vaccination as an additional player in the mosaic of autoimmunity*, Clinical and Experimental Rheumatology, vol. 18, pp. 181–184, 2000.

Shoenfeld, et al., *Vaccination and Autoimmunity—'vaccinosis': A Dangerous Liaison?*, Journal of Autoimmunity, vol. 14, pp. 1–10, 2000.

Sibley, et al., *Influenza Vaccination in Patients with Multiple Sclerosis*, JAMA, vol. 236, No. 17, pp. 1965–1966, Oct. 25, 1976.

Stephenson, Joan Ph.D., *Vaccines Pose No Diabetes, Bowel Disease Risk*, JAMA, vol. 284, No. 18, pp. 2307–2308, Nov. 8, 2000.

Stratton, et al., *Adverse Events Associated with Childhoold Vaccines Other Than Pertusis and Rubella*, JAMA, vol. 271, No. 20, pp. 1602–1604, May 25, 1994.

Taylor, et al., *Autism and measles, mumps, and rubella vaccine: no epidemiological evidence for a causal association*, The Lancet, vol. 353, pp. 2026–2029, Jun. 12, 1999.

Tonooka, et al., *Lymphoid Thyroiditis Following Immunization with Group A Streptococcal Vaccine*, American Journal of Pathology, vol. 92, No. 3, pp. 681–687, Sep. 1978.

Tuomilehto, et al., *Increase in Incidence of Insulin–Dependent Diabetes Mellitus among Children in Finland*, International Journal of Epidemiology, vol. 24, No. 5, pp. 984–992, 1995.

Tuomilehto, et al., *Record–high incidence of Type 1 (insulin–dependent) diabetes mellitus in Finnish children*, Diabetologia, vol. 42, pp. 655–660, 1999.

Vandewalle, et al., *Epidemiology, Clinical Aspects, and Biology of IDDM Patients Under Age 40 Years*, Diabetes Care, vol. 20, No. 10, pp. 1556–1561, Oct. 1997.

Welch, et al., *Increased frequency of rheumatoid factor precursor B lymphocytes after immunization of normal adults with tetanus toxoid*, Clin. Exp. Immunol., vol. 51, pp. 299–304, 1983.

Yagi, et al., *Possible Mechanism of the Preventive Effect of BCG against Diabetes Mellitus in NOD Mouse*, Cellular Immunology, vol. 138, pp. 130–141, 1991.

Yagi, et al., *Possible Mechanism of the Preventive Effect of BCG against Diabetes Mellitus in NOD Mouse*, Cellular Immunology, vol. 138, pp. 142–149, 1991.

Zhao, et al., *Incidence of childhood–onset Type 1 diabetes mellitus in Devon and Cornwall, England, 1975–1996*, Diabetic Medicine, vol. 16, pp. 1030–1035, 1999.

Classen, John Barthelow, M.D., M.B.A., *The Timing of Immunization Affects the Development of Diabetes in Rodents*, Autoimmunity, vol. 24, pp. 137–145, 1996.

Classen, John Barthelow, *Cyclosporine Induced Autoimmunity in Newborns Prevented by Early Immunization*, Autoimmunity, vol. 27, pp. 135–139, 1998.

Classen, et al., *Immunization in the First Month of Life may Explain Decline in Incidence of IDDM in The Netherlands*, Autoimmunity, vol. 31, pp. 43–45, 1999.

Classen, J. Barthelow, *Vaccines modulate IDDM*, Diabetologia, vol. 39, pp. 1–2, 1996.

Classen, David C., *The Timing of Pediatric Immunization and the Risk of Insulin–Dependent Diabetes Mellitus*, Infectious Diseases in Clinical Practice, vol. 6, pp. 449–454, 1997.

Classen, John Barthelow, et al., *Vertically Transmitted Enteroviruses and the Benefits of Neonatal Immunization*, Diabetes Care, vol. 22, No. 10, pp. 1760–1761, Oct. 1999.

Classen, John Barthelow, et al., *Incidence of Type 1 Diabetes in Germany is not Highter than Predicted*, Diabetes Care, vol. 20, No. 11, pp. 1799–1800, Nov. 1997.

Hotopf, et al., *Role of vaccinations as risk factors for ill health in veterans of the Gulf war: cross sectional study*, BMJ, vol. 320, pp. 1363–1367, May 20, 2000.

Hummel, MD, *Vaccines and the Appearance of Islet Cell Antibodies in Offspring of Diabetic Parents*, Diabetes Care, vol. 19, No. 12, pp. 1456–1457, Dec. 1996.

Kemp, et al., *Is Infant Immunization a Risk Factor for Childhood Asthma or Allergy?*, Epidemiology, vol. 8, No. 6, pp. 678–680, Nov. 1997.

Nilsson, et al., *A Randomized Controlled Trial of the Effect of Pertussis Vaccines on Atopic Disease*, Arch Pediatr Adolesc Med, vol. 152, pp. 734–738, Aug. 1998.

Nossal, et al., *Vaccination and Autoimmunity*, Journal of Autoimmunituy, vol. 14, pp. 13–15, 2000.

IVS Diabetes Workshop Panel, *Childhood immunizations and type 1 diabetes: summary of an Institute for Vaccine Safety Workshop*, Pediatr. Infect. Dis. J., vol. 18, No. 3, pp. 217–222, 1999.

Pundziute–LyckÅ, et al., *Infections and risk of Type 1 (insulin–dependent) diabetes mellitus in Lithuanian children*, Diabetologia, Abstract, vol. 43, issue 10, pp. 1229–1234, 2000.

Willis, et al., *Type 1 Diabetes Diagnosed before Age 20 in Canterbury, New Zealand: 1970–1999*, Abstract ADA Meeting, Jun. 2000.

Symmons, DPM, *Can immunisation trigger rheumatoid arthritis?*, Annals of the Rheumatic Diseases, vol. 52C127, pp. 843–844, 1993.

Ayvazian, L. Fred M.D., *Risks of Repeated Immunization*, Annals of Internal Medicine, vol. 82(4), pp. 589, 1975.

Bedford, Helen, *Studies of adverse effects of vaccination have duty to present full picture*, British Med. J., vol. 318, 1999.

Petousis–Harris, et al., *Hepatitis B vaccination and diabetes*, New Zealand Medical Journal, pp. 303–304, Aug. 13, 1999.

Poutasi, et al., *Immunization and Diabetes*, New Zealand Medical Journal (Letter), Oct. 11, 1996.

Poutasi, et al., *Immunization and diabetes*, New Zealand Medical Journal (Letter), Jul. 26, 1996.

Vasile Tudor, et al., Smallpox:Cholera, 1977 Abacus Press, Kent England, pp. 24–25.

McKinney, et al., *Incidence of diabetes in children*, BMJ, vol. 310, p. 1672, Jun. 24, 1995.

Myers, et al., *Swine–Influenza Vaccination in Multiple Sclerosis*, The New England Journal of Medicine, p. 1204, Nov. 18, 1976.

Dahlquist, et al., *The cumulative incidence of childhood diabetes mellitus in Sweden unaffected by BCG–vaccination*, Diabetologia, vol. 38, pp. 873–874, 1995.

Svendsen, A.J., et al., *Incidence of juvenile diabetes in Denmark*, Ugeskr Laeger, vol. 159, pp. 1257–1260, 1997.

Thivolet, C., et al., *Absence De Preuves Pour Un Lien Possible Entre Vaccination Contre L'Hépatitie Virale B Et Survenue D'un Diabete De Type 1*, Diabetes & Metabolism (Paris), vol. 25, pp. 441–445, 1999.

Kaur, et al., *Childhood vaccination should have been included in asthma study*, BMJ (Letter), vol. 317, p. 205, 1998.

Classen, et al., *Public should be told that vaccines may have long term adverse effects*, BMJ (Letter), vol. 318, pp. 193, 1999.

T.O. Jefferson, *Vaccines and their real or perceived adverse effects*, BMJ (Letter), vol. 318, p. 1487, 1999.

Elliman, David, *Vaccination and type 1 diabetes mellitus*, BMJ (Letter), vol. 318, pp. 1159–1160, 1999.

Classen, et al., *Association between type 1 diabetes and Hib vaccine*, BMJ (Letter), vol. 319, p. 1133, 1999.

Hotopf, Matthew, *Reanalysis of Gulf war vaccination data does not contradict findings*, British Medical Journal, vol. 321, p. 761, 2000.

Willis, et al., *Hepatitis B Immunisation and the Epidemiology of IDDM in Children and Adolescents aged 20 years in Canterbury, NZ*, Diabetes, vol. 46, suppl. 1:140A, 1997.

Scott, Russer, *Incidence of IDDM*, Personal Communication, South Island, New Zealand.

Robert Elliot, *Increase in IDDM incidence in 0–4.9 yr olds since HepB immunization introduced in 1987* Personal Communication, North Island, New Zealand.

Anonymous, *Diabetes on rise but less severe says study*, Herald (Auckland, New Zealand), p. A7, (Aug. 13, 1997).

Elias, Marilyn, USA Today, p. A1, Oct. 31, 2000.

Freundlich, Naomi, *A Vaccine Worse than the Disease?*, Business Week, pp. 93–95, Oct. 23, 2000.

Anonymous, *Evaluating New Supplement Labels*, The Johns Hopkins Medical Letter Health After 50, vol. 12, issue 2, Apr. 2000.

Classen Immunotherapies, Inc., *CDC Data Supports Causal Relationship between Vaccines and Diabetes. Diabetics Begin Seeking Legal Counsel Before Their Right to Compensation Expires. Vaccines Proven to be Largest Cause of Insulin Dependent Diabetes in Children*, Press Release (Toronto, Canada), Sep. 19, 2000.

Destefano, et al., *Hepatitis B and Hib Vaccines are not Associated With Increased Risk of Type 1 Diabetes*, 40th ICAAC, Presentation No.:1940.

Mansoor, David Osman, *Selective evidence was used to support link between immunisation and asthma*, BMJ, vol. 318, p. 193, Jan. 16, 1999.

Classen, J. Barthelow, Letter to Richard Smith Editorial Office British Medical Journal, Dec. 2, 1999.

*Borderline significance of relative risk for association between type 1 diabetes and Hib vaccine*, Responses to Articles, Oct. 22, 1999–Nov. 23, 1999, 7 pgs.

Simon, *Two vaccination studies offer contrast in interpretability*, British Med. J. (Letter), May 9, 1999, 6 pgs.

Classen, mark–up of proofs of Karvonen manuscript, Mar. 16, 1999, 17 pgs.

Graves, Patricia M., *Hemophilus Vaccine and Diabetes*, Diabetes Care (Letter), vol. 23, No. 6, p. 872.

Classen, John B., M.D., M.B.A., *Hemophilus Vaccine Associated With Increases Risk of Diabetes*, Diabetes Care (Letter), vol. 23, No. 6, p. 872.

Elliot, et al., *Childhood Vaccines and the Aetiology of Type 1 Diabetes*, Horm Res. vol. 50, p. 117, 1998.

Steele, Lea, *Prevalence and Patterns of Gulf War Illness in Kansas Veterans: Association of Symptons with Characteristics of Person, Place, and Time of Military Service*, American Journal of Epidemiology (Abstract), vol. 152, 991–1001, Nov. 15, 2000.

Willis, Jinny, British Medical Journal, Response, Dec. 6, 1999, 2 pgs.

Gomez, Jess, *LDS Hospital Study Finds Possible Link Between Timing of Common Pediatric Vaccines and Development of Type 1 Diabetes*, LDS Hospital (News Release), Oct. 22, 1997, 2 pgs.

Anonymous, *Diabetes and Vaccines*, Questions and Answers About Diabetes and Vaccines, http://www.cdc.gov/nip/vacsafe/concerns/diabetes/g&a.htm, Jan. 30, 2001.

Anonymous, CDC–Vaccine Safety Datalink (VSD) Project: http://www.cdc.gov/nip/vacsafe/vaccinessafety/publications/vsd.htm.

Anonymous, *Do DTP and Tetanus Vaccinations Cause Asthma?*, Dynamic Chiropractic, http://www.chiroweb.com/archives/18/07/05.html, vol. 18, No. 7, Mar. 20, 2000.

Anonymous, *Small Allergy Risk from pertussis Vaccine*, Reuter's Newsire Service (New York), Abstract, Aug. 13, 2000.

Feltbower, et al., *Rising incidence of childhood diabetes is seen at all ages in urban and rural settings in Yorkshire, United Kingdom*, Diabetologia, vol. 43, pp. 682–684, 2000.

Gunn, New Zealand Medical Journal, Letter, vol. 102, p. 3, 1989.

Willis, et al., *Hepatitis B Immunisation and the Epidemiology of IDDM in Children and Adolescents aged <20 years in Canterbury, NZ*, Diabetes, Letter, vol. 46, supl. 1, 1997.

Classen, British Medical Journal, Electrical Edition, Letter, 1999.

Anonymous, *French to Check Liaison Officers for Gulf Syndrome*, Reuter's Newsire Service (Paris), Sep. 14, 2000.

Classen, et al., *hemophilus vaccine and increased IDDM, casual relationship likely*, BMJ, vol. 319, 1999.

Destefano, et al., *Hepatitis B and Hib Vaccinations and Type 1 Diabetes*, 39th ICCAC Abstract #LB–11, 1999.

Quast, et al., *Vaccine Induced Mumps–Like Diseases*, Development Biol. Standards (Book), vol. 43, pp. 269–272, 1979.

Howson, et al., Adverse Effects of Pertussis and Rubella Vaccines, Washington, DC: National Academy Press (Book), pp. 158–161, 1991.

Stratton, et al., Adverse events associated with Childhood Vaccines, Evidence Bearing on Causality, Washington, DC: National Academy Press (Book), pp. 153–159, 1994.

Dahlquist, et al., *Indications that maternal coxsackie B virus infection during pregnancy is a risk factor for a childhood-onset IDDM*, Diabetologia, vol. 38, pp. 1371–1373, 1995.

Gaskins, et al., *Beta Cell Expression of Endogenous Xenotropic Retrovirus Distinguishes Diabetes–susceptible NOD/Lt from Resistant NON/Lt Mice*, J. Clin. Invest., vol. 90, pp. 2220–2227, 1992.

Golding, eds., From Birth to Five: A Study of the Health and Behavior of Britain's Five Year Olds, Chapter 20 (pp. 295–319) and Chapter 1 (pp. 1–11) (Pergamon Press 1986).

\* cited by examiner

METHOD AND COMPOSITION FOR AN EARLY VACCINE TO PROTECT AGAINST BOTH COMMON INFECTIOUS DISEASES AND CHRONIC IMMUNE MEDIATED DISORDERS OR THEIR SEQUELAE

This is a continuation of Ser. No. 09/611,415 filed Jul. 6, 2000, granted, U.S. Pat. No. 6,420,139, which is a continuation of Ser. No. 08/591,651 filed Feb. 12, 1996, now pending, which is a 371 of PCT/US94/08825 filed Aug. 4, 1994, which is a continuation-in-part of Ser. No. 08/104,529 filed Aug. 12, 1993, granted, U.S. Pat. No. 5,728,385.

BACKGROUND OF THE INVENTION

1. Field of the Invention

The present invention involves the fields of immunology and medicine, and more particularly relates to immunization methods, and compositions used therewith, for immunizing young mammals, such as human infants and children, against at least one chronic immune mediated disorder, and, preferably, also against at least one infectious disease.

2. Related Background Art

Human Pediatric Immunization.

A number of severe childhood diseases can strike early in life. Pertussis may pose a serious threat to infants under three months of age, and, during the heyday of the polio epidemic, paralytic cases were reported in the 6–12 month age group with disturbing frequency.

Consequently, to avoid any gap in immunity, it was thought desirable to initiate immunization before infants lost passive protection-from maternal antibodies. However, the presence of maternal antibodies can modify or suppress the infant's response to immunization, especially if the vaccine preparations are of low potency. The maturity of the infant's immune system is also a consideration, and premature immunization can result in immunological paralysis.

Accordingly, it has been generally recommended to postpone immunizations in developed countries where maternal antibodies provide protection against infant infectious diseases until after the age of 2 to 6 months, when the modifying effect of the maternal antibodies had disappeared. Therefore, immunizations should induce an active immune response before the infant loses this passive protection, so that there will be continuous protection from birth without any gap in immunity to natural diseases.

More recently, it has generally been recommended to begin infant immunizations, such as DTP (diphtheria, tetanus and pertussis) and OPV (oral polio virus), at younger ages, and many countries have carried out successful immunization studies and programs beginning at 6–8 weeks of age in developed countries (Expanded Programme on Immunization (1984); (1985)). Accordingly, current recommendations for infant immunization is to provide routine DTP and OPV immunization initiated at no earlier than 6 weeks of age in all developed countries.

The literature on immunization schedules for pediatric vaccines is voluminous, but the examples which follow indicate what has been tried.

Provenzano et al., New England J. Med., 273:959–965 (1965) gave a first dose of a plain pertussis vaccine at 6–24 hours after birth. In Group I, two more such doses were given at three week intervals, and then two doses of combined diphtheria, tetanus and pertussis vaccine (DTP) at one month intervals. In Group II, the initial plain pertussis immunization was followed by three DTP injections at one month intervals.

The authors reported that the immunization response in both groups was inadequate, and attributed it to immunological paralysis "induced by the vigorous immunization schedule employed and the initiation of immunization on the first day of life."In view of earlier studies, they recommended that immunization not be attempted under three weeks of age.

Dengrove, et al., Pediatric Res., 20:735 (1986) gave a first dose of DTP to infants before 4 days of age, and further doses at 2, 4 and 6 months of age. The immune responses to diphtheria and tetanus immunogens were acceptable, in contrast to their previous demonstration that "an early neonatal dose of DTP resulted in a lowered pertussis antibody response in the subgroup of infants who had low maternally acquired levels of antibody."

Only 45 infants were treated, and therefore, even if this schedule could be effective to inhibit diabetes, it is unlikely that any of the infants actually were benefited (immune-mediated diabetes occurs in only one out of 200–300 individuals).

The immunization protocol used by Baraff, et al., Pediatrics, 73: 38–42 (1984) was similar, but the technology used to evaluate the immune response was more sophisticated. It was found that the IgG response to the pertussis lymphocytosis-promoting toxin (LPT) was lower and the IgM anti-FHA (filamentous hemagglutinin) response higher in the early immunization group than in controls. The authors were of the opinion that the anti-LPT response was of greater clinical significance and therefore concluded that neonatal immunization may be disadvantageous. This would have discouraged use of both Dengrove's and Baraff's protocols.

Perkins, et al., British Medical J., 0.68–71 (Jul. 12, 1958) investigated the response of infants to immunization with a killed poliomyelitis vaccine. The first dose was given to Group A at 1 week of age, Group B at six weeks of age, and Group C at ten weeks of age. A second dose was given four weeks later. Three different virus types were tested in these three groups.

Perkins et al. found that maternally transmitted antibodies interfered with the immune response of the infants to the vaccines. Maternal antibodies declined with age (the half life was about 21 days). The type 2 vaccine was the least susceptible to this interference, but according to table 4, it too, felt it (60% of Group C infants responded, as compared to 35 of those in Group A).

Based on these findings, Perkins et al. concluded "in order to avoid the inhibiting effect of the placentally transmitted antibody, immunization should at present be delayed until six to nine months after birth."

Another study, by Spigland and Goldblum, Pediatrics 25:812–821 (1960) divided infants into groups A (1 and 2 months old), B (3 and 4 months old), and C (5 and 6 months old). Primary immunizations was either at (a) 0 and 21 days, or (b) 0, 7 and 21 days from the first immunization. The vaccine was the formalin-inactivated salk poliomyelitis vaccine. The authors concluded that "presence of maternal antibody seemed to interfere with active production of antibody," and that "the greater the age of primary immunization, the better the response."

In a recent pulse immunization study by: John, British Medical Journal 289:88 (1984) the first dose of an oral poliomyelitis vaccine was given at 7, 14, 21, 28, 35 or 42 days of age, and the second and third doses at intervals of four weeks. The immune response to the oral vaccine, unlike the parenteral vaccine discussed previously, did not appear to be affected by the age of the infant. The authors recommended that children be immunized with the polio vaccine at 1 and 5 weeks, and with polio-plus-DPT at 9, 13, and 17 weeks. The present inventor believes that this immunization schedule would be disadvantageous as the late administration of pertussis would promote the development of diabetes and counteract any anti-diabetic effect of the early polio vaccine dosage.

Barrett, Jr., et al., J. Am. Med. Asso., 167:1103–6 (1958) considered whether it would be advantageous to combine the polio and DPT vaccines. The tetravalent vaccine was administered to children ranging in age from 2½ months to 5 years. Only polio antigen response was measured. The study found that "older children respond much more dramatically than do the infants."

Barrett, Jr. et al., Pediatrics, 30:720 (1962) gave a series of polio-DPT inoculations, beginning at various ages, and then at 1, 2, 3 and 4 months post-initial immunization. The first immunization was at (A) 1–2 days old, (B) 1–2 months old, (C) 3–4 months old or (D) 5–6 months old. Based on their observations, the authors recommended that the initiation of both polio and pertussis immunizations be withheld until the infants was three months of age.

A rather extensive review of the literature-on DPT and oral poliomyelitis vaccine (OPV) immunizations has been given by Halsey and Galazky Bull. World Health Org., 63:1151–69 (1985). They compare the antibody response following one dose of OPV at 1–12 weeks of life (Table 1) with that to 2–3 doses beginning at 6–8 weeks of life (Table 2), and recommend that in countries where polio-myelitis has not been controlled, trivalent OPV be given at birth and at 6, 10 and 14 weeks of age. Pertussis vaccine schedules are reviewed in Table 3. The response to immunization beginning at 4 or more weeks was said to be almost as good as the results obtained by beginning at eight or more weeks. They recommended initiating DPT at six weeks of age.

Infants as young as 1–2 months old at the time of initial immunization have received a *Hemophilus influenza* (bacterial meningitis) (Hibtiter) vaccine (three doses at two month intervals.) Madore, et al., Pediatrics, 85:331–337 (1990). However, Madore, et al. stated that older children responded better than younger children, and their employer, Praxis Biologics, eventually recommended that its Hibtiter vaccine be given to children at 2 to 71 months of age (see PDR). Neonatal vaccination with Bacille Calmette-Guerin (BCG), and its impact on malignant disease, is briefly addressed by. Grange and Stanford, Tubercle 71:61–64 (1990). A four dose vaccination schedule has been used to interrupt perinatal vertical transmission of hepatitis B virus, the first being given in the first week of life, and others at 1, 3 and 6 months of age.

While vaccines are subject to safety review, both before and after marketing approval, prior to the present invention, chronic immune mediated diseases, such as diabetes mellitus, were not considered vaccine complications. Many vaccines have been approved based on studies of only a few thousand recipients followed for only a short time after receiving the vaccine. These studies are inadequate to detect the effect of vaccines on chronic immune mediated diseases that are rare and don't develop until many years after a recipient received a vaccine. Current trials with new vaccines only compare results to people who received standard immunization. If both groups received vaccination starting at 2 months, which is now discovered to be associated with the increased risk then both groups will be associated with a higher than necessary risk of diabetes and other chronic immune mediated disorders. Additionally, current vaccine trials are not designed to look for complications of diabetes or other chronic immune mediated disorders which may not occur until 15 years, or more, after a person is immunized.

Likewise bioassays performed to show safety of vaccines are inadequate because the animals used are from strains that are not susceptible to vaccine induced chronic immune mediated diseases, such as diabetes.

The lack of concern over the ability of vaccines to induce a chronic immune mediated disorder (e.g., but not limited to, diabetes) is further evidenced by the lack of warnings on package inserts and labels of such products about such diseases.

As shown above, background art favors administration schedules that induce high levels of antibodies protective against the targeted infectious agent, and therefore typically require beginning immunization at a relatively late age (e.g., for DTP, at two months). The data presented in the present specification shows that such an immunization schedule can cause or at least substantially contribute to the development of chronic immune mediated disorders, e.g. diabetes, as discussed herein.

Animal Pediatric Immunization.

Lee, U.S. Pat. No. 4,857,318 intraperitoneally administered a vaccine against *Bordetella pertussiss* to pigs when 7 and 21 days old, or 6 and 12 days old. Intraperitoneal administration of vaccines to humans is usually undesirable because of the risk of perforating the intestine. Green, U.S. Pat. No. 4,625,015 administered an influenza immunogen to mice at 28, 42 and 56 days after birth. The immunogen was adjuvanted with Freund's complete adjuvant, which is too toxic for human use. In vaccinating humans against influenza, FCA would have to be omitted, with a consequent reduction in the overall immunizing effect. Green does not explain how to adapt his agent or protocol for immunizing humans.

Kuzehara, U.S. Pat. No. 5,151,023 administered a single dose of a combined Hepatitis A and B vaccine to guinea pigs and mice, subcutaneously, at 28 days of age.

Chronic Immune Mediated Disorders.

Many chronic immune mediated disorders, such as immune mediated cancers and hyperactive immune responses, can be induced or inhibited by cells of the immune system. Environmental stimuli can affect whether those genetically predisposed to a chronic immune mediated disorder will develop symptoms or not. For example, it is not uncommon for one identical twin to have a chronic immune mediated disorder (e.g., type I diabetes mellitus) and the other identical twin to be free of the disorder.

Several methods have been used to modulate an immune response in order to treat autoimmunity early stages of diabetes mellitus (e.g., as disclosed in U.S. Pat. No. 4,710, 380).

Immunosuppressive agents, including both general immunosuppressants and antigen specific tolerizing agents, have been used to some extent to inhibit or treat chronic immune mediated disorders like autoimmunity. General immunosuppressants can lead to overwhelming infections and other toxicities as in bone destruction associated with corticosteroids and kidney disease associated with cyclosporine.

Antigen-specific agents that cross-react to a specific autoantigen have been employed to down-regulate immune responses to a particular autoantigen. An example of this approach is contained in PCT patent application (PCT/

US90/01397, WO/10449) which discloses the use of antigens which cross-react with a 65 Kd heat shock protein as tolerizing agents. Alternatively, PCT/US91/00240 (WO 92/00755) discloses utilizing sub-immunogenic amounts of an antigen which cross-reacts to alloimmune serum, in order to tolerize individuals. The problem with antigen specific agents is that one often does not know all the autoantigens involved in an autoimmune disease and the mechanism requires knowledge of such molecules.

Effect of Immunogens on Immune Disorders.

Harada, et al. (1990) reported that a single intravenous injection of live BCG into 5 or 10 week old NOD mice suppressed insulitis and overt diabetes, while an injection into 15 week old mice was somewhat less suppressive.

The dose given by Harada, 0.25–1 mg, is, on a per kg body weight basis (about 8–32 mg/kg) equivalent to a human dose which would not be considered pharmaceutically acceptable. It is not unclear whether Harada's findings regarding the effects of immunication with a live organism are extrapolatable to immunization with inactivated organisms or purified antigens as a live organism which provides continuing exposure of the host to the organism's antigens. BCG's effect may be attributable to its heat shock protein, a known tolerogen, rather than to a specific immunogenic effect. BCG vaccination has also been inconclusively reported to be associated epidemiologically with both an increased (Salonen, 1975) and decreased (Hems, 1971) incidence of childhood leukemia (Grange, 1990).

Huang, et al (1984) administered one dose of a whole cell Bordetella pertussis vaccine to mice which were at least 45 days old. The dose was given from 10 days before to 30 days after injection of streptozotocin (STZ), which produces a form of insulin-dependent diabetes. The pertussis vaccine aborted the development of IDD as a result of a single injection of STZ. Kolb, et al (1987) also looked at the effects of a pertussis vaccine in a streptozotocin-induced diabetes mouse model. The streptozotocin was administered when the mice were 8–11 weeks of age. The vaccine was given at day –3,+8, or +14 relative to STZ initiation. Given at day –3, it partially suppressed the hyperglycemia, while when given at days –8 and –14, it strongly enhanced it.

As admitted by Huang et al. (1991), "results from streptozotocin-induced IDDM experiments are difficult to extrapolate to type I IDDM because the correlation between chemically-induced diabetes and a "natural" development of autoimmune diabetes is unclear." Consequently, Huang et al (1991) examined the anti-diabetic effect of pertussigen in the genetically predisposed NOD mouse. These mice were give four injections of pertussigen at four week intervals, starting when the mice were 2 (Group 1) or 4 (Group 2 and 3) weeks of age. According to the authors, "although the time at which IDDM was first observed was delayed by several weeks, the incidence rates were not significantly different from those of untreated control NOD mice."

Toyota et al (1978) administered the islet activating protein of Bordetella pertussis to spontaneously diabetic rats aving a weight of 300–400 g. While the age of the rats is not stated, this body weight could not be attributed to a rat younger than 42 days. Furthermore, the animals were already diabetic before the administration of the protein thus the administration was intended as a therapy as opposed to a method of immunization.

It has recently been suggested that vaccination against measles may influence a reduction in the incidence of diabetes, however the data obtained was inconclusive because it failed to look at those who did not receive the vaccine and who did not develop the disease (Blom, 1991). These individuals are here discovered to in fact be at lower risk for developing diabetes than those who received the vaccine.

Effects of Immunomodulators on Immune Disorders.

Several papers discuss the effect of OK-432, a streptococcal preparation, on diabetes in mice. (Toyota, et al. 1986; Shintani, et al. 1990). Toyota et al., 1986, gave two clinical units of OK-432 to mice every week from 4–24 weeks of age. Shintani, et al. (1990) also tested schedules-of weekly immunization at 4–15, 4–9, and 10–15 weeks of age. Weekly injections were needed at a dose of approximately 0.1 mg/20 g, (5 mg/kg or 100 KE/kg) mouse to provide the protective effect (Shintani, Satoh, Seino, et al 1990), while pharmaceutically acceptable clinical doses would be 0.07 KE/kg or 1400 times less.

OK-432 is a pyretic agent. See Shinoda, et al. Acta Urologica Japonica, 38:1299–13 ct (1992); Luh et al., Cancer, 69:674–9 (1992), Imamura, et al., Cancer, 68:259–63 (1991); Ogita, et al., J. Pediatric Surgery, 26:263–8 (1991). While it may be reasonable to prescribe it to a patient with cancer, it would not be clinically indicated for prevention of diabetes in youngsters. Young-children are particularly prone to seizures as a result of high fevers. Ogita et al. used OK-432 only to treat surgically unresectable lymphangiomas in children.

Oldstone (1988) inoculated NOD mice with live, unattenuated, lymphocytic choriomeningitis virus (LCMV) either intracerebrally at birth with LCMV ARM536 or intravenously with "clone 13" at six weeks of age. Both treatments prevented the spontaneous development of type 1 diabetes characteristic of NOD mice. This work was elaborated upon by Oldstone, et al. (1990), who inoculated NOD mice intracerebrally, within the first eighteen hours of life, with various LCMV strains and reassortants. Schwimmbeck, et al. (1989) found that acute infection with LCMV at 30 days of-age abrogated diabetes in BB rats.

However, these inoculations did not immunize the rodents against LCMV, and therefore did not offer protection against an infectious disease. Indeed, the administration infected the rodents with the virus, which persisted throughout the animal's lifespan, and altered the cytotoxicity of the host's T lymphocytes. The present invention does not contemplate inoculating a subject with a live, unattenuated virus. Lympho-tropic viruses are potentially very dangerous, as the case of HIV illustrates, and it would be difficult to win clinical acceptance of such a virus as a human therapeutic agent., Moreover, intra-cerebral administration of vaccines to humans is undesirable because of the risks of damaging brain cells or inducing meningitis. In any event, the administration of other viruses has been shown to increase the incidence of diabetes (Guberski et al, 1991: Kilham's rat virus in BB/Wor rats).

Several other agents have to be used in attempts to alter the development of immune mediated disorders. Specific lymphokines like IL-2 (e.g., according to Serreze et al, 1989) and tumor necrosis factor (e.g., according to Satoh et al, 1989) have also been employed to attempt to treat or prevent immune mediated disorders thought to be caused by lymphokine defects, by using multiple injections. However, purified lymphokines are relatively toxic, and expensive, and have short half lives.

Freund's adjuvant (Sadelain et al, 1990) has also been used to delay the development of diabetes in NOD mice. However, this adjuvant is not suitable for vaccine use in mammals at levels comparable to those used by Sadelein et al, (1990) due to its toxic effects. Freund's adjuvant can cause plasmacytomas as well as granulomas.

The use of anti-receptor and immune modulating agents (such as products that can block specific receptors, activate specific receptors, or cause the release of suppressor factors) generally requires repeated injections at high doses, e.g., in the mg/kg of body weight range. Examples of anti-receptor immunogens include monoclonal antibodies (e.g., U.S. Pat. No. 4,695,459) and lectins like Concanavalin A (e.g., Pearce and Peterson, 1991). Pharmaceutical use of monoclonal antibodies reactive to the antigen specific T-cell receptor have been shown to be associated with an increase in human lymphoid tumors and thus anti-receptor ligands reactive to the this T-cell receptor are unlikely to be pharmaceutically acceptable.

In conclusion, it has heretofore not been clearly shown or recognized that pharmaceutically acceptable doses of pharmaceutically acceptable immunogens can prevent chronic immune mediated disorders. The related art has also not demonstrated whether such agents would be of value in preventing chronic immune mediated disorders in mammals, especially humans, that are immunized early in life. The related art has also not shown when or how to administer such agents to a mammal which being immunized early in life against infectious diseases, in order to prevent or reduce the prevalence/incidence/frequency/severity of chronic immune mediated disorders.

Citation of documents herein is not intended as an admission that any of the documents cited herein is pertinent prior art, or an admission that the cited documents is considered material to the patentability of any of the claims of the present application. All statements as to the date or representation as to the contents of these documents is based on the information available to the applicant and does not constitute any admission as to the correctness of the dates or contents of these documents.

SUMMARY OF THE INVENTION

The present invention relates to the discovery that when one or more immunogens, in a pharmaceutically acceptable composition, is first administered at an early age (typically prior to 42 days of age), it can substantially decrease the incidence, frequency, prevalence or severity of, or prevent, at least one chronic immune mediated disorder, and/or a surrogate marker thereof. Usually, at least one of these early administered immunogens is administered with the additional purpose of immunization against an infectious disease. Indeed, the immunogens which thus combat a chronic immune mediated disorder may collectively contribute to protection of the subject against two, three, or even more, infectious diseases.

Without intending to be bound by any theory, early administration of immunogens can cause the release of lymphokines that may accelerate the maturation of the immune system in a manner which reduces the likelihood of development of a chronic immune mediated disorder. The immunization may act in several ways including:

A. Enhancing destruction of autoimmune prone cells in the thymus;

B. Enhancing the flow of normal T-cells from the thymus;

C. Causing peripheral elimination of autoreactive T-cells that have escaped the thymus;

D. Causing the release of interferons which prevent infection with autoimmune causing viruses; and/or E. Causing migration of macrophages into the area of administration as in an injection site and away from an vital organ like the islet cells of the pancreas. The invading macrophages have the ability to act as antigen presenting cells and induce an autoimmune response against the vital tissue.

The present invention may therefore be said to relate to early immunization programs which achieves one or more of these activities.

In contrast, the late administration of an immunogen can cause the release of lymphokines which may act as growth factors enabling autoimmune inducing cells to grow.

In preferred embodiments, the immunization schedules of the present invention may include employing initiating immunization prior to 28 days, supraimmunogenic doses, multiple doses prior to 56 or 112 days of age and/or dosing intervals of less than 28 days.

In some embodiments, the immunization schedule comprises administration of at least one non-pediatric immunogen (e.g. anthrax or plague immunogens).

New pharmaceutical agents of the present invention are described that contain both non-pediatric and pediatric immunogens. Methods of manufacturing such agents are also included. Kits are described containing in receptacles at least one non-pediatric immunogen and at least one pediatric immunogen. However, such agents and kits are not required for the practice of the invention.

Methods are also provided for screening immunogenic agents for their ability to modulate the development of at least one chronic immune mediated disorder in a mammal such as a human.

The present invention is especially useful in preventing diabetes mellitus and systemic lupus erythrematosis.

Other objects, features and advantages of the present invention will be clear to those skilled in one or more of the relevant arts, based on the teachings and guidance presented herein.

BRIEF DESCRIPTION OF THE DRAWINGS

FIG. 1 depicts data from Example 1. Results show that mice receiving anthrax vaccine (A exp1) reached a peak cumulative incidence of diabetes of 42.1% at 24 weeks of life and no new cases of diabetes were detected through week 36 of life. The control receiving PBS (PBS exp1) showed a steady increase in the cumulative incidence of diabetes and 75% of mice had become diabetic by 36 weeks of life. Those animals receiving the plague vaccine (Plague exp1) had a lower incidence of diabetes than the controls throughout most of their life span. The plague vaccine treated animals had a cumulative incidence of diabetes of 57.9% at 28 weeks and development of diabetes appeared to be leveling off after 26 weeks. Plague vaccine treated animals were sacrificed at 28 weeks.

FIG. 2 depicts data from Example 2. Animals were given 1 of 6 treatments: anthrax and the whole cell DTP vaccine (ADPT exp2); anthrax and the diphtheria tetanus vaccine (ADT exp2); anthrax vaccine alone (A exp2); a single injection of DTP vaccine at week 8 (control+DPT exp2); anthrax and the diphtheria tetanus vaccine with the whole cell DTP vaccine substituted for the diphtheria tetanus vaccine at 8 weeks (ADT+DPT exp2); and PBS control (PBS exp2). Data show a single injection of DTP does not prevent diabetes and actually increases the incidence of diabetes as seen in the difference between the group receiving ADT+DPT and ADT. All of the animals in the group receiving ADTP did not develop diabetes.

FIG. 3 depicts data from Example 4. BB rats received either DTP and Anthrax vaccines (squares) or nothing (control; stars). Results show at 16 weeks of age 54% of the untreated rats had developed diabetes and or died compared to 20% in the vaccinated group. At 20 weeks of age 54% of the untreated rats had developed diabetes and or died compared to 25% in the vaccinated group. At 32 weeks the results were 54% versus 35% respectively which represents a 34% reduction in the incidence of diabetes. The difference between the two groups were statistically significant at 20 weeks (P=0.027).

DETAILED DESCRIPTION OF THE PREFERRED EMBODIMENTS OF THE INVENTION

Figure 1:
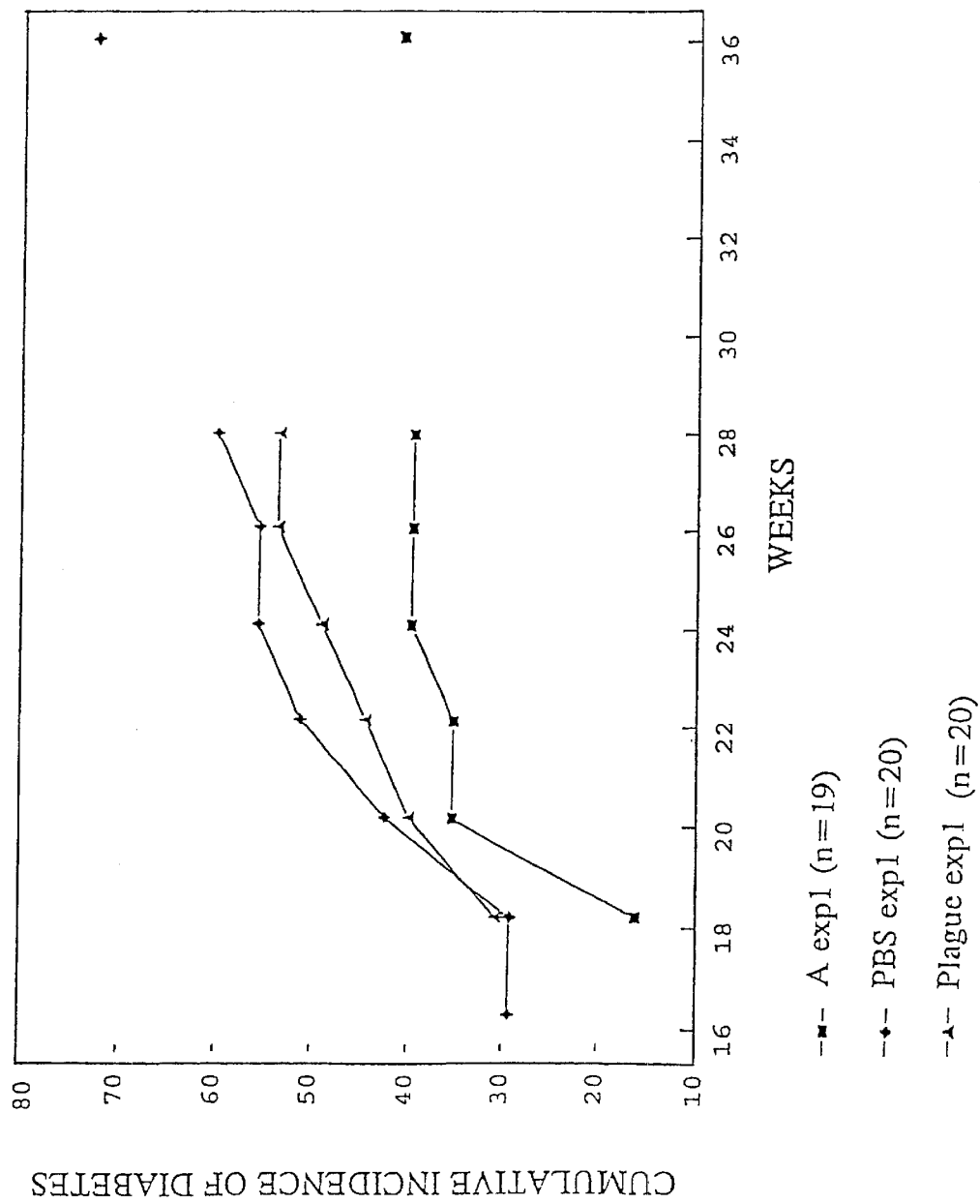
In FIGS. 1–3, the trendlines plot the % diabetic (ordinate) against age (in weeks after birth, abscissa).
Figure 2:
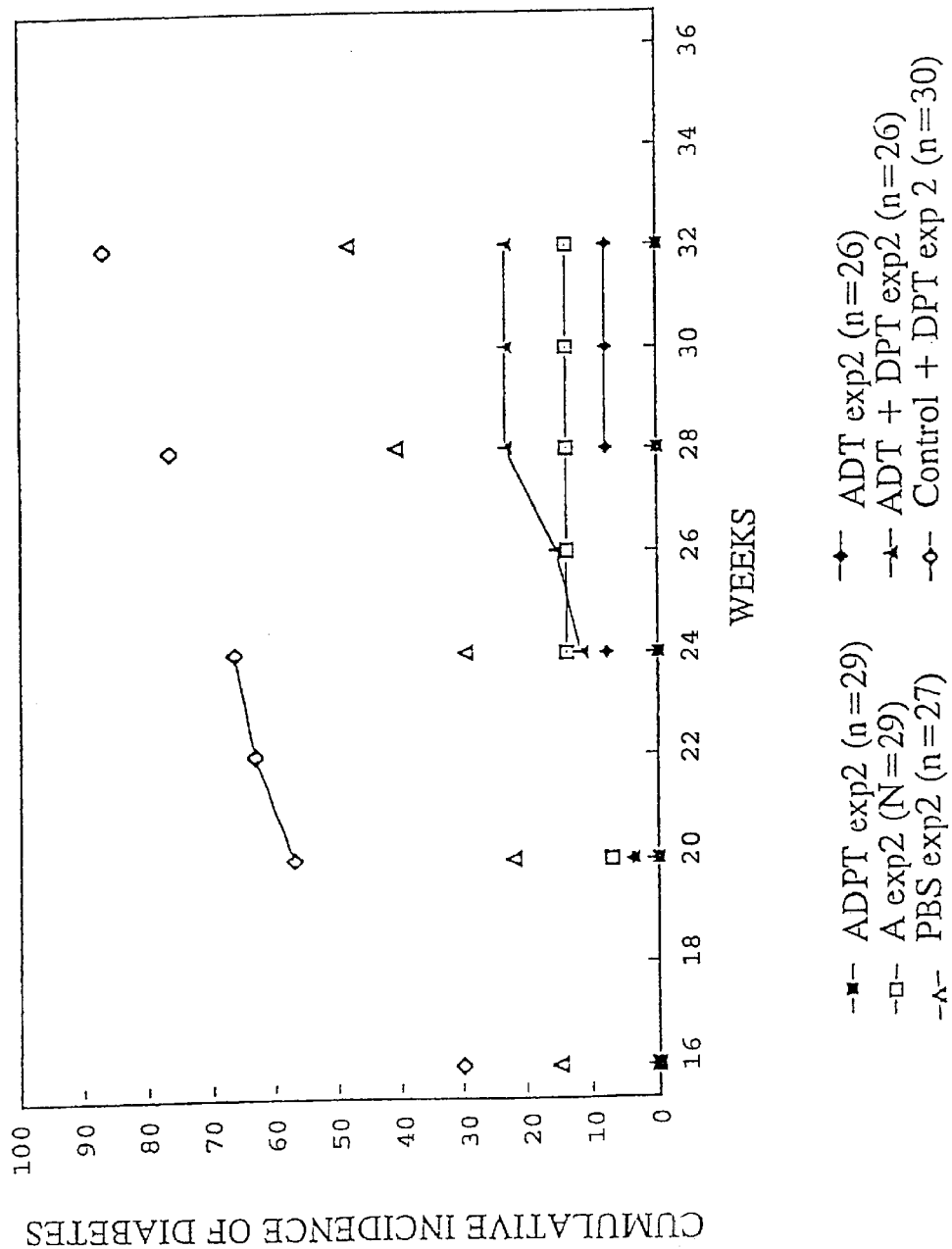

Thus, it has now been discovered that the occurrence and/or severity of chronic immune mediated disorders may be substantially prevented, or their symptoms, prevalence, incidence, severity, or-frequency reduced, by administration to a mammal, such as a human, of at least one pharmaceutically acceptable dose of a pharmaceutically acceptable immunogenic agent, wherein the first pharmaceutically acceptable dose is given prior to the first 6–8 weeks of life.

It was also unexpectedly found that immunization with conventional pediatric vaccines beginning at 6–8 weeks, which is the common immunization protocol in developed countries, actually can increase the probability that a mammal will develop a chronic immune mediated disorder. Current vaccination protocols., such as childhood active immunization protocols (e.g., as presented in THE MERCK MANUAL, 16th ed., 60–64 and 1944–47 (1992) entirely incorporated herein by reference) may at best only slow the progression of immune mediated disorders, but not prevent them.

While typically the subject of immunization will be a human being, it may also be a nonhuman mammal, especially mammals of the orders Primata (monkeys or apes), Carnivora (especially one of the domesticated species such as dogs and cats), Artiodactyla (especially one of the domesticated species such as horses, goats, pigs, sheep, cows), or Rodenta (especially domesticated or laboratory species such as mice, rats, rabbits and hamsters).

The subject may be healthy at the time of immunization, or may be one suffering from an adverse clinical condition such as prematureness, diarrhea, infection, or fever.

Chronic Immune-Mediated Disorders

A chronic immune mediated disorder is one which lasts longer than two months, but does not include permanent sequela of acute immune response diseases such as seizures and anaphylaxis, nor do such disorders include diseases associated with live virus infections as in subacute sclerosing panencephalitis induced by measles vaccine. Chronic immune mediated disorders does not include sequela caused by chronic infections by live vaccines. The invention is especially useful in preventing chronic immune disorder which develop at least one year after a vaccination. Thus, an illness like Guillean-Barrea syndrome is not routinely considered an chronic immune mediated disorder.

A growing number of human diseases have been classified as autoimmune in nature (see, Theofilopoulos, A., In: D. P. Stites, et al., eds., *Basic and Clinical Immunology*, Lange Medical Publications, Los Altos, Calif., 1988; and Berkow, supra), which references are entirely incorporated by reference, and the present invention is intended to include as a chronic immune mediated disorder any and all of such diseases, with the exception listed herein, in mammals including humans.

Methods and compositions of the present invention may be used for preventing and/or inhibiting chronic immune mediated disorders including immune mediated cancers and hyperactive immune responses. Such immune mediated cancers may include lymphoreticular neoplasia, lymphoblastic leukemia, brain tumors, gastric tumors, plasmacytomas, multiple myeloma, leukemia, connective tissue tumors, solid tumors and lymphomas. Such hyperactive immune responses may include asthma/allergies and autoimmune diseases. Such allergies may include hay fever, atopic dermatitis, urticaria, perennial rhinitis, allergic conjunctivitis, pulmonary diseases, food allergies, skin allergies, anaphylaxis (e.g., associated upon exposure to blood products) and pollinosis. Such autoimmune diseases may include type 1 diabetes, conventional organ specific autoimmunity, neurological disease, rheumatic diseases/connective tissue disease, autoimmune cytopenias, and related autoimmune diseases. Such conventional organ specific autoimmunity may include thyroiditis (Graves+ Hashimoto's), gastritis, adrenalitis (Addison's), ovaritis, primary biliary cirrhosis, myasthenia gravis, gonadal failure, hypoparathyroidism, alopecia, malabsorption syndrome, pernicious anemia, hepatitis, anti-receptor antibody diseases and vitiligo. Such neurological diseases may include schizophrenia, Alzheimer's disease, depression, hypopituitarism, diabetes insipidus, sicca syndrome and multiple sclerosis. Such rheumatic diseases/connective tissue diseases may include rheumatoid arthritis, systemic lupus erythematous (SLE) or Lupus, scleroderma, polymyositis, inflammatory bowel disease, dermatomyositis, ulcerative colitis, Crohn's disease, vasculitis, psoriatic arthritis, exfoliative psoriatic dermatitis, pemphigus vulgaris, Sjorgren's syndrome. Other autoimmune related diseases may include autoimmune uvoretinitis, glomerulonephritis, post, myocardial infarction cardiotomy syndrome, pulmonary hemosiderosis, amyloidosis, sarcoidosis, aphthous stomatitis, and other immune related diseases, as presented herein and known in the related arts. See, e.g., Berkow et al., eds, supra, pages 303–364, 710–718, 1083, 1269, 1305–1377, 1338 1677–1684, and 2435–2438 which is entirely incorporated herein by reference.

Type I diabetes mellitus is defined herein as an naturally occurring or spontaneously developing disease of the pancreatic islet cells that is not intentionally induced. This definition is intended to differentiate the natural disease from altered insulin secretion following the deliberate or intentional destruction of pancreatic islet cells through the use of toxic agents, surgery or other bodily insults.

Type II diabetes mellitus will benefit from the invention as a non-limiting example. The etiology of this disorder is poorly understood. However, scientists believe some patients are unable to secrete enough insulin or are resistant to insulin. Scientists have not ruled out that many of these patients fail to produce enough insulin because they have insufficient islet cells. Scientific evidence suggests that failure to produce sufficient insulin in some type II diabetics is due to destruction of islet cells (Niskanen et al 1991). This evidence includes-the presence of autoantibodies to islet cells. These patients differ from type I patients in that they produce enough insulin to prevent them from becoming ketotic and they develop disease later in life. A person who is resistant to insulin and needs more insulin to survive would be at a disadvantage if that person had lost a substantial amount of his or her islet cells do to an immune mediated attack earlier in life. A vaccine to protect islet cells would thus be advantages to people pre-disposed to type II diabetes. Accordingly, methods and immunogenic agents of the present invention provide a treatment for reducing the severity or incidence of diabetes.

There are multiple sequelae to chronic immune mediated disorders. As non-limiting examples, autoimmunity can result in end organ failure or cancer. Chronic inflammation, as occurs in chronic immune mediated disorders, can cause the release of molecules like serum amyloid which can cause pathology. Serum amyloid is associated with amyloidosis peripherally and senile dementia in the central nervous system.

The present invention is intended to utilize low or non toxic agents that can be used to prevent disease in asymptomatic mammals without the need to screen them for risk of developing chronic immune mediated disorders, however the invention may be used in certain subpopulations at higher risk for developing the disorders than others. Alternatively the invention may be administered to a large number of mammals with different risks for developing a given chronic immune disorder and only certain subpopulations may be shown to benefit statistically from the administration. The subpopulations may include mammals at higher risk than the general population. Non-limiting examples of the subpopulations include those with family history of at least one chronic immune mediator disorder, those who are deemed at high risk because of genetic or biochemical screening of themselves or biological relatives, and those at risk because of an abnormal birth as in prematurity or small size.

Immunization Schedule

An immunization schedule is a program for the administration of one or more specified doses of one or more specified immunogens, by one or more specified routes of administration, at one or more specified ages of the immunization subject. A supplemental immunization schedule is one intended to supplement a standard immunization schedule which is commonly followed in the region in which the subject resides.

The immunization schedules of the present invention induce an immune response in the subject sufficient to reduce at least one measure selected from the group consisting of incidence, prevalence, frequency and severity of at least one chronic immune mediated disorder, and/or at least one surrogate marker of the disorder, in a population and/or subpopulation of the mammals. A supplemental immunization schedule is one which has this effect relative to the standard schedule which it supplements. The supplemental schedule may call for additional administrations and/or supraimmunogenic doses of immunogens found in the standard schedule, or for the administration of immunogens not part of the standard schedule. The latter may be non-pediatric immunogens. The full immunization schedules of the present invention may comprise both a standard schedule and a supplemental schedule.

In the method of the present invention, the first administration of an immunogen, especially one which also serves to contribute to immunization against an infectious disease, usually occurs when the subject is less than 42 days of age (in the case of a non-pediatric immunogen, the first administration could be as late as 55 days of age), more preferably less than 28 days of age, still more preferably less than 14 days of age, and most preferably at about 7 days of age. It is permissible to begin the program at an even earlier age, e.g., within the first 24 hours after birth. The "age", it should be noted, is measured from birth and not from conception.

While it is possible that the purposes of the present invention can be served with a single administration, especially when the immunogen is a strong one, and in that case a single dosing schedule is within the compass of the present invention, it is desirable to administer two or more dosings for greater surety. Preferably, the number of dosings is at least three, more preferably at least four, and still more preferably, at least five. There is no set maximum number of vaccinations, however it is good clinical practice not to immunize more often than necessary to achieve the desired effect. (For the purpose of the appended claims, the administration of two different immunogens, or of two packets of the same immunogen, within a period of less than 24 hours, is considered a single dosing.)

Example 1, as non-limiting example, shows that just three vaccinations with a single mild agent, anthrax vaccine, can cause a profound reduction in diabetes. Increasing the number of vaccinations increases the effect of a mild agent like the anthrax vaccine, as seen by the improvement from Example 1 to Example 2.

When an immunization schedule calls for two or more separate dosings, it is necessary to consider the intervals between dosings. The interval between two successive dosings may be the same throughout the program, or it may change as the subject ages. As immunizations are usually incorporated into routine office checkups, and these usually become less frequent as the child's health becomes a known quantity, it is not unusual for the interval to lengthen with age. While the interval can be shortened, there would have to be a tangible benefit for this to be acceptable to clinicians.

Preferably, in the immunization schedules of the present invention, at least during the first 175 days from birth, the shortest interval between successive dosings is less than 28 days, more preferably, less than 14 days, and still more preferably, about 7 days. Preferably, at least during the first 175 days from birth, the longest interval between successive dosings is less than 28 days, more preferably, less than or about 14 days.

The timing of the initial dosing and the intervals between successive dosings together determine how many dosings occur within a particular period in the subject's life. Within the first 112 days after birth, the subject preferably receives at least three, more preferably at least four, and still more preferably at least five dosings. Moreover, within the first 42 days after birth, the subject preferably receives at least two, and more preferably at least three, dosings.

The immune systems of mice and men mature at comparable rates, with both species capable of mounting immune responses to vaccine antigens by the time the recipients are several months old. A comparison of the experimental and epidemiological examples in this specification supports this conclusion. Subtle differences in the rates of development of the immune systems of mice and humans may be detected however using a broad range of assays including in vivo assays, in vitro assays, in vitro assays and phenotypci cell assays.

In vivo assays include the non-limiting examples of antibody responses and delayed type hypersensitivity responses. The anti-body responses primarily measures B-cell function as well as B-cell T-cell interactions while the delayed type hypersensitivity responses measure T-cell immunity. One may compare antibody titers in the blood following an antigenic challenge. These levels may be quantitated according to the type of antibody as in the non-limiting examples of IgG, IgG1, IgG2, IgM, or IgD. Once can also compare development of immune systems by determining levels levels of anitbodies and lymphocytes in the blood without antigenic stimulation.

In vitro assays may include the non-limiting examples of determining the ability of cells to divide, provide help for other cells to divide, release lymophokines and other factors, express markers of activation, and lyse target cells. Lymphocytes in mice and man can be compared in in vitro assays. Ideally one wants to compare the lymphocytes from similar sources as in the non-limiting examples of peripheral blood cells, spleenocytes, or lymphnode cells. It is possible however to compare lymphocytes from different sources as in the non-limiting example of peripheral blood cells in humans and splenocytes in mice. Cells may be puprified or left in their natural state as in the non-limiting example of purified B-cells, T-cells, and macrophages as compared to unpurified splenocytes or lymph node cells. Purification may be by any method that gives the desired results. The cells may be tested in vitro for their ability to proliferate using mitogens or specific antigens. Mitogens can specifically test the ability of-either T-cells to divide as in the non-limiting examples of concanavalin A and T-cell receptor antibodies, or B-cells to divide as in the non-limiting example of phytohemagglutinin. The ability of cells to divide in the presence of specific anitgens can be determined using a mixed lymphocyte reaction, MLR, assay. Supernatant from the cultured cells may be tested to quantitate the abilty of the cells to secrete specific lymphokines. The cells can be removed from culture and tested for their ability to express activation antigens. This may be done by any method that is suitable as in the non-limiting example of using antibodies or ligands to which bind the activation antigen as well as probes that bind the RNA coding for the activation antigen.

Phenotypic cell assays can be performed to determine the frequency of certain cell types. Peripheral blood cell counts may be performed to determine the number of lymphocytes or macrophages in the blood. Antibodies may be used to screen peripheral blood lymphocytes to determine the percent of cells expressing a certain antigen as in the non-limiting example of determining CD4 cell counts and CD4/CD8 ratios.

The present invention therefore can include administration of the immunogens to humans when said humans' immune systems are in a state of maturation and responsiveness comparable to that of mice or rats at the times indicated above, in such circumstances as it would be less effective to administer those immunogens to humans at the same chronological ages as they were administered to mice or rats.

Four non-limiting examples of vaccination schedules taught in the specifications are shown in Table V. These vaccine schedules were derived from information supplied in the specifications. Detailed descriptions of screening methods discussed herein allow one to develop alterations to the sample immunization schedules without undue experimentation.

Schedule 1 depicts a very intensive immunization schedule where the recipient is immunized in the first week of life and receives subsequent immunizations every two weeks. The recipient receives at least one non-pediatric immuogen along with common pediatric vaccines. All vaccines are administered during each scheduled imunization. Additional vaccines may be added to the vaccination schedule as in the non-limiting example of a hepatitis A vaccine. Vaccines may be omitted from the vaccination schedule as in the non-limiting example of the Hemophilus influenza vaccine. Vaccines may be continued for different durations of time.

Schedule 2 depicts another possible immunization schedule. Immunization is started on the second week. The immunization protocol is less intense since a non-pediatric vaccine is not administered. An oral polio vaccine is administered instead of the inactivated vaccine used in Schedule 1. As in Schedule 1, vaccines may be added or omitted or continued for different durations of time.

Schedule 3 depicts a third possible immunization schedule. Vaccines are administered starting soon after birth and immunization continues every third week. Vaccines are continued for different durations of time. The non-pediatric vaccine is administered four times, the hepatitis B vaccine is administered five times and other vaccines are administered seven times. Vaccines may be added or omitted or continued for different durations of time.

Schedule 4 depicts a fourth possible immunization schedule. Vaccines are started at different times in this schedule. The Pertussis vaccine and the MMR vaccines are started on week two while the other vaccines are started soon after birth. Immunizations are initially administered every two weeks but immunization frequency is shifted to every third week. Vaccines may be added or omitted or continued for different durations of time.

It will be appreciated by those skilled in the art that a variety of possible combinations and subcombinations of the various preferred conditions of timing of the first administration, shortest interval, largest interval and total number of administrations (in absolute terms, or within a stated period) exist, and all of these combinations and subcombinations should be considered to be within the inventor's contemplation though not explicitly enumerated here.

The inventor appreciates that it is conceivable that a prior experimenter has, without recognition of its anti-chronic immune-mediated disorder activity, proposed or even practiced an immunization schedule which falls within the present disclosure. If, under the applicable law, such a proposal or practice would be deemed to anticipate or render obvious an invention here claimed, then it is within the inventor's contemplation to excise from the invention the specific embodiment in question, preserving to the maximum degree permitted by law the scope of protection originally sought.

The ability of an immunization program to substantially reduce the incidence or severity of an immune-mediated disorder is preferably determined relative to a standard immunization protocol. The following three schedules are preferred standards:

| | | Schedule | |
|---|---|---|---|
| Week | 1 | 2 | 3 |
| 0 | x | x | HepB |
| 2 | x | x | x |
| 4 | x | x | HepB |
| 6 | DTP, Polio, HepB, HiB | x | x |
| 8 | x | DTP, Polio, HepB, HiB | DTP, Polio, HepB, HiB |
| 10 | DTP, Polio, HepB, HiB | x | x |
| 12 | x | DTP, Polio, HepB, HiB | DTP, Polio, HiB |
| 14 | DTP, Polio, HepB, HiB | x | x |
| 16 | x | DTP, Polio, HepB, HiB | DTP, Polio, HiB |
| 60 | MMR | MMR | MMR |

MMR: Measles, Mumps, Rubella
HepB: Hepatitis B
HiB: Hemophilus Influenza
x: No administration Preferably, a statistically significant ($p \leq 0.05$) reduction of at least about 10% is seen, relative to control employing one of these three schedules or relative to untreated controls.

More preferably, the reduction is greater, i.e., at least about 20% or at least about 50%.

When reduction in a surrogate marker is the criterion, the surrogate marker may be selected from the group consisting of an autoantibody, an autoreactive lymphocyte, a biochemical marker of tissue destruction, an biochemical marker of abnormal secretion from an internal body organ, an positive skin reaction to an immunological challenge which indicates immunological hypersensitivity, and an elevated level of antibodies that correlate with hypersensitivity.-The abnormal secretion from an internal body organ may be abnormal insulin secretion.

Preferably, one or more of the immunogens administered according to the immunization schedule is given, not only to achieve a beneficial effect with regard to chronic immune-mediated disorders,: but also to immunize the subject against an infectious disease. These infectious diseases include, but are not limited to, diphtheria, tetanus, pertussis, polio, hepatitis B, hemophilus influenza, measles, mumps, and rubella.

While the immunogens which can be administered according to the present invention are discussed in detail in a later section, certain prefatory remarks regarding their place in the immunization schedule are appropriate here. The immunization schedule may provide for one or more administrations of a single immunogen, multiple immunogens which collectively immunize against the same or different strains for the same infectious disease, or multiple immunogens which collectively immunize against a plurality of different infectious diseases. The administered immunogens may all be "pediatric immunogens", as hereafter defined, all "non-pediatric immunogens", or a combination of both. The immunogens may be separately or simultaneously administered, and, in the latter case, may be combined into a single pharmaceutical composition for ease of administration.

Immunogens

Immunogens correspond to a class of molecules that elicit an immune response through classical immunologic pathways as in the non-limiting example of the incorporation in an MHC molecule of an antigen processing cell where the immunogens can potentially interact with antigen specific T cell receptors. Alternatively, as another non limiting example, immunogens can bind to antigen specific binding regions of immunoglobulins which may lead to stimulating the B lymphocytes (if on the surface of B lymphocytes), but alternatively could elicit an immune response through other means, e.g., by the activation of complement, or the modulation of Fc receptors.

Immunogens may be derived from a virus, bacteria, yeast, mold, plant, insect, allogeneic or xenogeneic animal or a molecule, compound or composition that immunologically cross reacts with-a naturally occurring immunogen. Such agents may be made from the killed or live bacteria, killed or live viruses, recombinant or chemically synthesized or purified immunogenic agents including antigens, fragments or cross reacting synthetic or recombinantly produced peptides, carbohydrates, lipids or any combination thereof. Such agents can be combined with each other and with vaccines against infectious diseases to substantially prevent or reduce the incidence of immunologic disorders according to the present invention.

The term "immunologically cross reacts" refers to molecules that induce antibodies or T-cells that bind to the cross reactive molecule or fragments thereof.

Weak immunogens may be limited to the ability to invoke changes in such immune mediator cells, such as lymphocytes (B and/or T cells), macrophages and natural killer cells, such as the release of lymphokines, altered cell movement, or altered composition of cell surface receptors. Strong immunogens have the additional ability to cause either an humoral immune response (such as, e.g., antibodies to said agent) or a cellular immune response (such as, e.g., a delayed type skin reaction to said agent).

There are several examples of conventional immunogens. The classical example is that of vaccines as in human vaccines. Such vaccines may be classified as living where such agents may multiply or perform homeostatic metabolic activity in the recipient, as in the live oral polio, live BCG, and live small pox vaccines, as non-limiting examples. Alternatively, conventional vaccines can be classified as inactivated (killed), where such agents have lost their ability to multiply or maintain homeostatic metabolic activity. Non-limiting examples of such killed vaccines include tetanus toxoid, diphtheria toxoid, and the killed whole cell pertussis vaccine. Other non-limiting examples of conventional non-living immunogens are haptens, anti-idiotype antibodies, and nucleic acid molecules, such as DNA or RNA, that can be expressed in cells as immunogenic molecules encoded by such nucleic acids. Alternatively, conventional immunogens may be classified according to their functional or structural properties in a microorganism such as capsular, fimbriae, nuclear, cell wall, membrane, and cytoplasmic immunogens.

Chemically speaking, immunogens of biological origin are most often peptides (including proteins), carbohydrates, glycopeptides, lipids, glycolipids, or lipopeptides.

Immunogens of the present invention may be pediatric or non-pediatric immunogens. The term "pediatric immunogens" refers to immunogens that after birth were routinely administered to children less than 16 weeks old, in modern developed nations of moderate latitudes in 1992. These agents include but are not limited to BCG, measles, mumps, rubella, diphtheria, pertussis, hemophilus influenza, tetanus, hepatitis-B, and polio.

Non-pediatric immunogens are immunogens not routinely administered to children prior to 112 days in modern developed nations of moderate latitude in 1992, and may include, but are not limited to, the group consisting of anthrax, plague, encephalitis, meningococcal, meningitis, pneumococcus, pneumonia, typhus, typhoid fever, streptococcus, staphylococcus, neisseria, lyme disease, cholera, *E. coli*, shigella, leishmania, leprosy, cytomegalovirus (CMV), respiratory syncytial virus, Epstein Barr virus, herpes, influenza, parainfluenza, rotavirus, adenovirus, human immunodeficiency virus (HIV), hepatitis A, NonA NonB hepatitis, varicella, rabies, yellow fever, rabies, Japanese encephalitis, flavivirus, dengue toxoplasmosis, coccidiomycosis, schistosomiasis, and malaria immunogens.

It may be advantageous to include in the immunization schedule at least one immunogen against which the subject is unlikely to possess maternal antibodies; such an immunogen will normally elicit a stronger response and is less likely to cause immunological paralysis.

Immunosuppressants like corticosteroids, azathioprine, cyclosporine, and FK-506 do not activate immune mediator cells and are not considered immunogens in this invention. Tolerogens also are not generally considered immunogens in this invention, except as a tolerogen-immunogen, as described herein. A tolerogen is generally defined as an agent which induces a state of antigen specific immunological unresponsiveness to an antigen that immunologically cross reacts to the agent. Tolerogens are further considered agents that inactivate immune mediator cells like B and T lymphocytes by reacting to their antigen specific binding sight and inactivating the cells in an antigen specific manor. However, if a tolerogen has a component that is clearly immunogenic and causes activation of immune mediator cells resulting in antibody formation or T cell immune responses, then it can be both a tolerogen and an immunogen. A tolerogen-immunogen in the latter case may be employed in this invention to prevent chronic immune disorders by down regulating cells that do not directly bind to the tolerogen and/or prevent chronic immune responses against organs/antigens that do not cross react immunologically to said tolerogen.

Immunogens are distinct from immune modulators. There are several classes of immune modulators. One class is "immunocyte receptor ligands." Members of this class of agents bind to cell receptors of immune mediator cells in a non-antigen specific manner to cause the induction of an immune response, e.g., as defined herein. One subclass of this group is cytokines. Cytokines that are produced by lymphocytes are termed lymphokines, whereas peptides produced by monocytes or macrophages are given the term monokines. Thus, the terms cytokines, lymphokines, and interleukins may be used interchangeably to designate those peptide molecules that modulate host responses to foreign antigens or host injury by regulating the growth, mobility and differentiation of leukocytes and other cells.

Known cytokines include interleukins (IL) IL-1 (also endogenous pyrogen (EP), lymphocyte activating factor (LAF), mononuclear cell factor, catabolin, osteoclast activating factor and hematopoetin 1) IL-2 (also T cell growth factor,(TCGF)), IL-3 (multicolony stimulating factor (M-CSF), P-cell stimulating factor, WEHI-3B factor, mast-cell growth factor and histamine-producing factor), IL-4 (B-cell growth factor (BCGF), B-cell stimulatory factor-1 (BSF-1), IL-5 (T-cell replacing factor (TRF), B-cell growth factor II (BCGF-II), eosinophil differentiation factor (EDF), IL-6 ($\beta_2$ inteferon (IFN-$\beta_2$), B-cell stimulating factor 2 (BSF-2), 26-kDa protein, hybridoma/plasmacytoma growth factor (HPGF or IL-HP-2), hepatocyte stimulating factor (HSF), and T-cell activating factor (TAF)), IL-7, IL-8 (neutrophil activating protein 1 (NAP-1), IL-10 (also cytokine synthesis inhibitory factor (CSIF); tissue necrosis factors (TNF) TNF$\alpha$ (also lymphotoxin (LT) and TNF$\beta$ (also macrophage derived TNF); interferons (IFN) IFN$\alpha$ and IFN$\beta$ (also type I IFN) and IFN$\gamma$ (also type II IFN) and tissue growth factor (TGF) $\beta$.

Granulocyte-Macrophage Colony Stimulating Factor or GM-CSF is another non-limiting example of a cytokine in this class that causes the production of macrophages. Thymic hormones both natural and synthetic derivatives are another non-limiting example of receptor ligand class of immune modulators, they are an example of a subclass of receptor ligands that cause division of immature immune mediator cells, in this case thymocytes or premature lymphocytes.

Cytokines modulate target cells by interacting with cytokine receptors on the target cell. Principal cell sources of cytokines include T lymphocytes, B lymphocytes, macrophages, stromal cells, monocytes, leukocytes, and platelets. While cytokine specific receptors are specific for a given cytokine, cytokine receptors are grouped into families based on shared features. The first group of cytokine the hemopoetin group which include immune system cells that bind IL-2, IL-3, IL-4, IL-6 and IL-7. A second receptor family is the TNF receptor family which bind both TNF$\alpha$ and TNF$\beta$. A third family is the immunoglobulin (Ig) superfamily receptor family, which contains an Ig sequence like motif and includes human IL-1 and IL-6 receptors.

See, e.g., Dawson, In *Lymphokines and Interleukins* (Dawson, ed.) CRC Press, Boca Raton, Fla. (1991); Mosmann et al, *Immunol. Rev.* 123: 209–229 (1991); Mosmann et al, *Immunol. Today* 12:A59–A69 (1991); Sherry et al, *Curr. Opinion Immunol.* 3:56–60 (1991); Paul, *Blood* 77:1859–1870 (1991); Dower et al, *J. Clin. Immunol.* 10:289–299 (1990).

A second subclass in this receptor ligand group include lectins. A non-limiting example of a receptor ligand is a monoclonal antibody or fragment capable of binding and/or modulating a receptor, e.g., as a T cell receptor or an IL-2 receptor.

A second class of immune modulators are anti-receptor molecules. These agents can cause the production of antibodies or T cells that can either block receptors on a cell surface or kill such cells in a recipient. As non-limiting examples, one skilled in the art could induce active immunization in a recipient leading to the formation of antibodies or cytotoxic T cells that could, e.g., block lymphokine receptors on a cell, neutralize certain subtypes of antibodies, kill B lymphocytes that make certain subtypes of antibodies, or kill T lymphocytes that have a certain subtype of receptors on their surface.

A third class of immune modulators are transplanted cells, which may include immune mediator cells as defined above that can induce responses by releasing lymphokines or by secreting other molecules. As non-limiting examples these cells can be lymphocytes, macrophages, splenocytes and/or thymocytes. As non-limiting examples the products the transplanted cells release can be lymphokines, as well as heterogenic or allogenic molecules as in proteins, carbohydrates and lipids.

A fourth class of immune modulators are "general immune modulators." These agents also go by other names including immune modulating agents or immune response modulators. Depending on what dose and how these agents are given they can be termed immune potentiators or immunosuppressants. These agents often have the ability to cause non-antigen specific activation of immune mediator cells through the release of lymphokines compared to vaccines that usually cause specific activation of clones with specific affinity for the vaccine antigens. General immune modulators are often used at higher doses than conventional immunogens and/or are typically given at frequent intervals as in every seven days or less. These agent often provide no protection against common pathogens in contrast to many vaccines and other pharmaceutically acceptable conventional immunogens. These agents generally do not employ adjuvants in contrast to vaccine immunogens. Non-limiting examples of immune modulators include the biologic OK-432 and the chemical entities levamisole and isoprinosine.

It should be noted that some agents may be members of more than one of the above groups or classes. As a non-limiting example, a lymphokine may be a conventional immunogen if it is derived from a heterologous species to which it is given as in the case of administering a mouse derived lymphokine to a human. Hybrid or fusion molecules can also be made that contain an biologically active part that has lymphokine activity and another section that contains an conventional immunogen.

Immunogenic Agents

An immunogenic agent (vaccine) of the present invention is a pharmaceutically-acceptable composition comprising at least one immunogen in an amount such that, when administered according to an immunization schedule as disclosed above, it contributes to the desired effect against a chronic immune-mediated disorder, and, in a preferred embodiment, also against an infectious disease. In some embodiments, the immunogenic agent will comprise at least one non-pediatric immunogen and, optionally, one or more pediatric immunogens. In a preferred embodiment, the immunogenic agent may comprise at least one anthrax immunogen, and at least one other immunogen, which may be a pediatric or another non-pediatric immunogen. In another preferred embodiment, the immunogenic agent may contain at least one plague vaccine immunogen and at least one other immunogen, which may be a pediatric or another non-pediatric immunogen.

The term "immunogenic agent" is not intended to cover foods customarily given for nutritional reasons to infants and other children, such as bovine milk, common baby formula, and common baby food, even though such foods may nominally contain "immunogens".

When multiple immunogens, and/or multiple dosings of the same immunogen, are administered, the individual doses of individual immunogens may by themselves be subimmunogenic, provided that in aggregate, when administered according to the schedule, an immunogenic effect is achieved.

Immunogenic agents may be prepared in pharmaceutically acceptable form according to known method steps, based on the teaching and guidance presented herein. Non-limiting examples of preparation of immunogenic agents suitable for use in the present invention include DTP (21 CFR, part 610–630; Mueller et al *J. Immunol.* 56:143 (1947)); tetanus/diphtheria Pillemer et al., *J. Immunol.* 54:213 (1946)); measles/mumps/rubella (U.S. Pat. No. 4,147,772 to McAleer et al); yellow fever (*Morbidity and Mortality Weekly Report* 27:268 (1978); *HHS Publication No.* (CDC) 81–8280, U.S. Gov't Printing Offc., Washington, D.C. (1981)); typhoid (*Morbidity and Mortality Weekly Report* 27:231 (1978)); plague (*Morbidity and Mortality Weekly Report* 27:231 (1978)); Hepatitis B (U.S. Pat. No. 4,129,646, McAleer et al); hemophilus ((U.S. Pat. No. 4,196,192, Kuo); OPV (Eagle, *Science* 122:501 (1955); anthrax (FDA Freedom of Information Act document regarding Michigan Dept. of Health Anthrax Product License Application, 1993), the entire contents of which are herein entirely incorporated by reference.

Such immunogenic agents in pharmaceutically acceptable form may also be prepared according to known method steps using recombinant technology and by the use of monoclonal antibodies and fragments thereof. See, e.g., Ausubel et al, eds, *Current Protocols in Molecular Biology*, Greene Publishing Assoc. and Wiley Interscience, N.Y., N.Y. (1987, 1993); Coligan et al eds., *Current Protocols in Immunology*, Greene Publishing Assoc. and Wiley Interscience, N.Y., N.Y. (1992, 1993); Sanbrook et al infra, are Harlow, infra.

A hepatitis B vaccine may be recombinant or produced from blood products. A polio immunogen may be a live and or killed immunogen. A polio vaccine may be trivalent such that the vaccine may induce in mammals antibodies reactive to three serotypes of polio virus. A hemophilus influenza immunogen may be a conjugated and or unconjugated immunogen. A pertussis immunogen may be a non-whole cell or a whole cell immunogen. The non-whole cell immunogen may include a cellular pertussis immunogen.

Purification of vaccine immunogens helps minimize the presence of impurities in a vaccine. Purification may be performed by any method that produces an highly pure end product as in the non-limiting examples of: chromatography, electro-kinetic processes, membrane processes, centrifugation, and extraction (Biotechnology 5:789–793). Extensive reviews of separation techniques are included in several different texts including the book by Juan A. Asenjo, Separation Process in Biotechnology, published Marcel Dekker Inc., New York (1990) (see especially Chapters 19, 20). The preferred method of purifying an non living vaccine antigen would be one that can inexpensively produce highly pure end products with minimal loss of vaccine immunogen in the process. An example of a preferred method would be purification using affinity chromatography where a column contains a ligand that has high specificity, high binding capacity for thee target antigen and said antigen can be eluted from said column under conditions that do not degrade the product or the column. In a preferred method a step should be added to ensure the removal of fragments of the desired immunogen that retain the ability to bind to the affinity column.

A vaccine should preferably contain as few impurities as possible, as well as maintain a very high consistency of the amounts and ratio of vaccine components including immunogens and adjuvants in each dose with little or no lot-to-lot variation. Vaccine immunogens should preferably be characterized by their unique physical properties to allow their composition in a vaccine to be measured. The movement of an vaccine or its immunogenic components through a gel as in the non-limiting examples of chromatography or electrophoresis will allow detection of bands of impurities in the vaccine. In a preferred embodiment the total amount of impurities comprising molecules unrelated to the desired vaccine components should be less than 0.5% by weight and even more preferably less than 0.1%. The desired vaccine antigens should preferably be defined by molecular weight and molecules should preferably differ by less than 5% of this number or be considered separate immunogen. The variation in the amount of an particular defined vaccine component as in the non limiting examples of an immunogen or adjuvant in a dose should preferably be less than 2% by weight. A non-limiting example of how vaccines are currently tested for purity is described in a paper on manufacturing of Neisseria meningitis vaccines (Avshalom Mizrahi, Bacterial Vaccines, Alan R. Liss Inc. (1990), pages 123–145) and differences to the current inventions are clear.

In addition to the immunogen, the pharmaceutical composition may contain suitable pharmaceutically acceptable carriers, such as excipients, carriers and/or auxiliaries which facilitate processing of the active compounds into preparations which can be used pharmaceutically.

Such carriers may include depot adjuvants that release an immunogen in vivo over a prolonged period as compared to administration of an unbound immunogen. Preferably the depot adjuvant comprises an aluminum, calcium or salts thereof, such as aluminum sulfate (alum), aluminum phosphate, calcium phosphate or aluminum hydroxide, see, e.g., Gregoriades, G. et al., *Immunological Adjuvants and Vaccines*, Plenum Press, New York, 1989. Depot adjuvants may prove especially useful in connection with diphtheria, tetanus, pertussis, hepatitis B, hemophilus influenza, and polio vaccines.

Another non-limiting example of a preferred ingredient is one that targets and/or activates macrophages, such as a liposome. See, Michalek, S. M. et al., Liposomes as Oral Adjuvants, *Curr. Top. Microbiol. Immunol.* 146:51–58 (1989).

Pharmaceutical compositions comprising at least one immunogen useful according to the present invention may also include suitable solutions for administration, intramuscularly, intravenously, subcutaneously, dermally, orally, mucosally, or rectally or by any other injection, and contain from about 0.001 to 99.999 percent, preferably from about. 0.20 to 75 percent of active component (i.e. the immunogen) together with the excipient. Compositions which can be administered rectally include suppositories. Preparations of immunogenic agents for parenteral administration include sterile aqueous or non-aqueous solutions, suspensions, and emulsions, which may contain auxiliary agents or excipients, such as suitable adjuvants, which are known in the art. Pharmaceutical compositions such as tablets and capsules can also be prepared according to routine methods. See, e.g., Berker, supra, Goodman, supra, and Avery, supra, which are entirely incorporated herein by reference, included all references cited therein.

The immunogenic agents of the present invention may optionally include immunomodulators other than immunogens. Such immunomodulators may also be administered separately as a part of the program.

The compositions of the present invention may also include pharmaceuticals whose primary activity is non-immunological. Said non vaccine pharmaceutical agent may be of any class of pharmaceutical agents including the non limiting examples of agents to ameliorate the following diseases: infectious, cardiovascular, gastrointestinal, endocrine/hormonal, renal, neurological, psychiatric, muscular, skeletal/orthopedic, hematological, hepatic, pancreatic, metabolic, neoplastic, inflammatory/rheumatic, reproductive, dietary/nutritional, ophthalmologic, otologic, pulmonary/respiratory, dermatologic, allergic, and surgical as in anesthetics. See Physicians Desk Reference, Medical Economics Data Production Montvale, N.J. (1994); United States Pharmacopeia; European Pharmacopoeia; Gilman et al, Goodman and Gilman's The Pharmacological Basis of Therapeutics, Macmillan Publishing Company, New York (1985). Preferably, these pharmaceuticals are ones which, when screened as taught herein, are shown to help reduce the incidence or severity of a chronic immune-mediated disorder, or at least do not worsen the disorder.

The term "pharmaceutically acceptable" has both a legal definition and a clinical definition. The code of federal regulations (21 CFR Part 600) legally defines what make an agent "pharmaceutically acceptable." Non-pharmaceutically acceptable products may be contaminated with agents, such as endotoxin or other pyrogens, the presence of which can have profound adverse effects on the immune system of the recipient. Results from immunologic experiments using an non-pharmaceutically acceptable agent e.g., a lymphokine contaminated by endotoxin, may be quite different from an identical experiment using said lymphokine produced under GMP which lacks said impurities.

An immunogenic agent that meets the legal definition of "pharmaceutically acceptable" must further meet the clinical definition of "pharmaceutically acceptable". A clinical definition of pharmaceutically acceptable, as used herein, requires that said agent has a sufficiently beneficial clinical effect when used in a pharmaceutically acceptable dose.

A pharmaceutically acceptable dose, as in total dose, is a dose where the clinical benefits of said product outweighs the toxicity at said dose. Non-limiting examples of said toxicity include acute or subacute reactions like fever, shock or seizures, which may lead to permanent sequela and chronic toxicity like cancer, as is known and recognized in the relevant arts. A pharmaceutically acceptable dose according to this definition can vary according to the severity of the illness being modulated by the immunogenic agent. It is logical that a high dose of an agent which causes significant toxicity may be pharmaceutically acceptable for treating a life threatening malignancy yet the same dose would not be pharmaceutically acceptable for treating a benign disorder like a common sore throat. Following said logic, vaccination or other regimens to prevent diseases in healthy individuals usually employ non toxic doses. In the case of vaccinations, permanent sequelae as infrequent as one in 300,000 following immunization, as is believed the case with the whole cell pertussis vaccine, may be considered unsuitable by some.

A pharmaceutically acceptable, dose will depend on the structure of the particular agent and/or the condition or genotype of the recipient. Some agents may be more toxic than others while some may be more immunogenic than others. In a like manner some individuals are more responsive to a given dose while others may be more sensitive to the toxic effects at that dose. There is thus an individual variation within the definition of pharmaceutically acceptable dose as well as species, racial, age, and population variation, all of which should be taken into account when dosing an individual. Such consideration has, of course, been given to other prophylactic agents.

The term pharmaceutically acceptable dose as defined herein may also incorporate an economic definition. A pharmaceutical acceptable dose in terms of preventing disease is one where benefit to society approximates or is greater than the cost of administering the agent. Said cost of administering the agent may include the cost of the agent, the necessary supplies as in needles, any transportation needed to bring patient, and the staff expenses needed to administer said agent, maintaining an administration clinic, as well as the costs associated with or resulting from adverse reactions to the agent. The benefits to society include savings from reductions in costs associated with the diseases that are prevented in society include one or more of lost productivity, medical expenses, expenses related to the care of the disabled person and some or all complications stemming from the illness. As a non-limiting example a pediatric vaccine that costs a society one trillion dollars a year to administer might not be considered pharmaceutically acceptable for a disease that costs said society ten million dollars a year.

A pharmaceutically acceptable dose must usually be determined by performing screening tests for both efficacy and safety. Data presented herein shows that doses of vaccines approximating that used to protect humans against infectious diseases (immunogenic doses) were also effective in preventing chronic immune mediated disorders in certain mammals. Pharmaceutically acceptable immunogenic doses for many of the preferred agents presented herein are thus readily available through common references with an non-limiting example being the physician's desk reference, manufacturers product inserts, and scientific literature referenced through a database like MEDLINE. The immunogenic doses mentioned in the reference may be adjusted for the size of the recipient. A screening method as described herein may be used to calculate a pharmaceutically acceptable and immunogically acceptable dose.

The term pharmaceutically acceptable dose includes a supraimmunogenic dose. The lowest dose of immunogen effective in protecting the recipient against an infectious disease is termed the immunogenic dose. Using higher doses than the immunogenic dose results in a higher morbidity and mortality caused by the immunization than the additional morbidity and mortality, related to the infectious disease, prevented by using the higher dose. The current invention teaches that doses above the immunogenic dose may lead to enhanced protection against chronic immune mediated disorders.

A supraimmunogenic dose may be defined in several ways. One definition may be a dose that is higher than has been used to induce an protective immune response against the intended pathogen in recipients of a given age/size. The immunogenic dose can be determined from art describing immunization against infectious diseases, as described herein. A second definition of supraimmunogenic dose may be a dose higher than necessary to prevent an infectious disease, where the enhanced toxicity associated with using the higher dose is greater than any measured benefit in preventing the intended infectious disease derived from using the higher dose. The toxicity and benefit may be determined by calculating the number of people expected to develop vaccine related toxicity and the number expected to be spared from the sequela of the infection disease that the vaccine prevents, where the toxicity and benefit may be quantitated into short term, moderate, and permanent sequelae. The toxicity and benefit may also be calculated financially as described herein.

It is understood that the dosage of an immunogenic agent of the present invention administered in vivo or in vitro will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the most preferred dosage will be tailored to the individual subject, as is understood and determinable by one of skill in the art, without undue experimentation. In the context of the present invention "one dose" may include concurrent or separate administration of more than one immunogen comprised of an immunogenic agent according to the present invention. See, e.g. Berkow et al, eds., *The Merck Manual*, 16th edition, Merck and Co., Rahway, N.J., 1992; Goodman et al., eds., *Goodman and Gilman's The Pharmacological Basis of Therapeutics,* 8th edition, Pergamon Press, Inc., Elmsford, N.Y., (1990); *Avery's Drug Treatment: Principles and Practice of Clinical Pharmacology and Therapeutics,* 3rd edition, ADIS Press, LTD., Williams and Wilkins, Baltimore, Md. (1987), which references and references cited therein, are entirely incorporated herein by reference.

The total dose, as in a pharmaceutically acceptable dose, required for each treatment may be administered by multiple doses or in a single dose. An immunogenic agent may be administered alone or in conjunction with other therapeutics directed to immunologic disorders, such as allergies, immune mediated cancers and autoimmune pathologies, as known in the art.

The pharmaceutically acceptable dosage of the immunogene will usually be about 0.01 $\mu$g to about 5 mg of immunogen, per kg body weight, and preferably from about 0.1 $\mu$g/kg to about 1 mg/kg body weight, still more preferably about 1 $\mu$g/kg to about 300 $\mu$g/kg, most preferably about 10 $\mu$g/kg to about 100 $\mu$g/kg. Nevertheless, Applicants' invention is not limited to the dosages set forth above. The active agent is the at least one immunogenic agent that induces an immune response according to the present invention. The safe dose will vary depending on the agent. Some immunogens are toxic at low doses while others are not.

Kits

The present invention also encompasses kits for administration of one or more immunogens according to methods of the present invention. Such kits may provide receptacles of immunogenic agents in forms suitable for pharmacologic administration, as described herein or as could be provided by one skilled in the art based on the teaching and guidance presented herein, without undue experimentation. Preferred examples of such forms for administration are for oral or injection administration. Such kits may include, as non-limiting examples, at least one immunogenic agent comprising an anthrax or plague immunogen and at least one other immunogen corresponding to a different organism and or disease selected from the group consisting of diphtheria, pertussis, measles, mumps, rubella, small pox, pneumococcal, CMV, HIV, meningitis, tetanus, *hemophilus influenza,* hepatitis B, hepatitis, cholera, varicella, typhoid, yellow fever, neisseria, plague, adenovirus, hepatitis C, herpes, anthrax, plague, malaria, rabies, and/or polio virus immunogen, or a molecule that cross reacts immunologically to the immunogens. Another non-limiting example of such kits includes at least one non-pediatric immunogen and at least pediatric immunogen. Optionally and preferably the kits are in the form of a pharmaceutical composition optionally further comprising a pharmaceutically acceptable carrier, such as a vaccine adjuvant or a depot adjuvant, such as aluminum, calcium or a salt thereof.

Pharmaceutical Administration

The immunogenic agents of the present invention may be administered by any effective route, for example, by various parenteral routes such as subcutaneous, intravenous, intradermal, intramuscular, intraperitoneal intranasal, transdermal, or buccal routes. Alternatively, or concurrently, administration may be by the oral route. A preferred mode of using an immunogenic agent or composition of the present invention is by intra muscular application.

Screening Methods for Determination of Whether Particular Immunogens, Immunogenic Agents and/or Immunization Schedules Affect the Incidence of Severity of A Chronic Immune-Mediated Disorder.

The present invention also provides methods for screening potentially pharmaceutically acceptable immunogenic agents and or dosing regimens for their suitability and effectiveness in preventing at least one chronic immune mediated disorder and at least one infectious disease. One skilled in the art can perform any of the following screening methods or as few as desired to determine information sought by the investigator. The preferred order of performing the screening methods is listed below, however, one can perform the methods in any order that best suits the investigator. The term potentially pharma-ceutically acceptable implies that the agents are not associated with any toxicities, at doses that they are being used in the screening methods, that would prohibit their use.

The methods may be adapted to screen for the ability of a immunization schedule containing one or more potentially pharmaceutically acceptable immunogens and, optionally, one or more potentially pharmaceutically acceptable immune modulators, to prevent both chronic immune mediated diseases and infectious diseases. Immune modulators may be substituted for one or more immunogens in the following methods where applicable. Appropriate doses of immune modulators to use can be calculated from references cited herein, references found in Medline/Index Medicus or other suitable database, and for new immune modulators one can use doses by weight approximating those used for immunogens.

Suitable screening methods, such as described herein, will allow one skilled in the art to determine (a) if a substance is an immunogen; (b) if it is effective in preventing disease; (c) if it has a safe and effective range; and (d) if said agent modulates at least one chronic immune mediated disorder in mammals that already receive immunogens early in life to protect against infectious diseases. For immunogens thus shown to be useful, one may further determine a safe and effective immunogenic agent and/or dosing regimen utilizing said immunogen, alone or with others. After an effective immunization schedule is determined, the screening methods may be used to verify the effectiveness of vaccine lots for the purpose of preventing or alleviating a chronic immune-mediated disorder.

Alternatively, a screening trial may be designed to determine if an immunization schedule, such as a standard schedule known in the art, will induce and/or enhance the incidence and/or severity of at least one chronic immune mediated disorder. In the latter case, it may be especially useful in screening production lots of approved vaccines for the hitherto unrecognized safety problem of inducing or exacerbating a chronic immune-mediated disorder.

The preferred method for finding immunogens suitable for use in the present invention is to start with an extract derived from at least one foreign organism, such as a bacteria, virus, fungus, insect, plant, allogenic or xenogenic animal. A simple screening test for determining if an agent is an immunogen is to inject the agent subcutaneously in an mammal, such as a mouse, and looking for the development of inflammation at the injection site as well as the development of antibodies to the agent. Suitable sites include paw pads and ears. Mammals that appear to have an immune response can have blood drawn and checked for anti-bodies to the agent. An ELISA is an simple assay that can be used to screen many animals for antibodies very quickly. Delayed type hypersensitivity assay can be performed for determining if the agent induces a cellular immune response. Controls can be made by using animals that receive only the vehicle used to suspend the potential immunogen in question.

In vitro assays can also be developed to screen for potential immunogens. These assays are best suited for screening immune modulators like lymphokines, and certain monoclonal antibodies believed to have immune regulatory effects. As a non-limiting example, splenocytes, thymocytes or lymphocytes can be cultured in a 96 well plate with supportive media. Uptake of tritium labeled thymidine 48–72 hours after the addition of an potential immunogen can suggest the activation and proliferation of immune mediator cells, suggesting that said agent is an immunogen.

Once an agent has been confirmed to be an immunogen, a screening study can be performed to determine its effectiveness in preventing at least one chronic immune mediated disorder. High doses of the immunogen are recommended initially so that an effect due to using too low a dose is not missed. Preferred starting dose is 1 to 2 mg/kg body weight. A preferred method is to give autoimmune prone mammals intraperitoneal injections with the agent starting within 10 days of birth and continuing every 2 weeks for 4 injections. Control animals can be injected with phosphate buffered saline or any vehicle that the immunogen is dissolved in. Blood can be drawn from the mammals and checked for the presence of hyperglycemia in diabetic prone mammals or autoantibodies in autoimmune prone mammals that develop antibody mediated disease. Tissue from the study mammals can be removed and histology can be performed to determine if the tissue is affected by chronic immune mediated disorders. Non-limiting examples include pancreatic islet cells in diabetes prone mammals or gastric fundi in mammals prone to develop autoimmune gastritis. Histology is generally a less sensitive assay than ELISA assays for autoantibodies or blood glucose for diabetes. All results in the treated group can be compared to the control mammals.

Preferably, immunogens are screened for the ability to react to the recipient's sera. Preferably the sera from individuals, not pooled, should be screened. Many methods have been developed to determine if antibodies react to an antigen. Any method that performs the desired function is suitable. Antibody titers can be determined to quantitate the antibodies in sera that react to the immunogen. As an alternative method, maternal serum, from the potential recipient's mother, may be screened since the recipient often receives maternal antibodies which cross the placenta.

Several screening methods lend themselves very well to determining if the agent has effects on inhibiting chronic immune mediated disorders. Non-obese diabetic (NOD) mice or Bio Breeding (BB) rats can be used to screen an agent for effectiveness in preventing diabetes. Mice can be injected as above and blood drawn to check for hyperglycemia at monthly intervals through the first 6 months of life. Ten or more female NOD mice will give an quick first approximation of an effect. Detailed methods are provided in examples 1 and 2 below. Other possible methods of screening agents for their effectiveness in preventing chronic immune mediated diseases beside diabetes also exist. Cyclosporine induced autoimmunity, e.g., as demonstrated in example 3, is one method for screening agents for their ability to inhibit organ specific autoimmune disease like gastritis. Different strains of mice are more prone to develop certain autoimmune diseases when they are altered then others (Kojima and Prehm, 1981). One can pick a strain depending on what disease one wants to look at.

Other immunosuppressing regimens besides cyclosporine can be used to create disease in animals that can be inhibited by vaccination. Non-limiting examples include immunosuppressive monoclonal antibodies (Journal of Experimental Medicine 166:461–475), other noncyclosporine immunosuppressants should preferably be given for the first week of life as in Example 3 and then vaccines may be administered. Other rodents that can be used to screen for vaccine prevention of autoimmunity include the non-limiting examples of MRL/1pr (see Example 5) and NZB/NZW mice which spontaneously develop rheumatoid diseases that resemble lupus and rheumatoid arthritis.

Blood can be screened for autoantibodies using ELISA assays as described in example 3 below. There is a large number of ELISA assays that have been published in the scientific literature and these can be found looking through index medicus or a similar computer file referencing autoantibodies and the particular autoantigen or organ system one wants to study. See also Ausubel, supra, Coligan, supra, Harlow, supra.

One skilled in the art may determine if an agent can alter the incidence, prevalence, frequency and or severity of a chronic immune mediated disorder by studying the effect of said agent on surrogate markers of said disorder. Theses markers may include the presence of lymphokines, autoantibodies, markers of cell destruction as in the non limiting example of increased levels of certain enzymes in the blood, indicators of abnormal endocrine function as in the non limiting example of abnormal glucose tolerance test or thyroid function test, autoimmune lymphocyte clones, certain immune mediator or inflammatory cells associated with increased risk of autoimmunity which correlate with toxicity. See Isselbacher et al. editors, Harrison's Principles of Internal Medicine, McGraw-Hill, New York (1994); Rose, N. R et al. editors, Manual of Clinical Laboratory Immunology, American Society for Microbiology, Washington, D.C. (1992); Roitt, Ivan Maurice et al. editor, Encyclopedia of Immunology, Academic Press, London (1992); Miller, Linda E. et al., Manual of Laboratory Immunology, Lea & Febiger, Philadelphia (1991); Bona, Constantin A. et al.; Molecular Immunobiology of Self-reactivity, Dekker, New York (1992), Talal, Norman, Molecular Autoimmunity, Academic Press London (1991); Bouloux, Pierre-M. G. et al., Diagnostic Tests in Endocrinology and Diabetes, Chapman & Hall Medicine, London (1994); Noe, Dennis A et al. Laboratory Medicine: The Selection and Interpretation of Clinical Laboratory Studies, Williams & Wilkins, Baltimore (1994); Tilton, Richard C. et al., Clinical Laboratory Medicine, Mosby Year Book, St. Louis, (1992); Paul William E., Fundamental Immunology, Raven Press, New York (1993).

Agents that have been shown to effectively inhibit chronic immune mediated disorders at high doses may be screened to determine what doses if any may be safely administered to an mammal. Routine toxicology tests, as those requested by a regulatory agency such as the FDA, can be performed at varying doses to determine an safe dosing range. Non limiting examples of such tests include mutagenesis, carcinogenesis, acute toxicity on vital organs such as the kidneys, lung, heart, liver, and brain, chronic toxicity of the organs, as well as defining a lethal dose.

The present invention also pertains to a method to screen vaccines to determine their propensity to induce diabetes mellitus or chronic immune mediated disorders like autoimmune diseases. A group of autoimmune prone mammals may be given an agent in the first months of life, as an non-limiting example, a less strong immunogen, to reduce the incidence of autoimmunity in those mammals. A diphtheria/tetanus vaccine is a preferred embodiment and the dose used is expected to reduce the incidence of autoimmunity by 50%–75% compared to untreated mammals, but should preferably not completely inhibit autoimmunity. A second group of autoimmune prone mammals should receive the same immunogen and dose, but should receive the vaccine in question at approximately 2 months of age or later, with 2 months preferred. The incidence of diabetes or autoimmunity should be noted in each group. Safety should be assessed by determining the incidence or prevalence of disease in the two groups. An example of the method is demonstrated in example 2, where the diphtheria tetanus vaccine is given to 2 groups of NOD mice but one group also received an additional administration of pertussis vaccine at approximately 2 months of age. The later group developed a higher incidence of diabetes suggesting that pertussis vaccine can have a toxic effect by inducing diabetes. Non limiting examples of other possible autoimmune prone mammals that can be used in the screening method include cyclosporine-treated mice, see Example 3 below, and day-3 thymectomized mice.

The mammals in the previous methods should be raised in an pathogen-free environment as a preferred embodiment. A non limiting example of an suitable environment includes housing animals where the caging, bedding, food and water are all autoclaved, the cage has filters to prevent pathogens from entering the cage. As an preferred environment the cage should only be opened under a laminar flow hood equipped with filters to trap pathogens. The use of an pathogen free environment prevents mammals from exposure to natural immunogens that may effect the interpretation of the results.

The present invention also pertains to a method to screen potentially pharmaceutically acceptable immunogens to determine their propensity to modulate at least one chronic immune mediated disease in mammals that live in open environments, as opposed to pathogen free environments, which receive extensive exposure to both pharmaceutically acceptable and natural immunogens early in life. In said method, mammals will typically receive at one vaccine at less than 96 months of age where the agent is capable of preventing an infectious disease caused by an infectious agent or capable of inducing neutralizing antibodies to the infectious agent. In the screening method the dosing regiment to prevent at least one chronic immune mediated disorder and at least one infectious agent is termed an immunization protocol.

The screening method may involve administering at least one potentially pharmaceutically acceptable dose of at least two potentially pharmaceutically acceptable immunogenic agents comprising at least one potentially pharmaceutically acceptable pediatric immunogen and at least one agent selected from the group consisting of a second pediatric immunogen and a non-pediatric immunogen, for the ability to modulate the development of at least one chronic immune mediated disorder and or of at least one surrogate marker of the chronic immune mediated disorder in a population and or subpopulation of mammals. The method comprising administrating to at least one treatment group of at least one mammal at risk for at least one chronic immune mediated disorder at least one treatment dose of immunogenic agents according to a treatment administration schedule. The at least one treatment dose may comprise at least a first treatment dose of at least one of the immunogenic agents administered prior to an age of 56 days of the mammal.

One or more control groups of at least one mammal may be defined optionally. The control groups may receive at least one control dose which contains at least one potentially pharmaceutically acceptable pediatric vaccine and has at least one modification selected from the group consisting of: (i) lacking at least one immunogenic agent/adjuvant than as is provided in the treatment schedule; (ii) including at least one immunogenic agent/adjuvant than as is provided in the treatment schedule; (iii) including a higher dose of at least one immunogenic agent/adjuvant than as is provided in the treatment schedule; (iv) including a lower dose of at least one immunogenic agent/adjuvant than as is provided in the treatment schedule; (v) including at least one additional dose of at least one immunogenic agent/adjuvant than as is provided in the treatment schedule; (vi) lacking at least one dose of at least one immunogenic agent/adjuvant than as is provided in the treatment schedule; (vii) including at least one dose of at least one immunogenic agent/adjuvant at a later time than the immunogenic agent/adjuvant is administered in the treatment schedule; (viii) including at least one dose of at least one immunogenic agent/adjuvant at an earlier time than the immunogenic agent/adjuvant is administered in the treatment schedule; and (ix) no modifications from the treatment schedule wherein at least one measure in the group consisting of incidence, prevalence, frequency, and severity of at least one chronic immune mediated disorder and or of at least one surrogate marker of the disorder can be/has been determined in the control group. The term immunogenic agent in this paragraph refers to an immunogen that is unbound or administered with a particular pharmaceutical carrier at a definable ratio as described herein. The terms treatment schedule and treatment administration schedule are used interchangeably herein.

Participants may be screened to determine the modulation of development of the at least one chronic immune mediated disorder by at least one of the treatment administration schedules. The determining step may comprise ascertaining at least one measure from the group consisting of incidence, prevalence, frequency and severity of at least one chronic immune mediated disorder and or of at least one surrogate marker of the disorder in at least one mammal in at least one treatment group and optionally the same measures in at least one mammal in the one or more control groups. Historical controls may be used in place of experimental controls.

A control group in one screening trial may be the treatment group in the next or vice versa. In a preferred embodiment., a control group is used which contains mammals that receive an currently recommended immunization schedule as in the non-limiting examples of the schedules recommended by the Centers for Disease Control (CDC) and the American Academy of Pediatrics.

Comparison of data from the one or more control groups to data from the at least one treatment group may be performed to determine if the treatment schedule can modulate at least one measure in at least one chronic immune mediated disorder. In a preferred embodiment the size of the groups should allow determination of statistical significance during an acceptable period of time. Any statistical method that is deemed appropriate for the trial design by one skilled in the art may be acceptable.

In order to select an appropriate size of the treatment and control groups it is first helpful to know the incidence/prevalence/frequency/severity of the chronic immune mediated disorder and or surrogate marker of the disorder in children. Given the desired change in incidence of disease one hopes to be able to detect, and the statistical test one is employing, one can determine the size of a population needed for the at least one treatment group and the one or more control groups to demonstrate statistical significance ($p<$ or $=0.05$).

It is preferred to perform the screening method in a developed country where the exposure to pathogens is reduced during the first year of life. Developed countries have expensive water purification and sewer systems that reduce an infant's exposure to the pathogens. The method should preferably allow one skilled in the art to determine if the treatment administration schedule prevents, induces, or has no affect over the currently recommended immunization schedule.

Developed countries may include the United States, Canada, and the European nations listed in the table pertaining to Example 101. A country may be considered developed if it has both a per capita income greater than or equal to any of the above countries, and nationwide water purification systems as well as sewage treatment systems which equal or surpass that in the above nations.

The mammals of the screening methods may include as non limiting examples rodents such as NOD mice and BB rats, and primates such as humans.

A human study population will preferably contain individuals who are at risk for development of the chronic immune mediated disorder. For example, in the case of diabetes mellitus, it will preferably include at least 25% Caucasians of European descent. Caucasians of European descent have a high rate of diabetes and certain autoimmune diseases as compared to other groups like Japanese and this invention shows that occurrence of diabetes in European Caucasians is sensitive to vaccination.

The screening method may be retrospective, prospective or contain data derived both retrospectively and prospectively. Individual mammals may be placed in a particular study group based a selection process that is either random, non random or both, however random selection is the preferred method. Participants, their families, and researchers may be either blinded, unblinded or both to the immunization schedule. The endpoints of the screening method may be the diagnosis of at least one chronic immune mediated disorder and or surrogate marker of the disease in an individual. The preferred embodiment is to use at least one disease that develops early in life, is relatively frequent, and has a clearly defined endpoint with the non limiting example being type I diabetes mellitus.

By using the combination of several diseases as an end point the number of participants needed to show a statistical effect is reduced and the time to detect an effect is reduced. Prior to this invention it was not accepted that pharmaceutical acceptable doses of pharmaceutically acceptable immunogenic agents could prevent one chronic immune mediated disorder, much less several such disorders.

It is often easier to compare people in different countries because most people in a given country tend to receive the same vaccines, so it is hard to get an unbiased division of those who received from those that did not receive vaccine. Governments' decisions on whether to promote immunization of the citizens with a particular vaccine like BCG is often ambiguous. Thus one can have a situation where genetically and culturally similar people live on opposite sides of a national border and one group of citizens receives a particular vaccine and another nationality does not receive the vaccine or receives it at a different age.

Another non-limiting example of using retrospective data to screen an pharmaceutically acceptable immunogen for the ability to modulate a chronic immune mediated disease is to study the effect of changing an immunization schedule on the incidence of disease. In places where the immunization schedule has changed as in the case of Finland, see Example 101 discussed herein, one skilled in the art can study the effect of the change on the development of at least one chronic immune mediated disorders. The incidence/prevalence/frequency/severity of the at least one disorder and or surrogate marker of the at least one disorder prior to the change may be determined retrospectively and or prospectively and the parameters of the at least one disorder after the change may be determined prospectively and or retrospectively.

One skilled in the art may also perform prospective screening methods. As a non-limiting example mammals in a treatment group may receive one immunization schedule and mammals in a control group may receive a different immunization schedule as described above. The incidence/prevalence/frequency/severity of at least one chronic immune mediated disorder and or at least one surrogate marker of the at least one disorder is determined prospectively in each group. A nonlimiting alternative to the example is where the data from one group may be determined retrospectively and the data from another is determined prospectively.

The screening method may be designed to control for and or estimate the effects on at least one mammal in at least one treatment/control group from at least one confounding variable. For example, one may consider the effects of receiving breast feeding versus bottle feeding prior to 12 months of age, receiving antibiotics during the first 12 months of life, the maternal age at birth, the presence of a chronic immune mediated disorder in the mother/father/a close relative, maternal infections while the mammal was in utero, infections during the first 12 months of life, size of the mammal at birth, gestational age of the mammal at birth, exposure of the mammal to BCG vaccine or naturally acquired mycobacterium, and exposure to various vaccines or pathogens.

Studies may give misleading results on a vaccine's safety if one does not take into consideration that having a disease like measles may be associated with a higher incidence of a chronic immune mediated disorder than receiving the vaccine for the disease. A vaccine may induce chronic immune mediated disorders but at a lower rate than the infectious agent it protects against.

One may design the trial to control for and or determine the difference in at least one chronic immune mediated disorder between a group which received a vaccine but did not develop the infectious disease which the vaccine protects and a group that did not receive the vaccine but also did not develop the infectious disease. The difference in at least one chronic immune mediated disorder may include at least one measure in the group consisting of incidence, prevalence, frequency, and severity of at least one chronic immune mediated disorder and or of at least one surrogate marker of the at least one disorder. Type I diabetes mellitus is the preferred chronic immune mediated disease to study for reasons mentioned above.

The optional one or more control groups may receive an administration of at least one potentially pharmaceutically acceptable pediatric vaccine prior to the age of 56 days of the; at least one mammal.

The treatment group may receive at least one dose of at least one immunogenic agent/adjuvant not administered to at least one control group.

One may use several different methods to determine if an mammal develops protection against at least one infectious disease for which the at least one mammal received immunization against in the pediatric age as defined earlier. In a non-limiting example one can determine the incidence/prevalence/frequency/severity of the at least one infectious disease in the at least one treatment/control group in question and determine if the group received adequate protection from the at least one infectious disease. In an alternative method members of the group in question may be screened for the development of a protective level of antibodies to the causative infectious agents. As a non limiting example the level of protection may be compared to at least one of the following: (i) a group that received no protection/immunization, (ii) a group that receives a recommended immunization schedule, (iii) an rate that is deemed acceptable by professionals in the field as in those affiliated with the Centers for Disease Control, the American Academy of Pediatrics and or the FDA.

The size of a group needed to determine if an dosing schedule provides protection against at least one infectious agent is generally smaller than that needed to detect an effect on reducing a chronic immune mediated disorder because the incidence of the former diseases are generally higher than the later diseases and the former may occur earlier in life than the later. If the end point of the study is the development of protective or neutralizing antibodies two hundred mammals or less may be sufficient. The trial preferably will utilize any statistical method that is acceptable and is congruent with the study design.

Methods of the present invention may also be used to screen non-vaccine pharmaceutical agents for either their ability to induce a chronic immune-mediated disorder including spontaneous immune-mediated diabetes mellitus and/or to interfere with a vaccines' effect on a chronic immune-mediated disorder. One skilled in the art will be readily able to adapt these methods to perform the desired task, by substituting the non-vaccine pharmaceutical for the vaccine in the above-methods.

However, one need not determine if said pharmaceutical prevents at least one infectious disease. In the case where said pharmaceutical is screened for the ability to interfere with a vaccines' effect on a chronic immune-mediated disorder, said pharmaceutical may be given with a vaccine and the results can be compared to an otherwise identical experiment where only the vaccine is administered. In a prefered embodiment, the chronic immune mediated disease is diabetes mellitus. Said non-vaccine pharmaceutical agent may be of any class of pharmaecutical agents. The pharmaceutical product may be one other than an immunosuppressant, an agent to regulate blood sugar, and/or an immune stimulant.

Methods and Products for Late and Booster Immunization

The present invention also encompasses compositions and methods to administer vaccines after 8 weeks of age without significantly inducing an chronic immune-mediated disorder. Animal and human epidemiology data described herein show that the administration of vaccines starting after 8 weeks of life can induce chronic immune-mediated disorders including type I diabetes mellitus. Currently there are no ways of starting immunization after 8 weeks or providing boosters to older children without a substantial risk of inducing diabetes. Compositions and methods described below may preferably be used for starting immunization after 8 weeks of age, administering a booster when the mammal has not received a vaccine in the prior 3 weeks, and administering vaccines when the recommended administration schedule in the first 4 months of life was not complete.

Preferably, the subject is first screened for the adequacy of his or her protection against the infectious diseases against which immunization was considered desirable; if adequate, immunization is contraindicated as it could increase the risk of inducing or exacerbating a chronic immune mediated disorder.

Next, the subject is preferably screened for the presence of a clinical or sub-clinical chronic immune-mediated disorder, positive subjects are not good candiates for immunization that could worsen their condition.

If the subject is still to be first immunized with a particular immunogen after eight weeks of age, the risk of thereby eliciting a chronic immune-mediated disorder can be blunted by using weaker immunogenic agents, administering an immunosuppressant, or administrating a glucocorticoid hormone (or analogue), or a substance which induces glucocorticoid release.

Screening for a protective immune response and a chronic immune mediated diseases may be performed in sequence or jointly. Body fluids may be screened for the presence of antibodies in levels indicating said mammal has sufficient protection against an infectious disease and if the mammal does not have sufficient protection then said body fluids may be tested for indicators of at least one chronic immune mediated disorder and or risks of developing said disorder. Alternatively body fluids can be screened for both the presence of antibodies in levels indicating said mammal has sufficient protection against said infectious disease and for indicators of at least one chronic immune mediated disorder and or risks of developing said disorder. The preferred body fluid is blood or a derivative of blood as in serum or plasma. Other body fluids that may be used include as non limiting examples saliva, urine, tears, and lymph. Said indicators of at least one chronic immune mediated disease and or risks of developing said disorder may include the following non limiting examples: autoantibodies, lymphocytes containing certain T cell receptors, autoimmune lymphocyte clones, certain MHC types associated with increased risks for developing autoimmunity, certain immune mediator or inflammatory cells associated with increased risk of autoimmunity, an abnormal glucose tolerance, ongoing tissue destruction, and endocrine abnormalities.

Screening may be performed in a clinic and or physician's' office to give immediate results or an specimen as in the preferred embodiment but non limiting example of blood may be removed from the patient for analysis at a later time or different sight. Screening may measure humoral immune responses or cellular immune responses. The latex bead agglutination test is a preferred method of detecting humoral immunity and auto antibodies because it is fast, sensitive, specific, simple, and inexpensive. Other non limiting examples of acceptable ways to detect antibody levels include ouchterlony analysis, radial immunodiffusion, electroimmunodiffusion, immunoelectrophoresis, radioimmunoassays, ELISA, complement fixation tests, other agglutination reactions, cytotoxic assays, immunfloresecence, radioactive binding assays, immunoferritin or other electron-microscopy techniques, flow cytometry, hemolytic plaque assays. The preferred method of testing cellular immunity is through skin testing however more complicated techniques using cell culture would also work. In a preferred embodiment the test are performed from a single sample of blood however several blood specimens taken from the patient in a short time span as in less than 72 hour period would also be readily acceptable.

The methods above can be utilized by one skilled in the art to determine the degree of protection against an infectious disease and or the risk of developing a chronic immune mediated disease. One skilled in the art as in the non limiting example of a physician may use this data to determine appropriate administration of vaccines. The following are non limiting examples of how these methods may be applied. Antibody titers may provide information on the degree of protection against infectious diseases and the presence of underlying autoimmunity. An individual with no autoantibodies and high titers of antibodies protective against an infectious disease may receive no immunization, an similar individual with moderate titers providing protection against an infectious disease may only receive one dose of vaccine, while an individual with no antibodies to the organism or its toxin may receive several doses of vaccine. An individual with an abnormal glucose tolerance test and or autoantibodies against islet cells may not receive any vaccine irrespective of his or her risk for developing the infectious disease. An individual who develops high titers of autoantibodies after receiving a single dose of vaccine may be prohibited from receiving more vaccines.

The present invention also encompasses kits and products to perform the above mentioned screening methods. The kits and products may utilize any screening method suitable to perform the desired function. The following are several nonlimiting examples of products that could employ the screening methods. A product to determine if an mammal should receive an immunization where the product performs at least one of following: determining if said mammal has a protective immune response to a vaccine preventible organism and determining if said individual is at high risk for developing a chronic immune mediated disease that could be induced and or exacerbated by vaccination. A kit containing said product and a vaccine.

Methods and products described above may be beneficial for testing mammals in most age groups. The method is preferably employed prior to receiving each administration of vaccine when said mammal is older than 2 months of age especially if said mammal has not received a vaccine in the prior 3 weeks. The method may be used prior to receiving any vaccine immunogen as in the non limiting examples of an polio, BCG, smallpox, hepatitis B, diphtheria/tetanus/pertussis, an conjugated or unconjugated *Hemophilus influenza*, anthrax, plague, encephalitis, meningococcal, meningitis, pneumococcus, pneumonia, typhus, typhoid fever, streptococcal, staphylococcus, neisseria, lyme disease, cholera, *E. coli*, shigella, leishmania, leprosy, cytomegalovirus, respiratory syncytial virus, Epstein Barr virus, herpes, influenza, parainfluenza, rotavirus, adenovirus, HIV, hepatitis A, NonA NonB hepatitis, varicella, rabies, yellow fever, measles, mumps, rubella, HTLV, rabies, Japanese encephalitis, flavivirus, dengue toxoplasmosis, coccidiomycosis, schistosomiasis, malaria immunogen, and a molecule that cross reacts immunologically to at least one of said immunogen. The diseases to which protection should be measured will depend on what vaccines are approved for marketing. The disease may be one other than tuberculosis or rubella. As new vaccines enter the market then protective antibodies to their corresponding diseases may be measured. The vaccine may be a non living vaccine.

A screening method may be performed not only to determine if the antibody titers are protective but also to determine what brand of vaccine the recipient received if any by looking for antibodies to particular brand specific antigens as in the nonlimiting example of detecting antibodies to a carrier protein incorporated in a *Hemophilus influenza* vaccine. It is important that an individual who received an initial series of immunization with vaccines from one manufacture receives booster vaccines manufactured from that same manufacturer, preferably the same lot in order to prevent exposure to new antigens after 8 weeks. For example some *Hemophilus influenza* vaccines typically contain bacterial carbohydrate however some are not conjugated while others are conjugated. One brand may be conjugated with a tetanus toxoid another with a different protein. A vaccine registry would be ideal however people's name can not always be found on these registries. A test kit to determine the brand of vaccine the recipient received would help reduce the incidence of diabetes. A vaccine manufacturer may also include manufacturer specific immunological markers in their vaccines to help allow differentiation of brands of vaccines.

The present invention also encompasses methods, vaccines and vaccine kits that have a decreased propensity to induce a chronic immune mediated disorder when administered to an mammal of at least 2 months of age. These vaccines and vaccine kits may comprise vaccines and a immunosuppressant. The risk of inducing a chronic immune mediated disorder during booster administration may be lowered by boosting with an vaccine which lacks a strong adjuvant and using small molecular weight immunogens which retain the protective epitopes but induce less inflammation and are less immunogenic. An adjuvant like an aluminum salt may activate macrophages causing increased risk of type I diabetes mellitus and other chronic immune mediated diseases. Using a non living vaccine that lacks an aluminum based adjuvant may decrease this effect. Administration of an immunosuppressant preferably a glucocorticosteroid like cortisol or a longer acting version will help decrease inflammation including macrophage activation and decrease the risk as well. A hormone or other molecule capable of inducing the release of glucocorticoids as in the non limiting example of adrenocorticotropic hormone (ACTH) and corticotropin releasing hormone (CRH) would also perform the same function. A list of glucocorticoids and other immunosuppressants as well as their recommended administration ate described in the Physician's Desk Reference 1994. Administration doses will vary from recipient by recipient as known by one skilled in the art and administration may be optimized without unnecessary experimentation by using dosing instruction from readily available sources including the Physician's Desk Reference and information supplied herein especially the section on screening methods.

Having now generally described the invention, the same will be more readily understood through reference to the following examples which are provided by way of illustration, and not intended to be limiting of the present invention.

EXAMPLES

In Examples 1 and 2 mentioned below, initial vaccinations were either at day 8, 15 or day 1, 3, 10 respectively. This initial schedule was designed to minimize the phenomenon of under immunizing mice due to extravasation of vaccine from their abdomen and inadvertent injection into the visceral organs, bladder and gastrointestinal tract, which results in rapid clearance of the vaccine. Less frequent early administrations are needed for larger mammals when one is sure that extravasation or visceral injection does not occur. After the initial challenge injections every other week or even less frequent suffice.

The method of administration and the compositions contained in this invention allow relatively low amounts of immunogenic agent to be given. The anthrax vaccine, for example, as supplied by the manufacturer contains less than 200 micrograms of protein/ml as calculated using Lawry-based protein determination kit (Sigma, St. Louis, Mo.). Using the dilutions given in Example 1, the amount injected into mice comes to 0.2, 0.6, 0.8 µg protein on day 8, 15, 29. These amounts correspond to roughly 40–60 µg/kg body weight which are pharmaceutically acceptable doses.

The DT vaccine used contains about 180 micrograms of protein per ml and the DTP vaccine contains about 544 micrograms per ml.

The following examples involve immune modulation using commonly available human vaccines: anthrax vaccine, A, (Michigan Department of Health, Lansing, Mich.); combined diphtheria, tetanus vaccine, DT, (Connaught, Swiftwater, Pa.); combined whole cell diphtheria tetanus pertussis vaccine, DTP, (Connaught); and plague vaccine, P, (Miles, West Haven, Conn.). All vaccines are produced from killed microorganisms, and all except the plaque vaccine have an aluminum based adjuvant. The DT vaccine contains purified toxoids while the anthrax and pertussis vaccines are less pure. Vaccines are diluted using sterile technique in sterile phosphate buffer solution pH 7.4 using the notation 1:100 to indicate 1 part vaccine per 100 part PBS by volume. Vaccines were administered by intraperitoneal injections for convenience though other routes would be effective.

It is known that even though vaccines from different manufacturers provided similar protection to an infectious agent different vaccines contain different antigens, and different amounts of similar antigens (Merk Sharp Dome 1991). The following data shows that the exposure to new antigens at 2 months increases the risk of developing diabetes and chronic immune mediated disorders. The epidemiology data shown below demonstrates that different vaccines can interact to decrease the incidence of chronic immune mediated disorders or increase them.

Examples 1, 2 and 4 describe the anti-diabetic effect of the immunization programs herein disclosed on diabetes-in NOD mice (exs. 1 and 2) and diabetes in BB rats (ex. 4). It is now widely accepted by those skilled in the art that type I diabetes in humans responds similarly to immune intervention as does diabetes in NOD mice and BB rats. Diabetes in all three species is considered to be an autoimmune disease based on the presence of islet cell autoantibodies and strong genetic linkage between the development of diabetes and MHC genes (New England Journal of Medicine 314:1360–1368,1986; Diabetes Reviews 1:15–42,1993). Immunological events occurring in the first 2 months of life have been clearly shown to be responsible for the development of diabetes in NOD mice and BB rats. Recent human epidemiology data shows that immunological events occurring at birth have a profound effect on the development of diabetes. These events include maternal fetal blood group incompatibility as well as exposure to rubella virus and nitrates at birth (Diabetes Reviews 1:15–42,1993; Diabetologia 35:671–765,1992). The concept of diabetes in humans responding similarly to diabetes in NOD mice is widely accepted. Clinical trials have also shown that type I diabetes in humans can be prevented by immunosuppressants like cyclosporine when administered to prediabetics or newly diagnosed diabetics (Diabetes Reviews 1:15–42,1993). Immunosuppressants have a similar effect on NOD mice and BB rats (Clinical and Investiga-tive Medicine 10:488–495, 1987). The NIH recently embarked on a trial of screening up to 80,000 children to initiate a program of treating prediabetics with insulin immunotherapy, after a small phase I trial in humans supported results of in NOD mice (Lancet 341:927–928,1993).

The correlation between the effects of a diabetes treatment on NOD mice, and its prospective effect in diabetic humans, is confirmed by Rossini, Mordes, and Like, Ann Rev. Immunolog 3:289–320, 1985; Lampeter, Signore, Gale, and Pozzilli, Diabetologia 32:703–708, 1989; Pacheo-Silva, Bastos, Muggia, Pankewez, Nichols, Murphy, Strom, and Rubbin-Kelley, Eur. J. Immunology 22:697–702,1992; Rossini, Handler, Greiner, and Mordes, Autoimmunity 18:221–225, 1991; Kolb, Diabetes/Metabolism Reviews 3:751–758, 1987; Kikutani and Makino, Advances in Immunology 51: 285–321, 1992; Fox, J. Exp. Med. 175:1409–1412, 1992; Fitzpatrick, Lepault, Homo-Delarche, Bach, and Dardene, Endocrinology 129:1382–1390, 1991; Hawkins, Gala, and Dunbar P.S.E.B.M. 202:201–205, 1993; Jacob, Aiso, Michie, Mcdevitt, and Acha-Obea; Proc. National Acad. Sci. USA 87:968–972, 1990; McInerney, Pek and Thomas, Diabetes 40:715–725, 1991; Karounos and Thomas, Diabetes 39:1085–1090, 1990; Yale and Marliss, Cln. Exp. Immunol 57:1–11, 1984; Kastern, Lang and Sorensen, Current Topics in Microbiology and Immunology 156:87–102, 1990; Wang, Singh, Warnok, and Rajotte, Diabetes 41:114–117, 1992; Dotta and Eisenbarth, Clinical Immunology and Immunopathology 50:S85–S95, 1989; Elias, Reshef, Birk, van der Zee, Walker, Cohen, Proc. Natl. Acad. Sci. 88:3088–3091, 1991.

Many of the clinical characteristics of Type I diabetes in humans and of the similar diabetes in NOD mice are found in BB rats, leading experts to believe diabetes in BB rats is also a autoimmune disorder. Insulitis develops in the pancreas of BB rats before the onset of diabetes while antibodies develop to islet cells and possibly to insulin. Diabetes can be prevented by neonatal thymectomy as well as administration during the prediabetic period of cyclosporine, anti-lymphocyte antibodies, or purified lymphokines like TNF. Genetic experiments show that diabetes is closely linked to the MHC class II genes in BB rat as it is in humans. Many older rats develop autoimmune thyroiditis that is casually related to the development of diabetes as occurs in humans. Several review papers have been published on this model (Diabetes/Metabolism Reviews 3:725–750,1987; Critical Reviews in Immunology 9:45–65,1989; Diabetes/Metabolism Reviews 8:9–37,1992).

In view of the fact that the methods of the present invention have, as shown by comparing examples 1, 2 and 4, been efficacious in two different species of mammal, we believe that persons of ordinary skill in the art would expect the invention to be adaptable, without undue experimentation, to humans. In this regard, we believe that those skilled in the art would find it significant that these parallel successes were achieved despite differences between diabetes in NOD mice and in BB rats. Diabetes develops in approximately equal numbers of males and females in contrast to NOD mice where disease develops more commonly in females. The incidence of diabetes in BB rats is not affected by gonadectomy or the administration of androgens as occurs with NOD mice. In contrast to humans and NOD mice, BB/Wor rats, the most commonly used substrain of BB rats, are severely lymphopenic. They have a marked decreased number of mature T lymphocytes in peripheral blood, spleen and lymph nodes. The CD4+ subset is substantially reduced but the CD8+ subset is almost completely absent. Natural killer cells are relatively over expressed. Several review papers have been published on this model (Mordes et al. 1987; Parfrey et al. 1989; Crisa et al. 1992).

Examples 3 and 5 show that the value of the invention is not limited to the prevention or treatment of diabetes, but rather is relevant to other immune-mediated disorders, too, such as organ-specific autoimmunity (Ex. 3) and systemic lupus erythrematosis (SLE)(Ex. 5). Example 5 uses MRL/lpr mice as an SLE model.

The MRL/lpr mice, as with human SLE patients, develop anti-DNA and anti-nuclear autoantibodies which can cause immune complexes. The immune complexes can cause causing arthritis, dermatitis, and fatal immune complex glomerulonephritis if untreated (J. Invest Dermatol 0.94:52–57, 1990).

The following are a few references verifying both the similarity of the disease in MRL mice to SLE in humans and the clinical importance of the MRL model. Berger, Perez, Laroche, Edelson 1990, J. Investigative Dermatology 94:52–57; Halpern, Hersh, Yocum 1990, Clinical Immunology and Immunopathology 55:242–254; Guitierrez-ramos, Andreu, Marcos, Vegazo, and Martinez 1991, Autoimmunity 10:15–25; Shlomchick, Mascelli, Shan, Radic et al. 1990; J. Exp. Medicine 171:265–297; Breneman, Moynihan, Grota, Felten, Felten 1993; Brain, Behavior, & Immunity 7:135–43; Treadwell, Cohen, Williams, O'Brien, Volkman, Eisenberg 1993; Journal of Immunology 150:695–9; Lemire, Ince, Takashima 1992, Autoimmunity 12:143–8; Gallina, Steele 1991; Journal of Autoimmunity, 4:755–68; Loor, Jachez, Montecino-Rodriguez, Klein, Kuntz, et al. 1988; International Journal of Radiation Biology & Related Studies in Physics, Chemistry & Medicine, 53:119–36; Waterfield, Fairhurst, Chu, Levy, 1987; Immunology 61:173–8.

The MRL data is important not only because it is a good model for human SLE but because this autoimmune disease is both genetically, immunologically, and clinically very different from diabetes. Indeed, since the SLE-like disease spontaneously developed by the MRL mice has a wide range of clinical and serological characteristics that mimic not only human SLE but other autoimmune disorders such as Sjogren's syndrome, and rheumatoid arthritis (RA), see Bartlett, Popovic, Raiss 1988; Scandinavian Journal of Rheumatology—Supplement. 75:290–9, 1988, the MRL data can be deemed supportive of efficacy against these other autoimmune disorders, too.

Example 1

The first Example involved injecting anthrax vaccine diluted in PBS into female non-obese diabetic prone (NOD) mice (n=19) (Taconic, Germantown, N.Y.) on day 8 (0.1 ml, 1:100), day 15 (0.15 ml, 1:50), and day 29 (0.2 ml, 1:50) of life. A second group of NOD (n=20) received plaque vaccine diluted in PBS on the same days but at a slightly lower dilution, day 8 (0.1 ml, 1:50), day 15 (0.15 ml, 1:50), and day 29 (0.2 ml, 1:25). A third group of NOD (n=20) received a similar volume of PBS control on the same days as the mice in the first two groups.

Starting at approximately 16 weeks and continuing every 2 weeks until 28 weeks, tail blood was removed and checked for glucose using glucose sensitive chemstrips (Boehringer Mannheim, Indianapolis, Ind.) A blood glucose level over 300 mg/dl was considered positive. The cumulative incidence of diabetes in the anthrax treated group flattened out at 42.1% with no new cases detected after 24 weeks. The group receiving the plague vaccine appeared to begin flattening out and reached a cumulative incidence of 57.9% diabetic at 28 weeks. The PBS control group, showed a continual increase in the cumulative incidence of diabetes from 30% at 16 weeks to 65% at 28 weeks (FIG. 1). The remaining anthrax treated animals and PBS controls in experiment 1 were bled at 36 weeks. The net result was that no new cases of diabetes were detected in the anthrax treated group from 24 to 36 weeks and the cumulative incidence of diabetes flattened out at 42.1% compared to an incidence of 75% at 36 weeks in the PBS treated animals (FIG. 1). The flattening of cumulative incidence of diabetes curve indicates that diabetes is prevented not just delayed.

Example 2

A second set of experiments was designed to see if the therapeutic potential of anthrax vaccine could be improved by adding additional agents and changing the dosing schedule. Anthrax vaccine was given alone, with the combined diphtheria tetanus vaccine, or with the combined whole cell pertussis diphtheria tetanus vaccine. A series of nine intraperitoneal injections of the vaccines diluted in PBS were given to newborn NOD female mice using the following protocol: day 1 (0.1 ml, 1:100), day 3 (0.1 ml, 1:100), day 10 (0.15 ml, 1:100 ml), week 4 and every 2 weeks through week 14 (0.2 ml, 1:50). Vaccines were mixed prior to injection so volume in the notation refers to total volume injected.

Two control groups were used for Example 2. The first control involved injecting PBS using the dosing protocol mentioned above. The second control group in Example 2 received a single intraperitoneal injection of whole cell DTP vaccine diluted in PBS (0.2 ml, 1:50) at 2 months of age. This group was designed to see if the current immunization schedule of humans could inhibit the development of diabetes.

The new dosing schedule used in Example 2 greatly reduced development of diabetes in the NOD mice. The group receiving anthrax vaccine alone (n=29) had a cumulative incidence of diabetes that peaked at 24 weeks and remained constant at 13.8% through the 32nd week. These results compare to a cumulative incidence of 42.1% in the group receiving anthrax vaccine in Example 1. The most remarkable results in Example 2 occurred with animals treated with anthrax vaccine combined with the whole cell pertussis, diphtheria and tetanus vaccine. None of 29 animals developed diabetes by 32 weeks of age (FIG. 2).

The addition of the combined diphtheria and tetanus vaccine mixed with anthrax inhibited diabetes to a greater extent than anthrax alone but less than the combination of anthrax and DTP. Only 7.7% of animals receiving A+DT (n=26) developed diabetes by 32 weeks. A second group of mice (n=26) received a similar treatment of A+DT but were injected with DTP vaccine in place of DT at week 8. This was done to simulate the normal immunization of humans at 2 months with DTP. The animals in the later group developed a higher cumulative incidence of diabetes than those who did not receive pertussis component at 8 weeks, 23% versus 7.7% respectively at 32 weeks.

The injection of PBS slowed the progression of diabetes but the cumulative incidence curve did not flatten out during the 32 week study. The cumulative incidence in the PBS control was 48.1% at 32 weeks compared to 65% at 28 weeks in the PBS control of Example 1. The increased suppression of diabetes in the Example 2 group may be due to inflammation in the abdomen caused by the earlier and more frequent injections.

The control group receiving 1 injection of DTP at 8 weeks, developed a cumulative incidence of diabetes of 86.7% at 32 weeks. While the normal childhood vaccination schedule recommends a second injection at 16 weeks, 30% of animals already had diseases by this time and many of the rest probably had significant subclinical disease. A second injection would not have prevented disease in at least 30% of animals and thus the data clearly shows the current childhood immunization schedule for humans is ineffective in preventing immune mediated disorders.

Example 3

Another experiment involved injecting newborn mice with 15 mg/kg/day of cyclosporine (Sandoz, East Hanover, N.J.) intraperitoneally for the first 7 days of life to make the animals prone to developing autoimmunity (Sakaguchi and Sakaguchi 1989). Female C3H/Hen mice (Harlan Sprague Dawley, Indianapolis, Ind.) were then injected with a combination of the anthrax vaccine and the DT vaccine, or PBS control starting several days later to see if the vaccine would prevent the development of autoimmunity. The injection schedule was as follows: day 10 (0.15 ml, 1:100), day 17 (0.2 ml, 1:50) and every 2 weeks for 2 more injections (0.2 ml, 1:50).

A second injection schedule was performed using anthrax vaccine mixed with DTP vaccine to determine if the effect derived from the first set of experiments could be magnified by including pertussis vaccine at higher doses. Injections were as follows: day 6–8 (0.15 ml, 1:10), day 14–16 (0.2 ml, 1:10) and Day 27–29 (0.2 ml, 1:10), where the notation 6–8 means one administration during the period of 6 to 8 days.

Tail blood was drawn from mice at the age of about 8 weeks and the resulting sera, diluted 1:80 in a solution containing PBS and 3% fetal calf serum, was screened for autoantibodies using ELISA assays against gastric antigens (Sakaguchi and Sakaguchi 1989). The microsomal antigens were plated on Immulon 3 (Dynatech Laboratories, Chantilly, Va.). A second ELISA assay was prepared similarly by plating optimal amounts of $E.\ coli$ DNA (Sigma, St. Louis, Mo.) on Immulon 3 plates. An alkaline phosphatase-conjugated anti-IgG Fc fraction (Jackson Immuno-research, West Grove Pa.) was used as the secondary antibody and the substrate was a $2 \times 10^{-4}$ M 4-Methyumbelliferyl phosphate solution (Classen and Shevach, 1991). Plates were read on a Dynatech MicroFLOUR machine which uses a 365 nm Broadband Filter for the excitation beam and 450 nm narrow band interference filter for the emission beam.

Of those receiving the ADT treatment 22% (n=23) were free of antigastric antibodies compared to 12% (n=25) of female mice which received the PBS control. One control animal had DNA antibodies compared to none of the ADT treated mice. The effect was significantly greater in those mice receiving anthrax vaccine and DTP, as 6% (n=23 males and females) did not develop antigastric antibodies. Methods and compositions of the present invention are thus effective in preventing or substantially reducing the incidence of several chronic immune mediated disorders.

Example 4

Diabetic prone BB rats were immunized in order to show that the method of immunization could prevent diabetes in other species beside NOD mice. BB rats spontaneously develop diabetes at an early age as is the case in NOD mice and humans.

BB/Wor rats (U. of Massachusetts Medical School, Worchester Mass., USA) were immunized with a combination of the anthrax and DTP vaccines (n=20) or nothing as a control (n=28). Groups contained approximately equal number of male and female rats. The vaccinated group was given the following dosing schedule: day 1 (0.1 ml, 1:5); day 4 (0.15 ml, 1:5), day 11 (0.15 ml, 1:5), day 25 (0.2 ml, 1:5), day 39 (0.2 ml, 1:5), day 53 (0.2 ml, 1:5), day 61 (0.2 ml 1:2.5), and every 14 days for 3 more injections at approximately (0.2 ml, 1:2.5). Days of injection varied by one at times. (The notation 1:5 means 1 part vaccine to 5 parts PBS.)

Figure 3:
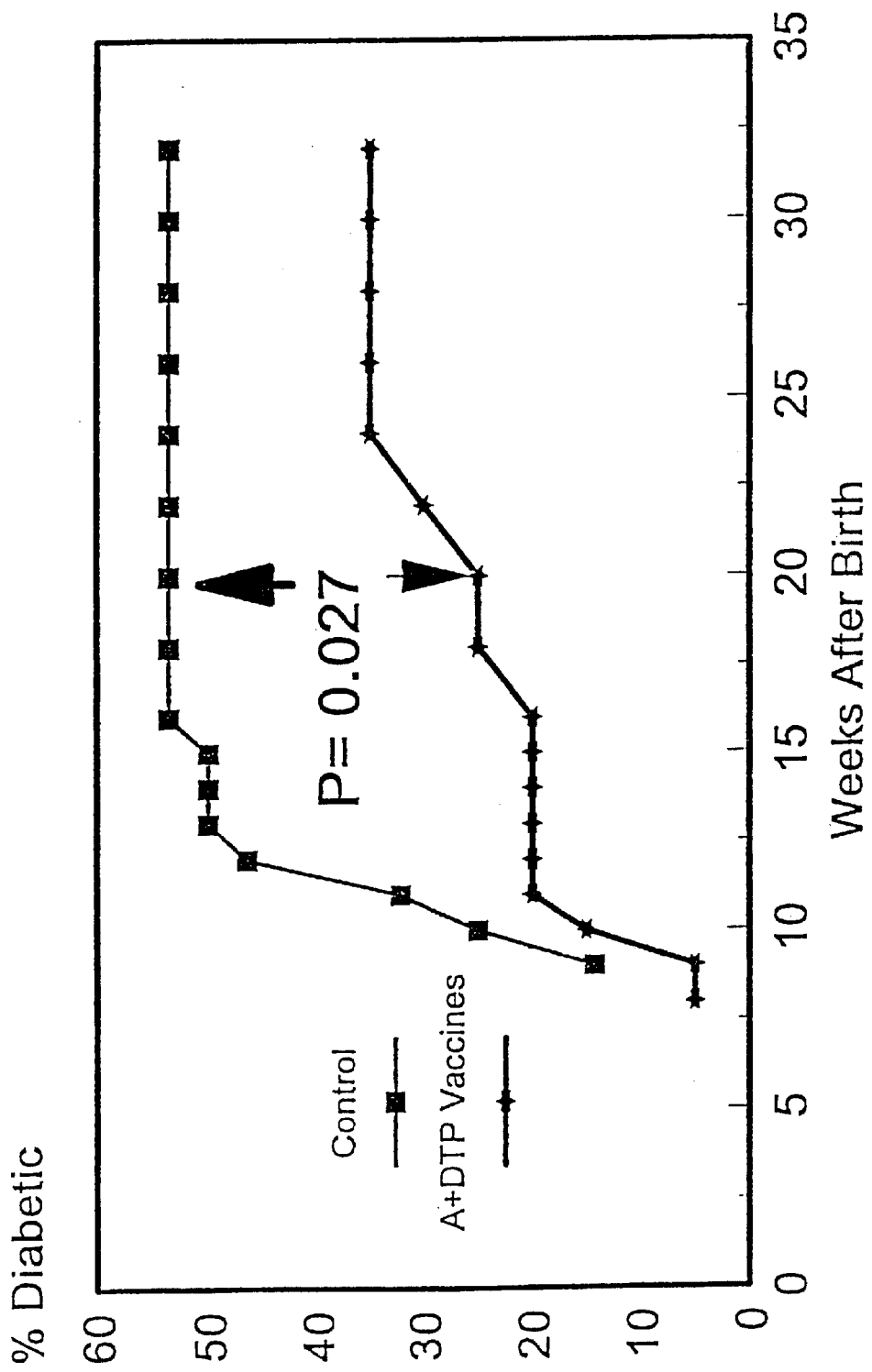

At 16 weeks of age 54% of the untreated rats had developed diabetes and or died compared to 20% in the vaccinated group. At 20 weeks of age 54% of the untreated rats had developed diabetes and or died compared to 25% in the vaccinated group. At 32 weeks the results were 54% versus 35% respectively (FIG. 3) which represents a 34% reduction in the incidence of diabetes. The difference between the two groups were statistically significant at 20 weeks (P=0.027).

The findings that the method of immunization can prevent diabetes in both NOD mice and BB rats provides strong proof that methods of immunization presented in the specifications have the ability to prevent chronic immune mediated diseases in mammals with very different genetic defects.

Example 5

The methods of immunization taught herein also inhibit spontaneous autoimmunity in MRL/lpr mice, which develop a disease that closely resembles Systemic Lupus Erythematosus or SLE in humans.

Pregnant MRL/MpJ-lpr mice (Jackson Laboratory, Bar Harbor, Me.) gave birth to pups which were injected with PBS or a combination of the anthrax vaccine and the acellular DTP vaccine. A series of nine intraperitoneal injections of the vaccines, diluted in PBS, were given to newborn mice using the following protocol: day 1 (0.1 ml, 1:100), day 3 (0.1 ml, 1:100), day 10 (0.15 ml, 1:100 ml), week 4 and every 2 weeks through week 14 (0.2 ml, 1:50). Weaning was done at approximately 21 days and only the female mice were used in the experiment. One group of 18 control mice received a similar injection schedule of PBS starting on day 1 and a second group of 20 control mice received a similar schedule (i.e., every 2 weeks through week 14) but starting at 4 weeks of age.

Urine was screened for the presence of protein, a common clinical test for glomerulonephritis. A few drops of mouse urine were placed on a urine protein dipstick (Albustix, Miles Inc, Elkhart, Ind.). At 13 weeks 6/38 (15.8%) of PBS control mice had a urine with a protein over 300 mg/dl while 0/28 of the vaccinated mice had a urine with a protein over 300 mg/dl. At 14 weeks 8/38 (21%) of PBS control mice had a urine with protein of over 300 mg/dl while 0/27 of the vaccinated mice had developed urines with similar protein levels. At 15 weeks 10/38 (26.3%) of PBS control mice had a urine with protein of over 300 mg/dl while 2/26 (7.7%) of the vaccinated mice had developed urines with similar protein levels.

Example 101

Epidemiology studies were performed to verify that immunization practices with pharmaceutically acceptable doses of pharmaceutically acceptable vaccines modulates the development of diabetes. The data includes correlations between the specific immunization schedules and the incidence of diabetes in western European countries as well as temporal studies showing changes in the incidence of diabetes in countries after the immunization schedules were changed. Additional epidemiology data is provided to explain the mechanism of action of this phenomenon and give further support for the data showing vaccination can prevent the development of immune mediated diabetes in humans.

1. Intercountry Analysis.

Europe was chosen for an intercountry analysis because in a relatively small geographic area there are many different countries that have different immunization schedules and the incidence of diabetes in the countries is known. The people in the western European countries have closely related racial backgrounds, diets, economic standards of living, and standards of health care. Eastern European countries of the former communist block were excluded because their standard of living and standard of medical care is not up to western levels.

The study made the following assumptions: (1) the nations included in the study had developed comparable quality of health care allowing for similar risk of neonatal infections and similar efficiency in diagnosing diabetes; (2) vaccines were of comparable quality from country to country; (3) the amount of diphtheria and tetanus toxoid given to people in different countries did not induce a significant biological difference; and (4) epidemics traveled freely across borders such that a person in a given European state was as likely to be exposed to a given pathogen as some one in another country.

The data correlating the incidence of diabetes to immunization schedule in western European countries is presented in Table I. References pertaining to the immunization schedules and incidence of diabetes of each country are included with table I. Data on the incidence of diabetes was taken from the following multiple sources. (Green et al 1992; Nystrom, Dahlquist, Rewers, Wall 1990; Helgason, Danielsen, and Thorsson 1992; Metcalfe and Baum 1991; Levy-Marshal et al. 1990; Tuomilehto et al 1991.) Immunization practices in each country were taken from an assortment of publications. Note that the incidence of diabetes in Malta was significantly understated according to the Schranz and Prikatsky, (Diabetic Medicine 6:228–231, 1989). The authors calculated the incidence of diabetes in Malta using the number of type I diabetics in public health clinics and the number of children of a particular age in the country. The authors admit significant number of diabetic children were treated in private clinics that were not accounted for.

Sweden was one country that-was difficult to characterize. The country stopped immunizing newborns with BCG in the middle of 1975 but the date it stopped revaccinating school children may have been as late as 1986. Pertussis vaccination of newborns was stopped in 1979.

The data in Table I indicates that administration of vaccines after two months increases the incidence of diabetes while administration of vaccines at birth can prevent diabetes. The findings are highly statistically significant. Administration of the pertussis vaccine after two months of age explains the higher incidence of diabetes in group 3 compared to most regions in group 1. Administration of the BCG vaccine after two months of age explains the higher incidence of diabetes in group 4 compared to group 3. Administration of the *Hemophilus influenza* vaccine after two months of age explains the higher incidence of diabetes in group 5 compared to 4. The ability of the BCG vaccine to protect against diabetes when administered at birth explains the lower incidence of diabetes in group 2 compared to group 3. There appears to be a correlation between immunization rate and the incidence of diabetes within some groups since the districts in England and Ireland which had low immunization coverage with the pertussis vaccines compared to other countries in their groups (World Health Statistics Annual, 1991 page 62) had the lowest incidence of diabetes in their groups. Luxembourg had the highest incidence of diabetes in group 3 which can be explained by a significant number of individuals receiving the BCG vaccine even though it is not required (ibid). Minor variations within a group can be explained by genetic variation, environmental differences including epidemics, use of additional vaccines and the percent of children fully immunized.

Epidemiology data in the United Kingdom supports the animal data that vaccination with DTP induces diabetes. During the pertussis scare of the 70's and early 80's England had a significantly lower immunization rate for pertussis than Scotland. This can explain the lower incidence of diabetes in England than Scotland in 1988. Furthermore, in Scotland those from deprived neighborhoods received fewer vaccinations which could explain the lower incidence of diabetes in areas of deprivation. (Metcalfe and Baum 1991; Patterson and Waugh 1992; Wrench, McWhirter, and Pearson 1991; Maclure and Stewart 1984).

The incidence of diabetes in Sardinia is the one major exception in the study showing that the incidence of diabetes correlates with diabetes. Sardinia has an very high incidence of diabetes that can not be explained by the routine pediatric immunization practices used on the island. The high incidence of diabetes however can be explained by the extremely high incidence of thalassemia on the island. It is estimated that as many as 1:250 live births in Sardinia during this time had beta thalassemia major (NY ACAD Science 612:215–225, 1990). Prevalence studies show that 16% of these patients older than 10 are diabetic (Archives of Diseases in Children 63:58–62, 1988). Prevalence studies tend to underestimate the frequency of diabetes, because some patients die, so the cumulative incidence of diabetes in patients homozygous for the thalassemia major gene in the 0–14 age group may be as high as 25 per 100 or 25%. The elevated incidence of diabetes in homozygotes can partially explain the increased incidence of diabetes in Sardinia. An elevated incidence of diabetes in heterozygotes for beta thalassemia or alpha thalassemia could explain the rest of the elevated incidence of diabetes. According to Cao et al. (Journal of Medical Genetics 15:443–447, 1978) about 12.5% of individuals living in Sardinia are heterozygous for beta thalassemia and many of these have disorders similar to those in the homozygotes though less severe.

2. Intracountry Temporal Analysis: Induction of Diabetes

Animal and human epidemiology data indicates that the incidence of diabetes will change when a country changes its immunization schedule. The data below suggests that if a vaccine is initially given after two months of age then the incidence of diabetes will go up. This situation was seen in both epidemiology studies of diabetes Finland and the United States.

A. Finland

In Finland the incidence of diabetes had been very stable in the 0–4 year old age group from 1966–1975 until after the government made several changes to its vaccination schedule which was followed by large increases in the incidence of diabetes in the years 1976–1978 and 1988–1990 (Diabetologia 36:1303–1308, 1993). The rises in the incidence of diabetes can be explained by the addition of three new vaccines to the Finnish vaccine schedule. A large clinical trial immunizing 130,000 infants aged three months to 5 years old with *Hemophilus influenza* or menin-gococci polysaccharide vaccines was started in November, 1974 (New England Journal Medicine 297: 686–691, 1977). Finland has a small population with less than 65,000 children born each year (World Health Statistics Annul) so 130,000 represented a significant proportion of children in-the-country 0–4 years of age. In 197.6 the pertussis vaccine in Finland was changed by the addition of a second strain of bacteria making the vaccine more antigenic (Acta Paediatric Scand 298 Suppl 21–25, 1982). The vaccine regiment was next altered to include the measles, mumps, rubella, (MMR) vaccine in 1982. A trial of *Hemophilus influenza* conjugate vaccine was initiated in January 1986 and included 114,000 children born between Oct. 1, 1985 and Aug. 31, 1987. Based on the results of the trial the *Hemophilus influenza* vaccine became part of the standard vaccine schedule in Finland starting in January of 1988 (New England Journal Medicine 317:1381–1387, 1990).

The changes in the incidence of diabetes especially in the 0–4 year old age group in Finland correspond temporally very closely with the changes in the vaccine schedule, supporting the rodent and the intercountry epidemiology data that the development of immune mediated diabetes is influenced by vaccination (Table II). The use of the *Hemophilus influenza* vaccine as well as the addition of a second strain of bacteria to the pertussis vaccine explains the rapid rise of diabetes seen in the years 1977–1979 in 0–4 year olds. The discontinuation of the *Hemophilus influenza* vaccine can explain the drop in the incidence of diabetes in 0–4 year olds from 19.3 in the 1977–1979 cohort to 16.0 in the 1980–1982 cohort (Diabetes Care 8, Suppl 1:10–16, 1985). The widespread use of the MMR vaccine starting in 1982 and the *Hemophilus influenza* vaccine in 1986 can explain the large rise in the incidence of diabetes in the 0–4 age group between the years 1980–1982 and 1987–1989 (Diabetologia 36:1303–1308, 1993), Temporal data comparing the incidence of diabetes in different age groups suggest that the use of more antigenic vaccines schedules is causing the increased incidence of diabetes in Finland since the increased incidence is only seen in those who received the new vaccines. The temporal rises in the incidence of diabetes in the 0–4 year old age group occur shortly after the new vaccines are added but rises in the incidence of diabetes in the older age groups are delayed until those children immunized with the new vaccine reach the older age group. For example, following the use of the *Hemophilus influenza*/mening-ococcus vaccine in 1974 and new pertussis vaccine in 1976 the incidence of diabetes in the 1977–1979 cohorts increased compared to 1970–1976 cohorts by 63.5% in 0–4 year olds, 16% in 5–9 year olds, 0% in 10–14 year olds (Table II). Changes in incidence of diabetes were statistically more significant in the 0–4 age group, the age group that received the vaccine. When the incidence of diabetes started to decline in 0–4 year olds in 1980–1982 following discontinuation of the *Hemophilus influenza*/meningococci vaccine, the incidence continued to rise in 5–9 and 10–14 year olds as those who received the *Hemophilus influenza*/meningococci vaccine and the new pertussis vaccine entered these age groups.

B. Allegheny County, Pennsylvania (Greater Pittsburgh Area)

Changes in the incidence of diabetes in Allegheny County, Pennsylvania (Diabetes Care 16:1606–1611 1993) can also be explained by changes in immunization schedules, supporting findings discussed earlier that the incidence of immune mediated diabetes in humans is affected by vaccination. The epidemic of diabetes occurring in the 0–4 age group during the years 1985–1989, (Table III) can be explained by the addition of the *Hemophilus influenza* vaccine to the immunization schedule. The FDA approved the *Hemophilus influenza* polysaccharide vaccine in 1985 and the conjugated vaccine in 1987 (Jama 269:221–226, 1993). The vaccine was widely administered to children in Allegheny County. A study of its efficacy performed in Allegheny county showed that about 36% of children, chosen as controls, were immunized with the vaccine between August, 1985 and July, 1987 (Jama 260:1419–1422, 1988). Based on epidemiology and animal data discussed earlier it was predicted that the incidence of diabetes would rise in Allegheny County after wide spread use of the *Hemophilus influenza* vaccine occurred.

The drop in the incidence of diabetes in the 0–4 age group in years 1975–1979 can be explained by a drop in pertussis immunization. In September, 1974, at a time when there was international concern about the incidence of encephalitis caused by the pertussis vaccine, the Pennsylvania state government passed Act 210 of 1974 requiring children to receive certain immunizations prior to entering school (Pennsylvania Medicine December 1974, p41–42). The law required immunization with polio, diphtheria, tetanus, measles and rubella, but not with pertussis vaccine. The law was a clear message that immunization with the pertussis vaccine was not considered necessary. Following the passage of this law, incidence of diabetes in the 0–4 age group dropped about 61% in the 1975–1979 time period as compared to 1965–1969 (P<0.001) as shown in Table III. During the period of 1975 to 1979, immunization with the pertussis vaccine dropped of in several countries. Immunization with the pertussis vaccine was stopped in Sweden and pertussis vaccine acceptance in the United Kingdom fell from 75% in 1974 to 30% in 1978. (Pediatric Infectious Disease Journal 6:364–371, 1987).

The incidence of diabetes in the 0–4 age group during the period 1980–1984 rose to levels even higher than before 1975. This can be explained by the Pennsylvania Department of Health calling for increased immunization with the pertussis vaccine following an epidemic of pertussis in Pennsylvania in 1982 (Pennsylvania Medicine, March, 1983, p. 16) and new state laws requiring that children receive the mumps vaccine (Pennsylvania Medicine, January, 1983, pp. 12–16). The results are consistent with previous findings that changes in immunization policy can lead to changes in the incidence of immune mediated diabetes.

3. Intracountry Temporal Analysis; Prevention of Diabetes

Epidemiology data from the Netherlands provides evidence that immunization with the smallpox vaccine at birth can prevent the development of diabetes. This data supports the intercountry epidemiology data that immunization at birth with the BCG vaccine can prevent diabetes. The findings also support the temporal data presented above that changes in immunization practices can effect the development of immune mediated diabetes in humans.

Epidemiology data shows that in the cumulative incidence of diabetes up to the age of 18 differed significantly in Danish birth cohorts (Diabetologia 35:139–142, 1992). There were two significant drops in the incidence of diabetes; one was centered around 1962 when the cumulative incidence dropped to 1.1 per 1000 ($P<0.05$), and the other was centered around 1966 when the cumulative incidence dropped to 1.71 per 1000. The drops are in contrast to a cumulative incidence of diabetes outside of these troughs of about 1.98 per 1000 (Table IV). The drops in 1962 and 1966 both occurred during smallpox epidemics in Europe and can best be explained by immunization of newborn infants in these periods with smallpox vaccines.

Western Europe had major epidemics of smallpox centered around the years 1962 and 1966. The epidemic in 1962 actually started in 1961 continuing into 1963 and included 158 cases from seven western European countries. The 1966 epidemic included 72 cases and was limited to the United Kingdom. There was a strong emphasis placed on vaccination in smallpox epidemic of 1961–1963 as demonstrated by World Health Organization statistics showing 23.5 million Europeans were vaccinated with the smallpox vaccine in 1962 compared to an norm of about 11 million in nonepidemic years (International Symposium on Vaccination against communicable diseases Monaco 1973;. Symp. Series Immunobiol. Standard 22:13–24.) Changes in smallpox vaccine acceptance were detected around 1962 and 1966 in the Netherlands (ibid pp. 271–276).

Literature from the 1960s and earlier suggested humans could be immunized at any time after birth, but immunization before three months of age was associated with an increased risk of encephalitis. It was customary at the time for physicians practicing in areas with a low incidence of smallpox to wait until the patient was several months old before administering the smallpox vaccine, however in areas with high incidence of smallpox, like third-world countries, smallpox vaccine was often given at birth (International Symposium on Smallpox Vaccine, Bilthoven 1972. Symp. Series immunobiol. Standard 19:243–248; Tubercle 43:155–160, 1962).

The common practice in the Netherlands in the 1960s was to immunize children with the smallpox vaccine starting at two months of age in normal, nonepidemic conditions (International Symposium on Smallpox Vaccine, Bilthoven 1972. Symp. Series Immunobiol. Standard 19:235–242). Given the fact that the literature recommends immunization earlier than usual in times of epidemics, it would have been expected that a number of physicians would have given the vaccine several weeks earlier as in four weeks of age or at birth. The resulting switch in immunization explains the drop in the incidence of diabetes in the cohorts born during smallpox epidemics.

4. Related Epidemiology Data

Epidemiology data suggests that diabetes in humans can be caused by transient immunological changes at birth which gives further support to the finding that immunization can alter the development of diabetes in humans. A report has been published that maternal-child blood group incompatibility is associated with an increased risk for developing diabetes (OR=1.61) (Diabetologia 1992; 35:671–675). The more severe cases of the disorder had a higher incidence of the disease. Maternal-child blood group incompatibility has been shown by others (New England Journal of Medicine Aug, 22, 1974, p420) to cause transient suppression of the thymus/T cell immune system. These findings demonstrate that in humans, as in rodents, transient alterations to the developing immune system, immunosuppression or stimulation, will alter the risk of developing immune mediated diabetes or another chronic immune mediated disease later in life, enhance or decrease respectively.

All references cited herein, including journal articles or: abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Any description of a class or range as being useful or preferred in the practice of the invention shall be deemed a description of any subclass or subrange contained therein, as well as a separate description of each individual member or value in said class or range.

TABLE I

Intercountry Analysis
Immunization Schedule Versus Incidence of Type I Diabetes

| Group | Immunization Schedule | Year | Incidence of Diabetes (Mean) | P Values |
|---|---|---|---|---|
| 1 | No Pertussis, No BCG | | (14.5) | |
| | Italy, Lombardi (6, 13, 1) | 1988 | 6.8 | |
| | Italy, Lazio (6, 13, 1) | 1987 | 6.5 | |
| | Italy, Sardinia (6, 13, 1) | 1987 | 30.2 | |
| 2 | Pertussis, BCG before 2 months | | (7.45) | X |
| | R. of Ireland (6, 2) | 1988 | 6.8 | |
| | France (6, 1) | 1990 | 7.8 | |
| | Austria (6, 1) | 1989 | 7.7 | |
| | Portugal (6, 1) | 1986 | 7.5 | |
| 3 | Pertussis, No BCG | | (10.92) | <0.02 X |
| | Iceland (7, 3) | 1980–1989 | 10.8 | |
| | Netherlands (6, 1) | 1989 | 11 | |
| | Spain, Catelinia (6, 1) | 1986 | 10.6 | |
| | Spain, Madrid (6, 16) | 1985–1988 | 10.9 | |
| | Belgium (9, 1) | 1989 | 9.8 | |
| | Luxembourg (6, 1) | 1989 | 12.4 | |
| 4 | Pertussis, BCG Vaccination School Age | | (20.01) | <.0001 <.005 X |
| | England, Oxford (6, 1) | 1988 | 16.4 | |
| | Northern Ireland (6, 2) | 1988 | 16.6 | |
| | Scotland (6, 2) | 1988 | 19.8 | |
| | Denmark (6, 12, 1) | 1990 | 21.5 | |
| | Norway (15, 1) | 1989 | 20.8 | |
| | Malta (9, 4) | 1980–1987 | (13.6+) | |
| | Sweden (6, 10, 11, 5) | 1987 | 25 | |
| 5 | Pertussis, Hib, BCG Vaccination at 3 months and School | | (42.9) | <.0001. <.0001 <.0001 |
| | Finland (6, 14, 1) | 1988 | 42.9 | |

Incidences of type I diabetes mellitus are reported as yearly figures per 100,000 children as recorded in the references indicated. Statistics were generated from unweighted group means using a normal approximation to the poisson distribution. All statistics shown where highly significant using T=1 with the exception of group 3 where (P<0.02) was calculated using T=4. Sardinia was the only major exception to the trend as discussed in the text. The incidence of diabetes in Malta was significantly underestimated as discussed in reference 4. The immunization schedule of Sweden has changed during the 15 years prior to 1987. Most notably the pertussis vaccination was discontinued in 1979.

REFERENCES (1) Lancet 339:905–909, 1992 (2) British Medical Journal 302:443–447, 1991 (3) Diabetologia 35:880–883, 1992 (4) Diabetic Medicine 6:228–231, 1989 (5) International Journal of Epidemiology 19:141–146, 1990 (6) World Health organization, Working Group on Immunization of Tourists and other Travelers Venice, November 1990, By B. Bytchenko (7) Vaccination policy and status in Iceland, Iceland Government (8) Symp. Series Immunobiol. Standard, 22:223–225, 1973 (9) Personal Communication Malta pediatrician, #011–356–241–251 (10) Pediatr. Infect. Dis J. 6:364–371, 1987 (11) Personal Communication Dr. Ingrid Trolin, Uppsala Sweden #46 18 17 46 61 (12) Symp. Series Immunobiol. Standard, 22:235–237, 1973 (13) Pediatr. Infect. Dis. J. 11:653–661,1992 (14) N. Engl. J. Med 323:1381–13871 1990 (15) Tubercle 69:119–123, 1988 (16) Diabetologia 33:422–424, 1990.

TABLE II

Incidence of Type I Diabetes in Finland

| Age Group | Years | N | Incidence of Diabetes | % Change Incidence | P values | |
|---|---|---|---|---|---|---|
| 0–4 | 1970–76 | 262 | 11.8 | | X | |
| | 1977–79 | 174 | 19.3 | 63.6% | $P < 0.001$ | |
| | 1980–82 | 152 | 16 | −17.1% | $P < 0.005$ | X |
| | 1987–89 | 243 | 25.9 | 61.9% | $P < 0.0001$ | $P < 0.0001$ |
| 5–9 | 1970–76 | 729 | 27.6 | | X | |
| | 1977–79 | 304 | 32 | 15.9% | $P < 0.05$ | |
| | 1980–82 | 299 | 33 | 3.1% | $P < 0.02$ | X |

TABLE II-continued

Incidence of Type I Diabetes in Finland

| Age Group | Years | N | Incidence of Diabetes | % Change Incidence | P values | |
|---|---|---|---|---|---|---|
| 10-14 | 1987-89 | 382 | 39.3 | 19.0% | P < 0.0001 | P < 0.05 |
| | 1970-76 | 1047 | 37.5 | | X | |
| | 1977-79 | 421 | 37.5 | 0% | N.S. | |
| | 1980-82 | 399 | 38.6 | 2.93% | N.S. | X |
| | 1987-89 | 389 | 40.6 | 5.2% | N.S. | N.S. |

Incidences of type I diabetes mellitus are reported as yearly figures per 100,000 children as recorded in the references indicated. The percent change in incidence was calculated using the incidence in the prior year as the reference. Statistics were recorded as reported in the references when available. Statistics not reported were calculated using a normal approximation to the poisson distribution. Differences that were not statistically significant are marked N.S.

REFERENCES

Diabetologia 35:70–76, 1992
Diabetes Care 8 Suppl 1:10–16, 1985
Diabetologia 36:1303–1308, 1993

TABLE III

Incidence of Type I Diabetes Mellitus
Age 0–4, Allegheny County, Pennsylvania

| Years | Incidence of Diabetes | % Change Incidence | P Values |
|---|---|---|---|
| 1965-1969 | 6.75 | X | |
| 1970-1974 | 6.375 | -5.55% | N.S. |
| 1975-1979 | 2.625 | -58.22% | P < .001 |
| 1980-1984 | 9.875 | 276.19% | P < .02 |
| 1985-1989 | 16.125 | 63.29% | P < .0001 |

Total # of Cases 183

Incidences of type I diabetes mellitus are reported as yearly figures per 100,000 children as recorded in the reference indicated. The percent change in the incidence was calculated using the incidence in the prior year as the reference. Statistics were calculated using a normal approximation to the poisson distribution. The results show a highly statistically significant decline in the incidence of type I diabetes mellitus in the years 1975–1979 as well as statistically significant rise during the years 1980–1989. Differences that were not statistically significant were marked N.S.

REFERENCE

Diabetes Care 16:1606–1611, 1993

TABLE IV

Cumulative Incidence of Type I Diabetes Mellitus
Danish Military Recruits Age 18

| Year Born | # of Diabetics | Cumulative Incidence Diabetes/1000 | P value | Smallpox Cases Western Europe |
|---|---|---|---|---|
| 1960 | 189 | 1.85 | | 1 |
| 1961 | 167 | 1.76 | | 79 |
| 1962 | 96 | 1.11 | P < 0.05 | 51 |
| 1963 | 188 | 1.5 | | 28 |
| 1964 | 198 | 1.83 | | 0 |
| 1965 | 203 | 1.93 | | 1 |
| 1966 | 184 | 1.71 | N.S. | 72 |
| 1967 | 219 | 2.07 | | 2 |
| 1968 | 194 | 1.96 | | 2 |
| 1969 | 264 | 2.11 | | 0 |
| 1970 | 234 | 2.12 | | 22 |

Cumulative incidences of type I diabetes mellitus in Danish military recruits under 19 years of age are reported per 1000 recruits as recorded in the reference indicated. Statistics were calculated by the authors in the reference. The results show a statistically significant decline in the incidence of type I diabetes mellitus in the years 1961–1963, which corresponded to a smallpox epidemic. The decline in the incidence of diabetes in 1962 followed the epidemic of 1961. The incidence of diabetes also declined in 1966 during a second smallpox epidemic. The later was not statistically significant, N.S.

REFERENCE

Diabetologia 35:139–142, 1992
WHO Chronicle 16:302–3051 1962
Vasile Tudor and loan Strati, 1977, Smallpox Cholera. Abacus Press, Kent England.

TABLE V

Potential Iwmunization Schedules

| Week | Schedule 1 | Schedule 2 |
|---|---|---|
| 0 | DTP, Hib, HepB, IPV, MMR, NPI | |
| 1 | | |
| 2 | DTP, Hib, HepB, IPV, MMR, NPI | DTP, Hib, HepB, OPV, MMR |
| 3 | | |
| 4 | DTP, Hib, HepB, IPV, MMR, NPI | DTP, Hib, HepB, OPV, MMR |
| 5 | | |
| 6 | DTP, Hib, HepB, IPV, MMR, NPI | DTP, Hib, HepB, OPV, MMR |
| 7 | | |
| 8 | DTP, Hib, HepB, IPV, MMR, NPI | DTP, Hib, HepB, OPV, MMR |
| 9 | | |
| 10 | DTP, Hib, HepB, IPV, MMR, NPI | DTP, Hib, HepB, OPV, MMR |
| 11 | | |
| 12 | DTP, Hib, HepB, IPV, MMR, NPI | DTP, Hib, HepB, OPV, MMR |
| 13 | | |
| 14 | DTP, Hib, HepB, IPV, MMR, NPI | DTP, Hib, HepB, OPV, MMR |

TABLE V-continued

Potential Iwmunization Schedules

| | | |
|---|---|---|
| 15 | | |
| 16 | DTP, Hib, HepB, IPV, MMR, NPI | DTP, Hib, HepB, OPV, MMR |
| 17 | | |
| 18 | DTP, Hib, HepB, IPV, MMR, NPI | DTP, Eib, HepB, OPV, MMR |

| Week | Schedule 3 | Schedule 4 |
|---|---|---|
| 0 | DTP, Hib, HepB, IPV, MMR, NPI | DT, Hib, HepB, IPV |
| 1 | | |
| 2 | | DTP, Hib, HepB, IPV, MMR |
| 3 | DTP, Hib, HepB, IPV, MMR, NPI | |
| 4 | | DTP, Hib, HepB, IPV, MMR |
| 5 | | |
| 6 | DTP, Hib, HepB, IPV, MMR, NPI | DTP, Hib, HepB, IPV, MMR |
| 7 | | |
| 8 | | |
| 9 | DTP, Hib, HepB, IPV, MMR, NPI | DTP, Hib, HepB, IPV, MMR |
| 10 | | |
| 11 | | |
| 12 | DTP, Hib, HepB, IPV, MMR | DTP, Hib, HepB, IPV, MMR |
| 13 | | |
| 14 | | |
| 15 | DTP, Hib, IPV, MMR | DTP, Hib, HepB, IPV, MMR |
| 16 | | |
| 17 | | |
| 18 | DTP, Hib, IPV, MMR | DTP, Hib, HepB, IPV, MMR |

The four immunization schedules above are nonlimiting examples of immunization schedules that can be used to reduce the incidence of diabetes as compared to standard immunization schedules listed in the specifications. The following abbreviations are used above: DTP—diptheria, tetanus, pertussis; Hib—*Hemophilus influenza* B; HepB hepatis B; IPV—inactivated polio virus; OPV—oral polio virus, MMR-measles mumps rubella, NPI—nonpediatric immunogen.

REFERENCES

Agnese, di Sant, P. A. (1950) *Amer. J. Publ. Hlth.* 40:674–680.
Blom L., et al (1991) *Diabetologia* 34:176–181.
Classen and Shevach (1991) *Transplantation* 51:1052–1057.
Elias et al (1990) *Proc. Natl. Acad. Sci. USA* 87:1576–1580.
Fagan et al (1991) *Diabetes* 40:715–725.
Grange et al (1990) *Tubercle* 71:61–64.
Green A., et al (1992) *Lancet* 339:9.05–909.
Guberski et al (1991) *Science* 254:1010–1013.
Halsey et al (1985) *Bulletin World Health Org.* 63:1151–1169.
Halsey et al (1985) *New Engl. J. Med.* 313:544–549.
Harada et al (1990) *Diabetes Res. and Clin. Prac.* 8:85–90.
Helgason T., et al (1992) *Diabetolgia* 35:880–883.
Hems et al (1971) *Lancet* 1:183.
Huang et al (1984) *Pediatric Res.* 18(2):221–226.
Huang et al (1991) *Autoimmunity* 9:311–317.
Kojima A. and Prehn R T (1981) *Immunogenetics* 14:15–27.
Kolb,
H. et al., (1987) *Diabetes Res.* 6:21–27.
Levy-Marshal C., et al. (1990) *Diabetologia* 33:465–469.
Maclure A. and Stewart G T (1984) *Lancet September 22*, 682–685.
Merk Sharp Dome (1991) Package insert Recombivax HB. September 1991
Metcalfe M A and Baum J D (1991) *British Medical Journal* 302:443–7.
MMWR 1992. 41,RR-1:1–10
Niskanen L. et al (1991) *Diabetologia* 34:402–408.
Nystrom L. et al (1990) *International J. of Epidemiology* 19:141–146.
Oldstone (1988) *Science* 239:500–502.
Oldstone et al (1990) *J. Exp. Med.* 171:2077–2089.
Patterson C C and Waugh N R (1992) *International J. Epidemiology* 21:108–117.
Pearce et al (1991) *J. Pharmacol. Exp. Therap.* 258:710–715.
Reich et al (1989) *Diabetes* 38:1647–1651.
Sadelain et al (1990) *Diabetes* 39:583–589.
Sakaguchi et al (1989). *J. Immunol.* 142:471–480.
Salonen et al (1975) *Int. J. Cancer* 15:941–946.
Satoh et al (1989) *J. Clin. Invest.* 84:1345–1348.
Sauer, L. W. and Tucker, W. H., (1950) *Amer. J. Publ. Hlth.* 40:681–685.
Serreze et al (1989) *J. Autoimmun.* 2:759–776.
Shintani et al (1990) *J. Immunol.* 144:136–141.
Toyota et al (1978) *Diabetologia* 14:319–323.
Tuomilehto J. et al (1991) *Diabetes Care* 14:982–988.
Wrench J. et al (1991) *British Medical Journal* 302:787–788.

What is claimed is:

1. A method of immunizing a mammalian subject which comprises:
   (I) screening a plurality of immunization schedules, by
      (a) identifying a first group of mammals and at least a second group of mammals, said mammals being of the same species, the first group of mammals having been immunized with one or more doses of one or more infectious disease-causing organism-associated immunogens according to a first screened immunization schedule, and the second group of mammals having been immunized with one or more doses of one or more infectious disease-causing organism-associated immunogens according to a second screened immunization schedule, each group of mammals having been immunized according to a different immunization schedule, and
      (b) comparing the effectiveness of said first and second screened immunization schedules in protecting against or inducing a chronic immune-mediated disorder in said first and second groups, as a result of which one of said screened immunization schedules may be identified as a lower risk screened immunization schedule and the other of said screened schedules as a higher risk screened immunization schedule with regard to the risk of developing said chronic immune mediated disorder(s),
   (II) immunizing said subject according to a subject immunization schedule, according to which at least one of said infectious disease-causing organism-associated immunogens of said lower risk schedule is administered in accordance with said lower risk screened immunization schedule, which administration is associated with a lower risk of development of said chronic immune-mediated disorder(s) than when said immunogen was administered according to said higher risk screened immunization schedule.

2. The method of claim 1 wherein said chronic immune mediated disorder is an autoimmune disease.

3. The method of claim 1, wherein said chronic immune mediated disorder is diabetes mellitus.

4. The method of claim 1 wherein the first dose of at least one immunogen in at least one of said immunization schedules is given when the mammals are less than 42 days old.

5. The method of claim 1 in which the first dose of at least one immunogen in at least one of said immunization schedules is given when the mammals are less than 14 days old.

6. The method in claim 1 wherein at least one group receives, according to its immunization schedule, more than one dose of at least one immunogen.

7. The method of claim 1, wherein for at least one immunogen in at least one schedule, the total dosage during the first 112 days after birth is substantially greater than that required for protection against the infectious disease with which it is associated.

8. The method of claim 1 wherein in at least one schedule at least one immunogen is administered by a route other than intravenously.

9. The method of claim 1 wherein in at least one schedule at least one immunogen is administered subcutaneously, intradermally, or intramuscularly.

10. The method of claim 1 wherein in at least one schedule at least one immunogen is administered other than as an immunogen of a live vaccine.

11. The method of claim 1 wherein in at least one schedule at least one immunogen is not a BCG immunogen.

12. The method of claim 1 wherein at least one immunogen of said subject immunization schedule which was also included in said lower risk schedule is one other than a pertussis immunogen.

13. The method of claim 1 wherein the incidence of the disorder in said groups is compared.

14. The method of claim 1 wherein the method is part of a production process to test vaccine lots for efficacy or safety.

15. The method of claim 1 wherein the method is part of a development process or clinical trial of a vaccine to test a vaccine for safety or efficacy.

16. The method of claim 1 wherein said mammals are human.

17. The method of claim 1 wherein said mammals are rodents and diabetes has not been chemically induced by streptozotocin.

18. The method of claim 1 wherein said mammals are NOD mice or BB rats.

19. The method of claim 1 wherein the comparison of (I) is prospective.

20. The method of claim 1 wherein said mammals are randomized in said groups.

21. The method of claim 1 wherein at least one said groups receives at least one potentially pharmaceutically acceptable dose of each at least two potentially pharmaceutically acceptable immunogenic agents which comprise at least one potentially pharmaceutically acceptable first pediatric immunogen and at least one agent selected from the group consisting of a second pediatric immunogen and a non-pediatric immunogen.

22. The method of claim 1 wherein one screened schedule provides at least one immunogen not provided by another screened schedule or fails to provide at least one immunogen provided by another screened schedule.

23. The method of claim 1 wherein one screened schedule provides a higher or lower dose of at least one immunogen than that provided for the same immunogen in said another screened schedule.

24. The method of claim 1 wherein one screened schedule provides a different number of doses of at least one immunogen than is provided for the same immunogen by another screened schedule.

25. The method of claim 1 wherein one screened schedule provides at least one dose of at least one immunogen at a later or earlier time from birth than the corresponding dose of the same immunogen is provided by another screened schedule.

26. The method of claim 1 wherein at least one group first receives at least one immunogen starting after 41 days of life.

27. The method of claim 1 wherein at least one immunogen is first administered to at least one group starting after 41 days after birth but before 180 days after birth.

28. The method of claim 1 wherein at least the majority of the mammals in at least one group did not develop the infectious diseases which are associated with said immunogens.

29. The method of claim 1 wherein mammals are excluded from a treatment group if:
   i) said mammals have substantial immunologic protection against the infectious disease which said immunization schedule protects against, or
   ii) said mammals have substantial levels of at least one surrogate marker of an autoimmune disease even though the mammals had not been previously diagnosed as having an autoimmune disease, or
   iii) said surrogate marker was substantially increased following a previous vaccination, infection or other immunologic challenge.

30. The method of claim 1, wherein both a pediatric immunogen and a non-pediatric immunogen are administered to at least one group.

31. The method of claim 1 in which the mammals are humans and the groups are compared for a period from first administration for at least one year.

32. The method of claim 1 in which the mammals are humans and the groups are compared from first administration until at least 5 years of age.

33. The method of claim 1 in which the mammals are rodents and groups are compared from first administration until at least 24.5 weeks of age.

34. The method of claim 1 wherein in at least one schedule at least one immunogen is administered with a depot adjuvant.

35. The method of claim 1 wherein the disorder is not an immune-mediated cancer.

36. The method of claim 1, further comprising determining whether the age of the subject mammal, at the time of commencement of the immunization schedule, affects the incidence, prevalence, or frequency of the disorder.

37. The method of claim 1, wherein the effect of the schedules on the incidence, prevalence, or frequency of the disorder is determined at least one year after at least two of the screened immunization schedules first differ.

38. The method of claim 1 in which the subject immunization schedule is identical to one of said screened schedules.

39. The method of claim 1 where said subject immunization schedule also protects the subject against at least one infectious disease.

40. The method of claim 1 where said subject immunization schedule also protects the subject against at least two infectious diseases.

41. The method of claim 1 wherein the ability of said screened immunization schedules to protect against an infectious disease is also compared.

42. The method of claim 1 wherein at least one group receives an immunogen at a time sufficiently early enough to substantially reduce the incidence of said disorder, sufficient number of mammals are followed after immunization for a sufficiently long interval to ensure that said mammals have an effect lasting for a clinically significant period of time after discontinuation of immunization, and the method does not involve the administration of an live organism leading to the infection of mammals for the duration of the time they are followed.

43. The method of claim 1, wherein said chronic immune mediated disorder is diabetes mellitus, wherein the mammals are humans, and wherein the effect of the schedules on the incidence, prevalence, frequency of the disorder is determined at least one year after said first and second immunization schedules differ.

44. The method of claim 43 wherein said mammals are randomized in said groups.

45. The method of claim 43 wherein both a pediatric immunogen and a non-pediatric immunogen are administered to at least one group.

46. The method of claim 43 wherein at least one immunogen is administered one other than as an immunogen of a live vaccine and wherein the first dose in at least one of said immunization schedules is given when the mammals are less than 42 days old.

47. The method of claim 43 wherein the incidence of the disorder in said groups is compared and wherein at least one immunogen is first administered to at least one group starting after 41 days after birth but before 180 days after birth.

48. The method of claim 43, further comprising determining whether the age of the subject mammal, at the time of commencement of the immunization schedule, affects the incidence, prevalence, or frequency of the disorder, wherein at least one immunogen is administered one other than as an immunogen of a live vaccine.

49. The method of claim 43 wherein incidence of the disorder in said groups is compared for at least two different chronic immune-mediated disorders, one of which is diabetes mellitus.

50. The method of claim 1 where at least one screened schedule calls for immunizing mammals starting at less than 42 days after birth and the screened immunization schedules differ as to the age at the time of the first dose of at least one other immunogen.

51. The method of claim 50 where said mammals in at least one schedule receive hepatitis B immunogen prior to 42 days after birth.

52. The method of claim 1 where said comparison comprises compensation for at least one confounding variable.

53. The method of claim 52 where the analysis includes compensation for confounding variables selected from the group consisting of breast feeding, receiving antibiotics, the maternal age, family history of diabetes or a second chronic immune mediated disorder, maternal infections while the mammal was in utero, infections during the first 12 months of life, size of the mammal at birth, gestational age of the mammal at birth, and exposure to vaccines.

54. The method of claim 1 in which, in (I)(b), the incidence, prevalence or frequency of at least one chronic immune-mediated disorder is compared, and the lower risk screened immunization schedule is associated with a lower incidence, prevalence or frequency of that disorder.

55. The method of claim 1 where the first and second groups differ by at least one of the following differences:
   a) the presence of at least one immunogen in the schedule for one group and not the other;
   b) a difference in the size of the dose of at least one immunogen administered to both groups;
   c) a difference in the number of doses of at least one immunogen administered to both groups; or
   d) a difference in the day of administration, relative to birth, of the first dose of at least one immunogen administered to both groups.

56. The method of claim 55 where at least one of said differences (a)–(d) relates to at least one immunogen other than a BCG immunogen.

57. The method of claim 55 where at least one of said differences (a)–(d) relates to at least one immunogen other than a BCG or measles immunogen.

58. The method of claim 55 where at least one of said differences (a)–(d) relates to at least one immunogen other than a BCG, measles, mumps, rubella, smallpox, diphtheria, tetanus, pertussis or polio immunogen.

59. The method of claim 55 where at least difference (a) applies.

60. The method of claim 55 where at least difference (b) applies.

61. The method of claim 55 where at least difference (c) applies.

62. The method of claim 55 where at least difference (d) applies.

63. The method of claim 55 where at least two of differences (a)–(d) apply.

64. The method of claim 55 where at least three of differences (a)–(d) apply.

65. The method of claim 55 where all of differences (a)–(d) apply.

66. The method of claim 55 where the chronic immune-mediated disorder is diabetes.

67. The method of claim 55 where the subjects are human.

68. The method of claim 67 where the mammals of said groups are human.

69. The method of claim 55 wherein the effect of the schedule on the incidence, prevalence, or frequency of the disorder is observed at least one year after the first difference in immunization between the groups is manifest.

70. The method of claim 68 wherein the effect of the schedule on the incidence, prevalence, or frequency of the disorder is observed at least one year after the first difference in immunization between the groups is manifest.

71. A method of immunizing a mammalian subject which comprises:
   (I) screening a plurality of immunization schedules, by
      (a) identifying a first group of mammals and at least a second group of mammals, said mammals being of the same species, the first group of mammals having been immunized with one or more doses of one or more infectious disease-causing organism-associated immunogens according to a first screened immunization schedule, and the second group of mammals having been immunized with one or more doses of one or more infectious disease-causing organism-associated immunogens according to a second screened immunization schedule, each group of mammals having been immunized according to a different immunization schedule, and
      (b) comparing the effectiveness of said first and second screened immunization schedules in protecting against or inducing a chronic immune-mediated disorder in said first and second groups, as a result of which one of said screened immunization schedules may be identified as a lower risk screened immunization schedule and the other of said screened schedules as a higher risk screened immunization schedule with regard to the risk of developing said chronic immune mediated disorder(s),
where the first dose of at least one infectious disease-causing organism associated immunogen given to both groups is given sooner after birth according to the first screened immunization schedule than according to the second schedule (each such immunogen so administered to said first group being hereafter referred to as an "early" immunogen regardless of its time of administration in the second group), and (II) immunizing said subject according to a subject immunization schedule, according to which at least one of said early infectious disease-causing organism-associated immunogens is administered in accordance with said lower risk screened immunization schedule, which administration is associated with a lower risk of development of said chronic immune-mediated disorder(s) than when said immunogen was administered according to said higher risk screened immunization schedule.

72. The method of claim 71 in which the disorder is an autoimmune disease.

73. The method of claim 72 in which the disorder is diabetes mellitus.

74. The method of claim 72 in which the disorder is SLE.

75. The method of claim 72 in which at least one comparison (b) is made at least one year after first administration of an early immunogen to said mammals.

76. The method of claim 72 where said mammalian subject is or said mammals are humans.

77. The method of claim 73 where said mammalian subject is or said mammals are humans.

78. The method of claim 77 in which at least one comparison (b) is made at least one year after first administration of an early immunogen to said mammals.

79. The method of claim 78 where at least one of said early immunogens is one other than BCG or pertussis immunogen.

80. The method of claim 71 where the first dose of at least one early immunogen is given according to a screened schedule starting at less than 42 days after birth.

81. The method of claim 73 where the first dose of at least one early immunogen is given according to a screened schedule starting at less than 42 days after birth.

82. The method of claim 78 where the first dose of at least one early immunogen is given according to a screened schedule starting at less than 42 days after birth.

83. The method of claim 79 where the first dose of at least one early immunogen is given according to a screened schedule starting at less than 42 days after birth.

84. The method of claim 80 where at least two immunogens are administered according to said subject immunization schedule, and such immunogens include (1) a first immunogen which was given prior to 42 days after birth to said first and second groups, and (2) a second and different immunogen which is an early immunogen.

85. The method of claim 78 further comprising (III) screening said subject, during or after receipt of said third schedule, for the development of diabetes.

86. The method of claim 78 where the incidence of diabetes is compared.

87. The method of claim 71 where at least two of the screened schedules also differ by either the presence of at least one immunogen or the number of doses of at least one immunogen.

88. The method of claim 71 where at least one infectious disease-causing organism-associated immunogen is administered to said subject so as to protect said subject against said infectious disease.

89. The method of claim 88 where at least two different immunogens are administered so as to protect the subject against at least two different infectious diseases.

90. The method of claim 88 where the immunogen protective against said infectious disease is an early immunogen.

91. The method of claim 71 where the screened schedules do not differ by either the presence of at least one immunogen or the number of doses of at least one immunogen.

92. The method of claim 78 where said lower risk of development of diabetes is evidenced by a lower incidence or frequency, or a slower onset, of diabetes.

93. A method of immunizing a mammalian subject which comprises (I) (a) immunizing a first group of mammals with one or more doses of one or more infectious disease-causing organism-associated immunogens according to a first screened immunization schedule, (b) immunizing at least a second group of mammals with one or more doses of one or more infectious disease-causing organism-associated immunogens according to a second screened immunization schedule, the first and second groups being of the same species, and (c) comparing the effectiveness of said first and second screened immunization schedules in protecting against or inducing a chronic immune-mediated disorder in said first and second groups, as a result of which one of said screened immunization schedules may be identified as a lower risk screened immunization schedule and the other of said screened schedules as a higher risk screened immunization schedule with regard to the risk of developing said chronic immune mediated disorder(s), where the first dose of at least one infectious disease-causing organism-associated immunogen given to both groups is given sooner after birth according to the first screened immunization schedule than according to the second schedule (each such immunogen so administered to said first group being hereafter referred to as an "early" immunogen regardless of its time of administration in the second group), and (II) immunizing said subject according to a subject immunization schedule, according to which at least one of said early, infectious disease-causing organism-associated immunogens is administered in accordance with said lower risk screened immunization schedule, resulting in a lower risk of development of said chronic immune-mediated disorder(s) than when said immunogen was administered according to said higher risk screened immunization schedule.

94. The method of claim 93 where one of said chronic immune-mediated disorders is diabetes, where said mammalian subject is or said mammals are humans, where said comparison (b) is made at least one year after first administration of said immunogen to said mammals.

95. The method of claim 94 where at least one of said early immunogens is one other than BCG or pertussis immunogen.

96. A method of protecting a mammalian subject, by immunization, against at least one infectious disease while reducing the risk of said subject thereby developing a chronic immune mediated disorder, which comprises:

(I) screening a plurality of immunization schedules, by
(a) identifying a first group of mammals and at least a second group of mammals, said mammals being of the same species, the first group of mammals having been immunized with one or more doses of one or more infectious disease-causing organism-associated immunogens according to a first screened immunization schedule, and the second group of mammals having been immunized with one or more doses of one or more infectious disease-causing organism-associated immunogens according to a second screened immunization schedule, each group of mammals having been immunized according to a different immunization schedule, and (b) comparing the effectiveness of said first and second screened immunization schedules in protecting against or inducing a chronic immune-mediated disorder in said first and second groups, as a result of which one of said screened immunization schedules may be identified as a lower risk screened immunization schedule and the other of said screened schedules as a higher risk screened immunization schedule with regard to the risk of developing said chronic immune mediated disorder(s), where the first dose of at least one infectious disease-causing organism associated immunogen given to both groups is given sooner after birth according to the first screened immunization schedule than according to the second schedule (each such immunogen so administered to said first group being hereafter referred to as an "early" immunogen regardless of its time of administration in the second group), and (II) immunizing said subject according to a subject immunization schedule, according to which at least one of said early infectious disease-causing organism-associated immunogens is administered in accordance with said lower risk screened immunization schedule, which administration is associated with a lower risk of development of said chronic immune-mediated disorder(s) than when said immunogen was administered according to said higher risk screened immunization schedule, at least one of the immunogens of (II) being protective against said infectious disease when administered according to aid third immunization schedule, said third schedule presenting a reduced risk of said subject developing a chronic immune mediated disorder relative to said second schedule.

97. The method of claim 96 where one of said chronic immune-mediated disorders is diabetes, where said mammalian subject is or said mammals are humans, and where said comparison (b) is made at least one year after first administration of said immunogen to said mammals.

98. A method of immunizing a mammalian subject which comprises:

(I) screening a plurality of immunization schedules, by (a) identifying a first group of mammals and at least a second group of mammals, said mammals being of the same species, the first group of mammals having been immunized with one or more doses of one or more immunogens according to a first screened immunization schedule, and the second group of mammals having been immunized with one or more doses of one or more immunogens according to a second screened immunization schedule, each group of mammals having been immunized according to a different immunization schedule, and (b) comparing the incidence, frequency, prevalence, or time of onset of said chronic immune-mediated disorder in the first group with that in the second group, where the first dose of at least one immunogen given to both groups is given (i) sooner after birth according to the first screened immunization schedule than according to the second schedule (each such immunogen so administered to said first group being hereafter referred to as an "early" immunogen regardless of its time of administration in the second group), or (ii) according to the first screened immunization schedule when the mammals of the first group are less than 42 days old (each such immunogen is administered to said first group being hereafter referred to as a "pre-42" immunogen regardless of its time of immunization in the second group);

(II) immunizing said subject according to a subject immunization schedule, according to which at least one of said early or pre-42 immunogens is administered in accordance with said first screened immunization schedule, and is associated with a lower incidence, frequency, or prevalence, or slower onset, of a chronic immune-mediated disorder than when said immunogen was administered according to said second screened immunization schedule.

99. The method of claim 98 where one of said chronic immune-mediated disorders is diabetes, where said mammalian subject is or said mammals are humans, where said comparison (b) is made at least one year after first administration of said immunogen to said mammals.

100. The method of claim 71 in which, in at least one screened schedule, the first dose of said immunization schedule is administered before the mammal's immune system arrives at a state of maturation comparable to that achieved at an age of 42 days after birth in a mouse or rat.

101. The method of claim 71 in which, in said subject schedule, the first dose of said immunization schedule is administered before the subject's immune system arrives at a state of maturation comparable to that achieved at an age of 42 days after birth in a mouse or rat.

102. The method of claim 73 in which, in at least one screened schedule, the first dose of said immunization schedule is administered before the mammal's immune system arrives at a state of maturation comparable to that achieved at an age of 42 days after birth in a mouse or rat.

103. The method of claim 73 in which, in said subject schedule, the first dose of said immunization schedule is administered before the subject's immune system arrives at a state of maturation comparable to that achieved at an age of 42 days after birth in a mouse or rat.

104. A method of protecting a mammalian subject, by immunization, against at least one infectious disease while reducing the risk of said subject thereby developing a chronic immune mediated disorder, which comprises:

immunizing said subject according to a subject immunization schedule, according to which one or more immunogens is administered to the subject, each immunogen being administered on one or more dates according to such schedule, where it has previously been determined that the timing of first administration of at least one of said immunogens influences the risk of said subject thereby developing said disorder, and where the first administration of at least one risk-influencing immunogen according to said schedule is timed so as to reduce the risk of said subject thereby developing said disorder, relative to the risk if said first administration had been at some later date.

105. The method of claim 104 where said determination was made by
(I) screening a plurality of immunization schedules, by
(a) identifying a first group of mammals and at least a second group of mammals, said mammals being of the same species, the first group of mammals having been immunized with one or more doses of one or more infectious disease-causing organism-associated immunogens according to a first screened immunization schedule, and the second group of mammals having been immunized with one or more doses of one or more infectious disease-causing organism-associated immunogens according to a second screened immunization schedule, each group of mammals having been immunized according to a different immunization schedule, and
(b) comparing the effectiveness of said first and second screened immunization schedules in protecting against or inducing a chronic immune-mediated disorder in said first and second groups, as a result of which one of said screened immunization schedules may be identified as a lower risk screened immunization schedule and the other of said screened schedules as a higher risk screened immunization schedule with regard to the risk of developing said chronic immune mediated disorder(s).

106. The method of claim 104 where the disorder is diabetes.

107. The method of claim 37 where said disorder is diabetes.

108. The method of claim 107 in which at least one immunogen is first administered to said subject at less than 42 days after birth, and said determining was performed at least one year after said first immunization.

109. A business method for developing safer methods of protecting humans against infectious diseases by immunizing humans with one or more doses of one or more immunogens which induce protective immunity to one or more infectious diseases when administered according to one or more immunization schedules, said method comprising
I. evaluating the association between said immunization schedule and one or more chronic immune mediated disorders by
a) comparing the incidence, prevalence or frequency of a chronic immune mediated disorder in a group comprising humans where the majority receive an immunization schedule comprising said one or more immunogens to that in a control group comprising humans where the majority receive a different immunization schedule, or
b) comparing the risk of said chronic immune mediated disorder associated between two or more immunization schedules,
where the comparisons each comprise a time span of at least one year after the administration of said one or more immunogens, and
II. determining one or more methods of immunization to allow safe immunization with said immunogenic agent reflective of the analysis from I.

110. A business method for developing safer methods of protecting humans against infectious diseases by immunizing humans with one or more doses of one or more immunogens which induce protective immunity to one or more infectious diseases when administered according to one or more immunization schedules, said method comprising
(I) screening a plurality of immunization schedules, by
(a) identifying a first group of mammals and at least a second group of mammals, said mammals being of the same species, the first group of mammals having been immunized with one or more doses of one or more infectious disease-causing organism-associated immunogens according to a first screened immunization schedule, and the second group of mammals having been immunized with one or more doses of one or more infectious disease-causing organism-associated immunogens according to a second screened immunization schedule, each group of mammals having been immunized according to a different immunization schedule, and
(b) comparing the incidence, prevalence or frequency of at least one chronic immune-mediated disorder in said first and second groups, as a result of which one of said screened immunization schedules may be identified as a lower risk screened immunization schedule and the other of said screened schedules as a higher risk screened immunization schedule with regard to the incidence or severity of said chronic immune mediated disorder(s), and
II. selecting an immunization schedule which protects humans against such infectious disease, but would be expected to result in a reduced incidence, prevalence or frequency of said disorder relative to that observed in at least one of said groups.

111. The method of 110 further comprising comparing the incidence, prevalence, frequency or severity of said infectious disease in the same or equivalent groups.

112. The method of claim 1 in which three or more groups, each with a different immunization schedule, are compared.

113. The method of claim 3 wherein the first dose of at least one immunogen in at least one of said immunization schedules is given when the mammals are less than 42 days old.

* * * * *

(12) INTER PARTES REEXAMINATION CERTIFICATE (1010th)
United States Patent
Classen

(10) Number: US 6,638,739 C1
(45) Certificate Issued: *Dec. 11, 2014

(54) METHOD AND COMPOSITION FOR AN EARLY VACCINE TO PROTECT AGAINST BOTH COMMON INFECTIOUS DISEASES AND CHRONIC IMMUNE MEDIATED DISORDERS OR THEIR SEQUELAE

(75) Inventor: John Barthelow Classen, Baltimore, MD (US)

(73) Assignee: Classen Immunotherapies, Inc., Baltimore, MD (US)

Reexamination Request:
No. 95/002,224, Sep. 13, 2012

Reexamination Certificate for:
Patent No.: 6,638,739
Issued: Oct. 28, 2003
Appl. No.: 10/124,363
Filed: Apr. 18, 2002

( * ) Notice: This patent is subject to a terminal disclaimer.

Related U.S. Application Data

(63) Continuation of application No. 09/611,415, filed on Jul. 6, 2000, now Pat. No. 6,420,139, which is a continuation of application No. 08/591,651, filed as application No. PCT/US94/08825 on Aug. 4, 1994, which is a continuation of application No. 08/104,529, filed on Aug. 12, 1993, now Pat. No. 5,728,385.

(51) Int. Cl.
*C12N 15/09* (2006.01)
*C12N 5/00* (2006.01)
*G01N 33/53* (2006.01)

(52) U.S. Cl.
USPC .......................... 435/69.3; 435/325; 435/7.1

(58) Field of Classification Search
None
See application file for complete search history.

(56) References Cited

To view the complete listing of prior art documents cited during the proceeding for Reexamination Control Number 95/002,224, please refer to the USPTO's public Patent Application Information Retrieval (PAIR) system under the Display References tab.

*Primary Examiner* — Shri Ponnaluri

(57) ABSTRACT

A method of immunization, and compositions therefor, are provided for substantially preventing or reducing the symptoms of at least one infectious disease and at least one chronic immune mediated disorder. An immunogenic challenge which supplements the normal childhood immunization schedule can help ensure the proper maturation of the immune system and prevent the development of chronic immune mediated disorders, such as immune-mediated diabetes or SLE.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-6, 8-12, 16, 21, 25-28, 30-31, 34-35, 38-40, 42-43, 45-46, 52-53, 55-58, 62, 66-68, 71-73, 75-83, 85, 88-91, 96-97, 109-110, 112 and 113 are cancelled.

Claims 7, 13-15, 17-20, 22-24, 29, 32-33, 36-37, 41, 44, 47-51, 54, 59-61, 63-65, 69-70, 74, 84, 86-87, 92-95, 98-108 and 111 were not reexamined.

\* \* \* \* \*